(12) United States Patent
Schaller

(10) Patent No.: US 11,801,163 B2
(45) Date of Patent: Oct. 31, 2023

(54) MULTI-STAGE TRIGGER FOR OPHTHALMOLOGY CUTTING TOOL

(71) Applicant: Carl Zeiss Meditec Cataract Technology Inc., Reno, NV (US)

(72) Inventor: Michael Schaller, Reno, NV (US)

(73) Assignee: Carl Zeiss Meditec Cataract Technology Inc., Reno, NV (US)

( * ) Notice: Subject to any disclaimer, the term of this patent is extended or adjusted under 35 U.S.C. 154(b) by 839 days.

(21) Appl. No.: 16/875,421

(22) Filed: May 15, 2020

(65) Prior Publication Data

US 2020/0383833 A1   Dec. 10, 2020

Related U.S. Application Data

(60) Provisional application No. 62/858,785, filed on Jun. 7, 2019.

(51) Int. Cl.
  *A61F 9/007* (2006.01)
  *A61B 17/00* (2006.01)
  *A61M 1/00* (2006.01)

(52) U.S. Cl.
  CPC ...... *A61F 9/00736* (2013.01); *A61F 9/00763* (2013.01); *A61B 2017/00734* (2013.01);
  (Continued)

(58) Field of Classification Search
  CPC .............. A61F 9/00736; A61F 9/00763; A61F 9/00754; A61F 9/007; A61F 9/0061;
  (Continued)

(56) References Cited

U.S. PATENT DOCUMENTS 1,833,687 A    11/1931   Neivert
2,947,470 A    8/1960    Ruben et al.
(Continued)

FOREIGN PATENT DOCUMENTS

CN    1242824 A    1/2000
CN    1494443 A    5/2004
(Continued)

OTHER PUBLICATIONS

Vibration, First recorded in 1645-1655, Dictionary.com (Year: 1645). 5 pages.
(Continued)

*Primary Examiner* — Erich G Herbermann
(74) *Attorney, Agent, or Firm* — Mintz Levin Cohn Ferris Glovsky and Popeo, P.C.

(57) ABSTRACT

A medical device for removing lens tissue from inside a capsular bag of an eye including a cam assembly operatively coupled to a vacuum generation source positioned within the housing. A first portion is operatively coupled to the vacuum generation source and a second portion is operatively coupled to the first portion and to the shaft. The first portion is capable of rotating about an axis to cause the vacuum generation source to generate vacuum through the lumen. The second portion is capable of rotating about the axis with the first portion to cause the shaft to oscillate. A first degree of actuation of a trigger causes the vacuum generation source to generate vacuum within the lumen of the shaft, and a second degree of actuation of the trigger causes the shaft to oscillate as the second portion rotates. Related systems, devices, and methods are provided.

22 Claims, 31 Drawing Sheets

(52) U.S. Cl.
CPC ... *A61B 2217/005* (2013.01); *A61B 2217/007* (2013.01); *A61M 1/774* (2021.05); *A61M 1/81* (2021.05)

(58) Field of Classification Search
CPC ..... A61F 9/0008; A61F 9/0026; A61M 1/774; A61M 1/81; A61B 2017/00734; A61B 2217/005; A61B 2217/007
See application file for complete search history.

(56) References Cited

U.S. PATENT DOCUMENTS

| | | |
|---|---|---|
| 3,183,849 A | 5/1965 | Raymond |
| 3,589,363 A | 6/1971 | Banko et al. |
| 3,957,052 A | 5/1976 | Topham |
| 3,990,452 A | 11/1976 | Murry et al. |
| 4,368,734 A | 1/1983 | Banko |
| 4,493,706 A | 1/1985 | Borsanyi et al. |
| 4,508,532 A | 4/1985 | Drews et al. |
| 4,643,187 A | 2/1987 | Okada |
| 4,705,500 A | 11/1987 | Reimels et al. |
| 4,732,150 A | 3/1988 | Keener, Jr. |
| 4,764,165 A | 8/1988 | Reimels et al. |
| 4,854,825 A | 8/1989 | Bez et al. |
| 4,869,716 A | 9/1989 | Smirmaul |
| 4,891,044 A | 1/1990 | Mitchell |
| 4,908,015 A | 3/1990 | Anis |
| 4,921,477 A | 5/1990 | Davis |
| 5,146,921 A | 9/1992 | Terwilliger et al. |
| 5,222,959 A | 6/1993 | Anis |
| 5,275,607 A | 1/1994 | Lo et al. |
| 5,279,547 A | 1/1994 | Costin |
| 5,337,780 A | 8/1994 | Kee et al. |
| 5,350,390 A | 9/1994 | Sher |
| 5,437,678 A | 8/1995 | Sorensen |
| 5,651,783 A | 7/1997 | Reynard |
| 5,676,649 A | 10/1997 | Boukhny et al. |
| 5,693,062 A | 12/1997 | Stegmann et al. |
| 5,755,561 A | 5/1998 | Couillard et al. |
| 5,788,667 A | 8/1998 | Stoller et al. |
| 5,788,679 A | 8/1998 | Gravlee, Jr. |
| 5,807,401 A | 9/1998 | Grieshaber et al. |
| 5,833,643 A | 11/1998 | Ross et al. |
| 5,843,071 A | 12/1998 | Bath |
| 5,891,153 A | 4/1999 | Peterson |
| 5,911,699 A | 6/1999 | Anis et al. |
| 5,938,677 A | 8/1999 | Boukhny et al. |
| 6,004,284 A | 12/1999 | Sussman et al. |
| 6,013,049 A | 1/2000 | Rockley et al. |
| 6,059,765 A | 5/2000 | Cole et al. |
| 6,074,396 A | 6/2000 | Geuder |
| 6,117,149 A | 9/2000 | Sorensen et al. |
| 6,132,436 A | 10/2000 | Portney |
| 6,165,190 A | 12/2000 | Nguyen |
| 6,183,433 B1 | 2/2001 | Bays |
| 6,186,148 B1 | 2/2001 | Okada |
| 6,241,700 B1 | 6/2001 | Leukanech |
| 6,254,587 B1 | 7/2001 | Christ et al. |
| 6,258,111 B1 | 7/2001 | Ross et al. |
| 6,299,591 B1 | 10/2001 | Banko |
| 6,319,222 B1 | 11/2001 | Andrew et al. |
| 6,322,557 B1 | 11/2001 | Nikolaevich et al. |
| 6,328,747 B1 | 12/2001 | Nun |
| 6,398,754 B1 | 6/2002 | Sutton et al. |
| 6,428,508 B1 | 8/2002 | Ross |
| 6,485,499 B1 | 11/2002 | Oberkamp et al. |
| 6,506,176 B1 | 1/2003 | Mittelstein et al. |
| 6,520,929 B2 | 2/2003 | Zaleski |
| 6,520,955 B2 | 2/2003 | Reynard |
| 6,527,766 B1 | 3/2003 | Bair |
| 6,544,254 B1 | 4/2003 | Bath |
| 6,589,201 B1 | 7/2003 | Sussman et al. |
| 6,592,541 B1 | 7/2003 | Kurwa |
| 6,605,054 B2 | 8/2003 | Rockley |
| 6,623,477 B1 | 9/2003 | Elbrecht et al. |
| 6,852,092 B2 | 2/2005 | Kadziauskas et al. |
| 6,860,868 B1 | 3/2005 | Sussman et al. |
| 6,939,317 B2 | 9/2005 | Zacharias |
| 6,939,341 B2 | 9/2005 | Vijfvinkel |
| 7,041,078 B1 | 5/2006 | Peyman |
| 7,083,589 B2 | 8/2006 | Banko et al. |
| 7,083,591 B2 | 8/2006 | Cionni |
| 7,141,047 B2 | 11/2006 | John |
| 7,172,601 B2 | 2/2007 | Ben-Nun |
| 7,182,759 B2 | 2/2007 | Kadziauskas et al. |
| 7,204,820 B2 | 4/2007 | Akahoshi |
| 7,285,107 B1 | 10/2007 | Charles |
| 7,303,566 B2 | 12/2007 | Kishimoto et al. |
| 7,544,178 B2 | 6/2009 | Kadziauskas et al. |
| 7,549,972 B2 | 6/2009 | Luloh et al. |
| 7,588,553 B2 | 9/2009 | Dewey |
| 7,845,235 B2 | 12/2010 | Sandu et al. |
| 7,846,126 B2 | 12/2010 | Steen et al. |
| 7,857,794 B2 | 12/2010 | Dimalanta et al. |
| 7,876,025 B2 | 1/2011 | Ma et al. |
| 7,955,060 B2 | 6/2011 | Gottschalk |
| 7,967,775 B2 | 6/2011 | Hong |
| 8,070,711 B2 | 12/2011 | Bassinger et al. |
| 8,080,029 B2 | 12/2011 | Charles |
| 8,142,388 B2 | 3/2012 | Gomez |
| 8,187,293 B2 | 5/2012 | Kirchhevel |
| 8,216,246 B2 | 7/2012 | Luloh et al. |
| 8,246,644 B2 | 8/2012 | Rockley et al. |
| 8,287,484 B2 | 10/2012 | Rockley |
| 8,298,253 B2 | 10/2012 | Charles |
| 8,308,735 B2 | 11/2012 | Dimalanta |
| 8,317,739 B2 | 11/2012 | Kuebler |
| 8,376,983 B2 | 2/2013 | Ross et al. |
| 8,423,126 B2 | 4/2013 | Mackool |
| 8,475,480 B2 | 7/2013 | Mackool |
| 8,545,462 B2 | 10/2013 | Ghannoum |
| 8,771,301 B2 | 7/2014 | Boukhny et al. |
| 8,784,361 B2 | 7/2014 | Lane |
| 8,801,653 B2 | 8/2014 | Maaskamp et al. |
| 8,852,139 B2 | 10/2014 | King et al. |
| 8,876,745 B2 | 11/2014 | Escaf |
| 8,876,747 B2 | 11/2014 | Kadziauskas et al. |
| 8,939,927 B2 | 1/2015 | Sorensen et al. |
| 8,986,290 B2 | 3/2015 | Patton |
| 9,050,171 B2 | 6/2015 | Foster |
| 9,144,517 B2 | 9/2015 | Kuebler et al. |
| 9,259,597 B2 | 2/2016 | Romano et al. |
| 9,351,871 B2 | 5/2016 | Ghannoum et al. |
| 9,370,611 B2 | 6/2016 | Ross et al. |
| 9,387,122 B2 | 7/2016 | Mackool |
| 9,402,766 B2 | 8/2016 | Akahoshi et al. |
| 9,433,725 B2 | 9/2016 | Schaller et al. |
| 9,439,807 B2 | 9/2016 | Koplin |
| 9,445,943 B2 | 9/2016 | Wilson et al. |
| 9,486,359 B2 | 11/2016 | Hauger et al. |
| 9,486,360 B2 | 11/2016 | Chon |
| 9,498,377 B2 | 11/2016 | McCary et al. |
| 9,498,378 B2 | 11/2016 | McDonell |
| 9,504,604 B2 | 11/2016 | Alvarez |
| 9,561,129 B2 | 2/2017 | Ross et al. |
| 9,566,188 B2 | 2/2017 | Raney et al. |
| 9,592,156 B2 | 3/2017 | Huang |
| 9,629,747 B2 | 4/2017 | Clauson et al. |
| 9,693,896 B2 | 7/2017 | Sussman |
| 9,724,238 B2 | 8/2017 | Heitel |
| 9,731,065 B2 | 8/2017 | Bourne et al. |
| 9,750,639 B2 | 9/2017 | Barnes et al. |
| 9,775,743 B2 | 10/2017 | Clauson et al. |
| 9,827,142 B2 | 11/2017 | Sasazaki et al. |
| 9,839,738 B2 | 12/2017 | Beauvais et al. |
| 9,861,522 B2 | 1/2018 | Sorensen et al. |
| 9,867,635 B2 | 1/2018 | Alvarez et al. |
| 9,878,075 B2 | 1/2018 | Sussman et al. |
| 9,889,247 B2 | 2/2018 | Akahoshi |
| 9,913,752 B2 | 3/2018 | Hauger |
| 10,231,870 B2 | 3/2019 | Clauson et al. |
| 10,251,782 B2 | 4/2019 | Farley |
| 10,278,861 B2 | 5/2019 | Bourne |
| 10,294,934 B2 | 5/2019 | Bourne et al. |

(56) References Cited

U.S. PATENT DOCUMENTS

| | | |
|---|---|---|
| 10,603,213 B2 | 3/2020 | Clauson et al. |
| 10,639,197 B2 | 5/2020 | Lopez et al. |
| 11,045,354 B2 | 6/2021 | Sorensen et al. |
| 11,147,709 B2 | 10/2021 | Kahook et al. |
| 11,278,450 B2 | 3/2022 | Clauson et al. |
| 2002/0052617 A1 | 5/2002 | Anis et al. |
| 2002/0099400 A1 | 7/2002 | Wolf et al. |
| 2002/0151835 A1 | 10/2002 | Ross |
| 2003/0004455 A1 | 1/2003 | Kadziauskas et al. |
| 2003/0055387 A1 | 3/2003 | Sutton et al. |
| 2003/0109867 A1 | 6/2003 | Gluche et al. |
| 2004/0010284 A1 | 1/2004 | Maloof et al. |
| 2004/0049217 A1 | 3/2004 | Ross et al. |
| 2004/0082902 A1 | 4/2004 | Kadziauskas et al. |
| 2004/0092800 A1 | 5/2004 | MacKool |
| 2004/0099247 A1 | 5/2004 | Nelson |
| 2004/0153093 A1 | 8/2004 | Donovan |
| 2005/0113741 A1 | 5/2005 | Huang et al. |
| 2005/0234441 A1 | 10/2005 | Bisch et al. |
| 2005/0234473 A1 | 10/2005 | Zacharias |
| 2006/0135974 A1 | 6/2006 | Perkins |
| 2006/0253056 A1 | 11/2006 | Kadziauskas et al. |
| 2007/0060926 A1 | 3/2007 | Escaf |
| 2007/0260173 A1 | 11/2007 | Boukhny et al. |
| 2008/0188792 A1 | 8/2008 | Barrett |
| 2008/0300531 A1 | 12/2008 | Gills, Jr. |
| 2009/0048607 A1 | 2/2009 | Rockley |
| 2009/0054904 A1 | 2/2009 | Holmen |
| 2009/0137993 A1 | 5/2009 | Kurtz |
| 2009/0149840 A1 | 6/2009 | Kurtz |
| 2009/0156985 A1 | 6/2009 | Hottmann et al. |
| 2009/0171242 A1 | 7/2009 | Hibner |
| 2010/0030134 A1 | 2/2010 | Fitzgerald et al. |
| 2010/0191178 A1 | 7/2010 | Ross et al. |
| 2010/0286651 A1 | 11/2010 | Sorensen |
| 2010/0292631 A1 | 11/2010 | Holden |
| 2010/0312170 A1 | 12/2010 | Maaskamp et al. |
| 2010/0331911 A1 | 12/2010 | Kovalcheck et al. |
| 2011/0015562 A1 | 1/2011 | Akahoshi |
| 2011/0054384 A1 | 3/2011 | Brown |
| 2011/0112466 A1 | 5/2011 | Dimalanta |
| 2011/0137231 A1 | 6/2011 | Sorensen et al. |
| 2011/0144638 A1 | 6/2011 | Heeren et al. |
| 2011/0290854 A1 | 12/2011 | Timm et al. |
| 2011/0295192 A1 | 12/2011 | Geuder |
| 2012/0004595 A1 | 1/2012 | Dubois et al. |
| 2012/0022434 A1 | 1/2012 | Lue et al. |
| 2012/0041358 A1 | 2/2012 | Mann et al. |
| 2012/0072197 A1 | 3/2012 | Ovchinnikov |
| 2012/0078181 A1 | 3/2012 | Smith et al. |
| 2012/0089080 A1 | 4/2012 | Ross et al. |
| 2012/0157908 A1 | 6/2012 | Underwood et al. |
| 2012/0158030 A1 | 6/2012 | Underwood et al. |
| 2012/0165734 A1 | 6/2012 | Auld et al. |
| 2012/0184892 A1 | 7/2012 | Bigler et al. |
| 2012/0259320 A1 | 10/2012 | Loesel et al. |
| 2013/0043023 A1 | 2/2013 | Hallundbaek |
| 2013/0060210 A1 | 3/2013 | Ross et al. |
| 2013/0231605 A1 | 9/2013 | Walter |
| 2013/0282020 A1 | 10/2013 | Hunter |
| 2013/0317417 A1 | 11/2013 | Claus et al. |
| 2014/0005681 A1 | 1/2014 | Gee et al. |
| 2014/0012186 A1 | 1/2014 | Thyzel |
| 2014/0052113 A1 | 2/2014 | Kuehnert et al. |
| 2014/0074013 A1 | 3/2014 | McCary et al. |
| 2014/0081151 A1 | 3/2014 | Saimovici |
| 2014/0081266 A1 | 3/2014 | Dubois et al. |
| 2014/0114335 A1 | 4/2014 | Banko |
| 2014/0163455 A1 | 6/2014 | Wilson et al. |
| 2014/0194860 A1 | 7/2014 | Dick et al. |
| 2014/0236163 A1 | 8/2014 | Olson et al. |
| 2014/0257258 A1 | 9/2014 | Kurtz |
| 2014/0271251 A1 | 9/2014 | Bourne et al. |
| 2014/0276364 A1 | 9/2014 | Sussman |
| 2014/0309649 A1 | 10/2014 | Alvarez et al. |
| 2014/0358155 A1 | 12/2014 | DeBoer et al. |
| 2014/0360494 A1 | 12/2014 | Herskovic |
| 2014/0364885 A1 | 12/2014 | Wells et al. |
| 2015/0005753 A1 | 1/2015 | Walter |
| 2015/0025450 A1 | 1/2015 | King et al. |
| 2015/0038894 A1 | 2/2015 | Urich et al. |
| 2015/0045806 A1 | 2/2015 | Urich et al. |
| 2015/0105791 A1 | 4/2015 | Truckai |
| 2015/0125328 A1 | 5/2015 | Bourne et al. |
| 2015/0141801 A1 | 5/2015 | Jean et al. |
| 2015/0144514 A1 | 5/2015 | Brennan et al. |
| 2015/0148615 A1 | 5/2015 | Brennan et al. |
| 2015/0196426 A1 | 7/2015 | Kuebler et al. |
| 2015/0202081 A1 | 7/2015 | Eichler |
| 2015/0216722 A1 | 8/2015 | Choate |
| 2015/0216728 A1 | 8/2015 | Keller |
| 2015/0257927 A1 | 9/2015 | Olson |
| 2015/0297407 A1 | 10/2015 | Saimovici |
| 2015/0306286 A1 | 10/2015 | Ross et al. |
| 2015/0328047 A1 | 11/2015 | Falck, Jr. |
| 2015/0359672 A1 | 12/2015 | Van Valen et al. |
| 2016/0022489 A1 | 1/2016 | Hartstra |
| 2016/0058614 A1 | 3/2016 | Ross et al. |
| 2016/0067091 A1 | 3/2016 | Wells et al. |
| 2016/0074220 A1 | 3/2016 | Ianchulev et al. |
| 2016/0089268 A1 | 3/2016 | Chon et al. |
| 2016/0095749 A1 | 4/2016 | Raney et al. |
| 2016/0095750 A1 | 4/2016 | Raney et al. |
| 2016/0106580 A1 | 4/2016 | Banko |
| 2016/0106893 A1 | 4/2016 | Zacharias |
| 2016/0128869 A1 | 5/2016 | Zacharias |
| 2016/0135991 A1 | 5/2016 | Farley et al. |
| 2016/0143780 A1 | 5/2016 | Gunn |
| 2016/0166432 A1 | 6/2016 | Kahook et al. |
| 2016/0175578 A1 | 6/2016 | Roholt |
| 2016/0220807 A1 | 8/2016 | Bono |
| 2016/0346121 A1 | 12/2016 | Ianchulev et al. |
| 2017/0007451 A1 | 1/2017 | Depenbusch |
| 2017/0007452 A1 | 1/2017 | Depenbusch |
| 2017/0020728 A1 | 1/2017 | McDonell |
| 2017/0027750 A1 | 2/2017 | Wiley |
| 2017/0087013 A1 | 3/2017 | Prats et al. |
| 2017/0151091 A1 | 6/2017 | Bourne et al. |
| 2017/0151378 A1 | 6/2017 | Raney et al. |
| 2017/0172796 A1 | 6/2017 | Biancalana et al. |
| 2017/0211959 A1 | 7/2017 | Adler et al. |
| 2017/0312125 A1 | 11/2017 | Clauson et al. |
| 2017/0333252 A1 | 11/2017 | Biancalana et al. |
| 2017/0360607 A1 | 12/2017 | Price et al. |
| 2017/0367885 A1 | 12/2017 | Bourne |
| 2018/0028360 A1 | 2/2018 | Kozawa |
| 2018/0036171 A1 | 2/2018 | Clauson et al. |
| 2018/0049920 A1 | 2/2018 | Charles |
| 2018/0049921 A1 | 2/2018 | Sorensen et al. |
| 2018/0058438 A1 | 3/2018 | Ochoa |
| 2018/0064578 A1 | 3/2018 | Clauson et al. |
| 2018/0318132 A1 | 11/2018 | Clauson et al. |
| 2018/0318133 A1* | 11/2018 | Clauson ........... A61B 17/22031 |
| 2019/0015252 A1 | 1/2019 | Lake et al. |
| 2019/0041665 A1 | 2/2019 | Widman et al. |
| 2019/0099292 A1 | 4/2019 | Strayer et al. |
| 2019/0133825 A1 | 5/2019 | Clauson et al. |
| 2019/0151149 A1 | 5/2019 | Clauson et al. |
| 2019/0183679 A1 | 6/2019 | Sawicz |
| 2019/0183681 A1 | 6/2019 | Schaller et al. |
| 2019/0254872 A1 | 8/2019 | Clauson et al. |
| 2019/0269557 A1 | 9/2019 | Clauson et al. |
| 2019/0282402 A1 | 9/2019 | Clauson et al. |
| 2019/0321223 A1 | 10/2019 | Chamness et al. |
| 2019/0365567 A1 | 12/2019 | Balkenbush et al. |
| 2019/0388272 A1 | 12/2019 | Clauson et al. |
| 2020/0016001 A1 | 1/2020 | McDonell et al. |
| 2020/0022841 A1 | 1/2020 | Chamness et al. |
| 2020/0060875 A1 | 2/2020 | Clauson et al. |
| 2020/0197222 A1 | 6/2020 | Clauson et al. |
| 2020/0289319 A1 | 9/2020 | Carter et al. |
| 2020/0352784 A1 | 11/2020 | Kahook et al. |
| 2020/0360185 A1 | 11/2020 | Carter et al. |

(56) References Cited

U.S. PATENT DOCUMENTS

| | | |
|---|---|---|
| 2021/0100937 A1 | 4/2021 | Bourne et al. |
| 2022/0151831 A1 | 5/2022 | Peterson |
| 2022/0233353 A1 | 7/2022 | Carter et al. |

FOREIGN PATENT DOCUMENTS

| | | |
|---|---|---|
| CN | 103671079 A | 3/2014 |
| CN | 108024854 A | 5/2018 |
| DE | 10 2007 031722 A1 | 1/2009 |
| DE | 102007040290 B4 | 7/2019 |
| EP | 1832259 B1 | 6/2009 |
| EP | 1556099 B1 | 7/2013 |
| EP | 2168540 B1 | 4/2015 |
| EP | 2 094 173 B1 | 3/2016 |
| EP | 1735030 B1 | 8/2016 |
| EP | 2 892 438 B1 | 10/2018 |
| GB | 1304324 A | 1/1973 |
| GB | 2018601 A | 10/1979 |
| JP | H0779826 B2 | 8/1995 |
| JP | 2018035761 A | 3/2018 |
| JP | 6654763 B2 | 2/2020 |
| SU | 728852 A1 | 4/1980 |
| WO | WO-2006/119557 A1 | 11/2006 |
| WO | WO-2013/039742 A2 | 3/2013 |
| WO | WO-2014/039093 A1 | 3/2014 |
| WO | WO-2015/161149 A1 | 10/2015 |
| WO | WO-2018/081295 A1 | 5/2018 |
| WO | WO-2018/217579 A1 | 11/2018 |

OTHER PUBLICATIONS

U.S. Appl. No. 15/970,439, filed May 3, 2018, US 2018-0318132.
U.S. Appl. No. 16/221,239, filed Dec. 14, 2018, US 2019-0183681.
U.S. Appl. No. 16/257,533, filed Jan. 25, 2019, US 2019-0151149.
U.S. Appl. No. 16/345,182, filed Apr. 25, 2019, US 2019-0282402.
PCT/US2019/35442, Jun.4, 2019, WO 2019/236615.
PCT/US2020/16155, Jan. 31, 2020, WO 2020/160434.
U.S. Appl. No. 16/404,252, filed May 6, 2019, US 2019-0254872.
U.S. Appl. No. 16/431,560, filed Jun. 4, 2019, US 2019-0365567.
U.S. Appl. No. 16/436,648, filed Jun. 10, 2019, US 2019-0321223.
U.S. Appl. No. 16/577,418, filed Sep. 20, 2019, US 2020-0022841.
U.S. Appl. No. 16/667,030, filed Oct. 29, 2019, US 2020-0060875.
U.S. Appl. No. 16/690,881, filed Nov. 21, 2019, US 2020-0197222.
U.S. Appl. No. 16/811,786, filed Mar. 6, 2020, US 2020-0306083.
U.S. Appl. No. 16/875,426, filed May 15, 2020, US 2020-0360185.
U.S. Appl. No. 17/177,017, filed Feb. 16, 2021, US 2021-0161712.
U.S. Appl. No. 17/570,094, filed Jan. 6, 2022, US 2022-0233353.

\* cited by examiner

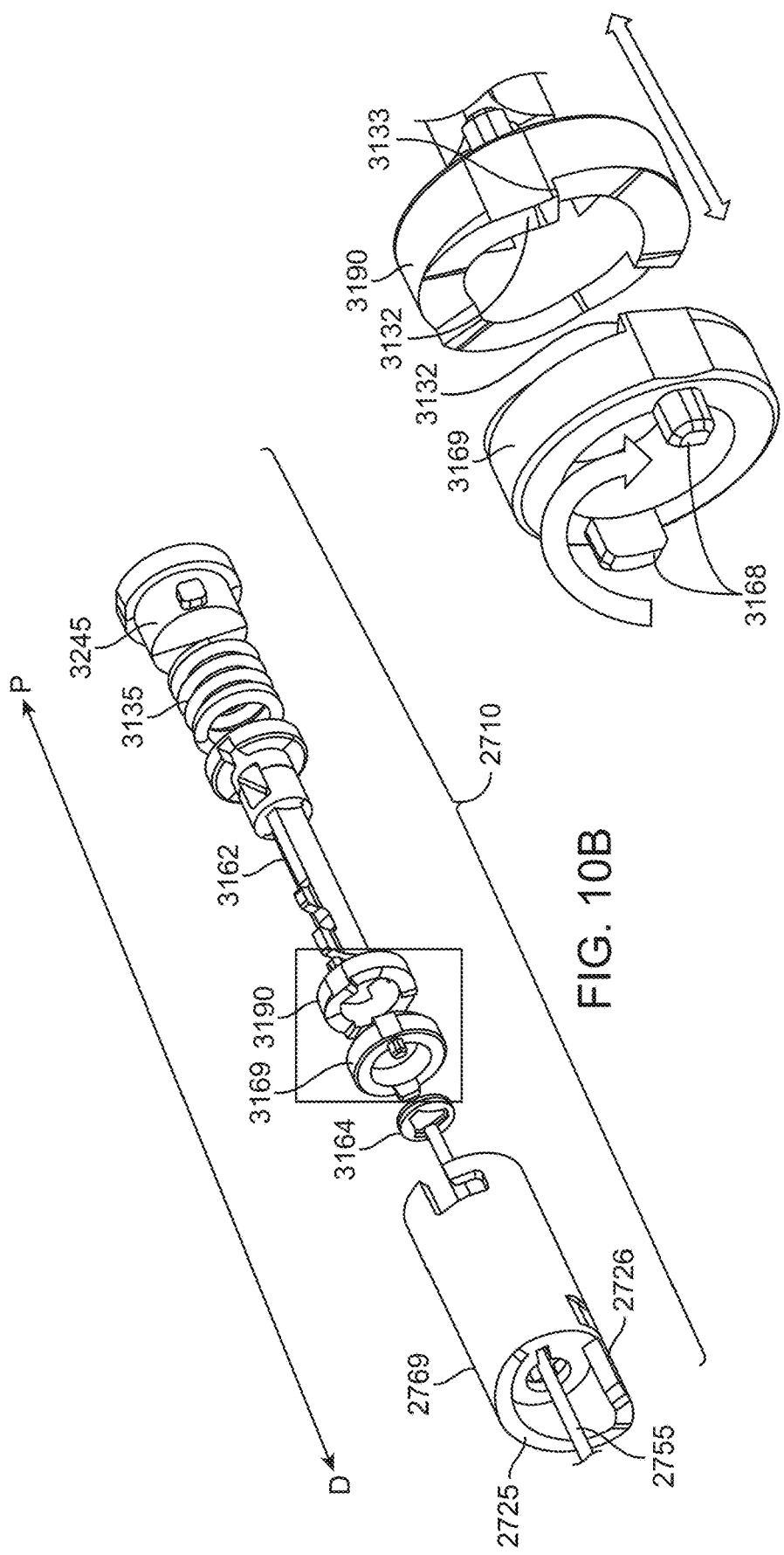

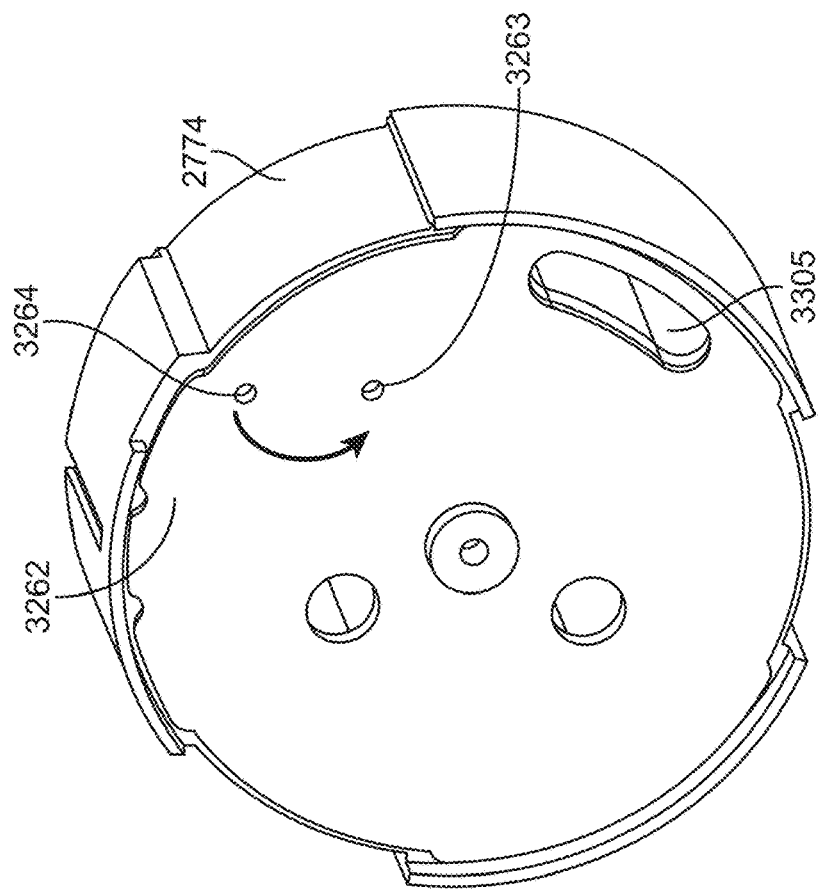
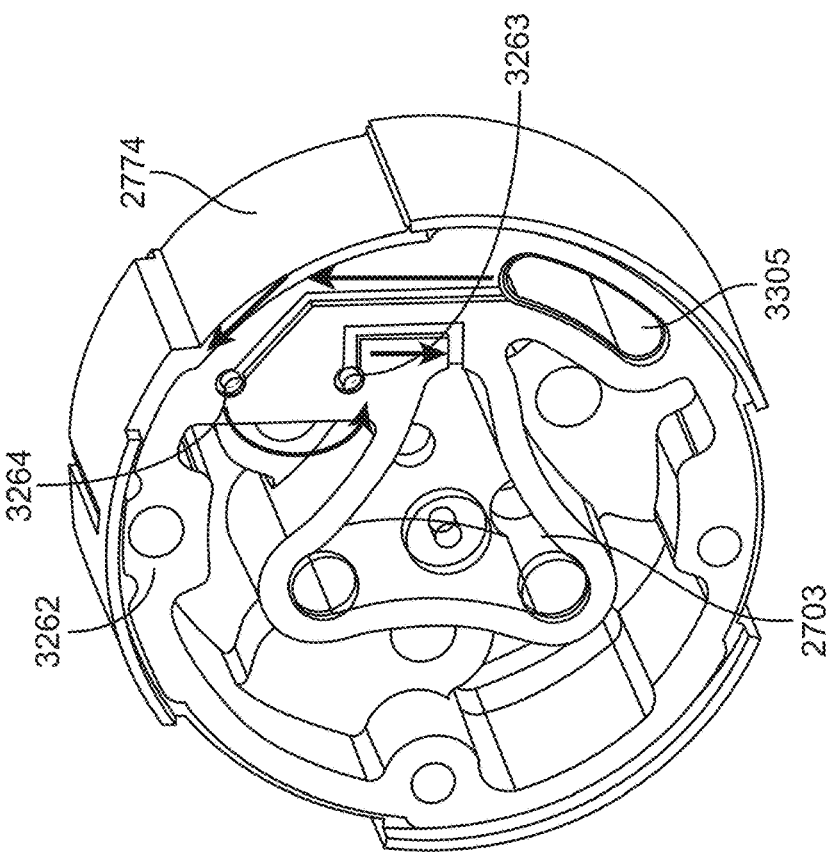
FIG. 12D
FIG. 12C

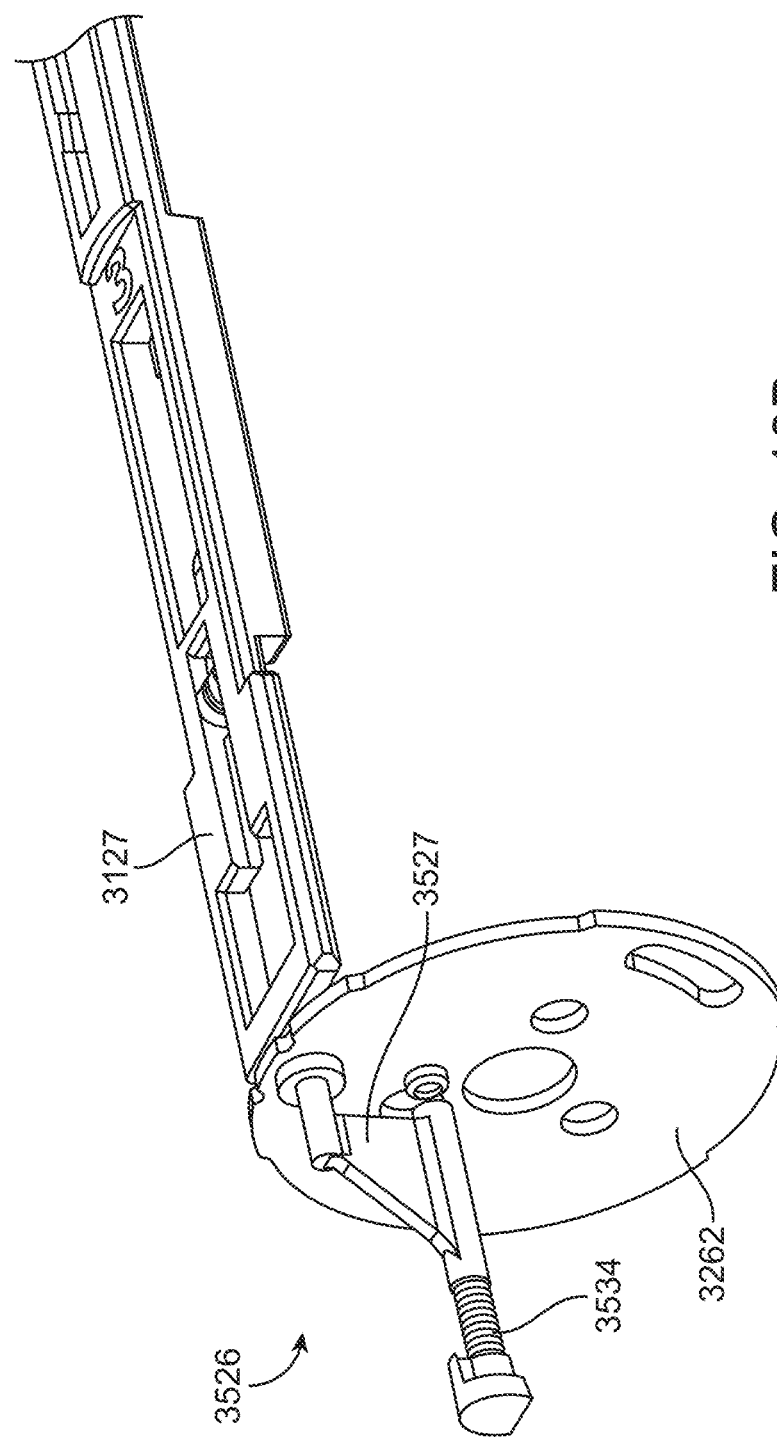

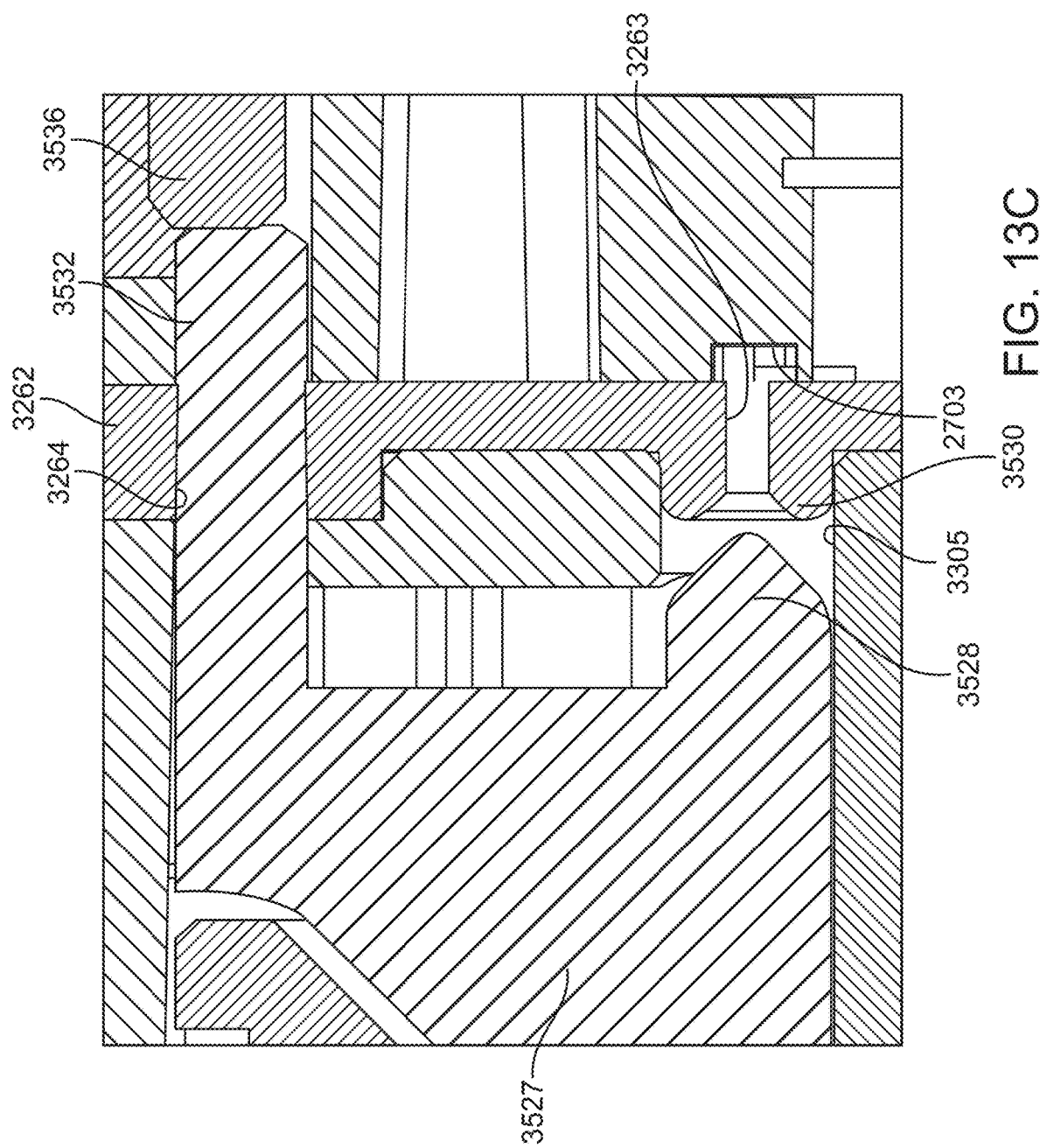

MULTI-STAGE TRIGGER FOR OPHTHALMOLOGY CUTTING TOOL

CROSS-REFERENCE TO RELATED APPLICATIONS

This application claims the benefit of priority under 35 U.S.C. § 119(e) to U.S. Provisional Patent Application Ser. No. 62/858,785, filed Jun. 7, 2019. The disclosure of the provisional application is hereby incorporated by reference in its entirety.

FIELD

The present technology relates generally to ophthalmic microsurgical tools and systems, in particular, multi-stage triggers for ophthalmic microsurgical tools and systems having integrated pumping and fluid management systems.

BACKGROUND

Certain types of conventional ophthalmic surgery require breaking up lenticular tissue and intraocular objects, such as the intraocular lens or vitreous so that they can be extracted from the eye. For example, extraction of lenses for cataract surgery is one of the most common surgical procedures with more than 3 million cases performed annually in the United States alone. During cataract surgery, a commonly used method for lens extraction is phacoemulsification, which uses ultrasonic energy to emulsify the lens and aspiration to remove the lens emulsate from the eye. Other methods of lens fragmentation and extraction may include the use of instruments such as hooks, knives, or lasers to fragment the lens into pieces small enough to be extracted through an incision in the cornea in an ab interno approach. Intraocular, ab interno fragmentation of the lenticular tissue is important in cataract surgery in order to allow removal of cataracts from ocular incisions that are typically not exceeding 2.8-3.0 mm.

Typical phacoemulsification systems include a console in operative communication with a phacoemulsification hand piece that provides the control of the electronics of the hand piece, aspiration, and irrigation. During typical phacoemulsification procedures, the phaco tip is inserted into the anterior segment of the eye through a small incision in the cornea. The phaco tip is brought into contact with the lens of the eye so that the oscillating phaco tip emulsifies the lens. The emulsate is then aspirated through the lumen of the phaco tip.

A challenge associated with conventional phaco devices and other devices using a remote vacuum source is that the suction lines are quite long and flexible contributing to the fluidic system compliance. Long, compliant suction lines containing compressible material affects the responsive times at the tip when suction is turned on and off. These remote pumps suffer from post-occlusion surge.

SUMMARY

According to a first aspect, disclosed is a medical device for removing lens tissue from inside a capsular bag of an eye. The device includes a housing sized to be held in a hand and a shaft extending distally from and configured to oscillate relative to the housing. The shaft includes a distal end region adapted to access a lens inside the capsular bag of the eye and having a lumen. The device includes a cam assembly operatively coupled to a vacuum generation source positioned within the housing. The cam assembly includes a first portion operatively coupled to the vacuum generation source and a second portion operatively coupled to the first portion and to the shaft. The first portion is capable of rotating about an axis to cause the vacuum generation source to generate vacuum through the lumen. The second portion is capable of rotating about the axis with the first portion to cause the shaft to oscillate. The device includes a trigger on the housing configured to activate rotation of the cam assembly. A first degree of actuation of the trigger causes the vacuum generation source to generate vacuum within the lumen of the shaft, and a second degree of actuation of the trigger causes the shaft to oscillate as the second portion rotates.

The trigger can have a total travel path relative to the housing. Movement of the trigger a first amount as a percentage of the total travel path that is greater than 0, but less than a lower threshold percent of the total travel path can cause a valve to open in an irrigation inflow line to initiate flow of irrigation fluid from an irrigation source towards the lumen of the shaft. Movement of the trigger a first amount as a percentage of the total travel path that is greater than a lower threshold percent of the total travel path, but less than an upper threshold percent of the total travel path can cause the first portion of the cam assembly to rotate to generate vacuum through the lumen of the shaft that is continuous. Movement of the trigger a second amount as a percentage of the total travel path that is equal to or greater than the upper threshold percent of the total travel path can initiate pulsatile vacuum and oscillation of the shaft. The first amount can place the medical device in an initial irrigation-only phase. The first amount can place the medical device in an irrigation-plus-low flow continuous aspiration phase. The second amount can place the medical device in an irrigation-plus-pulsed aspiration-plus-cutting phase.

A flow rate of the vacuum generation source in the irrigation-plus-low flow continuation aspiration phase can be between about 2 mL/minute to 20 mL/minute. A flow rate of the vacuum generation source in the irrigation-plus-pulsed aspiration-plus-cutting phase can be between 20 mL/minute and 50 mL/minute. The lower threshold percent can be about 5%, and the upper threshold percent can be about 50%. A frequency of mechanical oscillation of the shaft can increase as the trigger travels greater than the upper threshold percent.

The vacuum generation source can include a plurality of pistons, each of the plurality of pistons being housed within a respective cylinder, each of the cylinders fluidly coupled to the lumen of the shaft. The trigger can be operatively coupled to a latch and a piston stop. The latch can be configured to prevent the shaft from oscillating as the second portion rotates. The piston stop can be configured to limit proximal travel of the plurality of pistons within the respective cylinders. The second degree of actuation of the trigger can simultaneously release the latch and rotates the piston stop away from the plurality of pistons initiation shaft oscillation and pulsatile vacuum.

The trigger can be operatively coupled to a latch configured to prevent the shaft from oscillating as the second portion rotates. The second degree of actuation of the trigger can release the latch allowing the shaft to oscillate as the second portion rotates. A proximal end of the shaft can be coupled to a cutter holder having a distal-facing surface, a proximal-facing surface, and an upper surface, the upper surface defining a notch sized to receive the latch. The device can further include a cutter spline configured to abut against the proximal-facing surface of the cutter holder, the cutter spline coupled to the second portion of the cam assembly. The trigger can have a resting position, the latch is engaged within the notch when the trigger is in the resting position. The first degree of actuation of the trigger can move the trigger from the resting position into an aspiration-only position. The latch can remain engaged within the notch when the trigger is in the aspiration-only position. The second degree of actuation of the trigger can move the trigger from the aspiration-only position into an aspiration-oscillation position. The latch can be removed from the notch when the trigger is in the aspiration-oscillation position. When the latch is engaged within the notch of the cutter holder, the cutter holder and the shaft can remain stationary during rotation of the second portion. When the latch is withdrawn from the notch of the cutter holder, the cutter spline, the cutter holder, and the shaft can be configured to oscillate together during rotation of the second portion.

The first degree of actuation of the trigger can slide a button rod proximally along a longitudinal axis of the housing. The button rod can include a ramp configured to engage with the latch causing the latch to slide along the ramp and lift out of engagement with the notch releasing the cutter holder. The cutter holder and the shaft can be urged by the cutter spline in a distal direction. The cutter holder and the shaft can be urged in a proximal direction by a cutter holder spring. Rotation of the second portion of the cam assembly can urge a cam follower in a proximal direction compressing a cam follower spring. The shaft can retract in the proximal direction with the cam follower. The cam follower can drop distally at a point in the rotation and the cam follower spring urges the shaft in a distal direction. The cutter spline can move with the cam follower. The cutter holder can move with the cutter spline when the latch is withdrawn from the notch. The cutter holder can remain stationary as the cutter spline moves when the latch is engaged within the notch.

The shaft can oscillate by reciprocating along a longitudinal axis. The shaft can reciprocate in a distal direction with a first maximum speed, and reciprocate in a proximal direction with a second maximum speed. The first maximum speed can be greater than the second maximum speed. The longitudinal axis can be coincident with the axis about which the cam assembly rotates. The first portion of the cam assembly can include a first surface. The vacuum generation source can include a piston and a cylinder. Rotation of the first surface can cause the piston to reciprocate within the cylinder to generate vacuum. The vacuum generation source can include a plurality of vacuum generation sources, and the rotation of the first portion of the cam assembly can cause each of the plurality of vacuum generation sources to generate vacuum. The cam assembly can be operatively rotated by a motor positioned within an interior of the housing containing the cam assembly. A speed of the motor can be variably controlled by the trigger on the housing.

The vacuum generation source can include a plurality of pistons, each of the plurality of pistons being housed within a respective cylinder, each of the cylinders fluidly coupled to the lumen of the shaft. The first portion of the cam assembly can be capable of being rotated by a motor via a rotatable coupler. Rotation of the first portion of the cam assembly can cause the plurality of pistons to generate a discontinuous pulsatile aspiration within the lumen. The medical device can further include a piston stop movably coupled to the trigger. The piston stop can be configured to limit proximal travel of the plurality of pistons within the respective cylinders. The piston stop can maintain the vacuum generation source in a low flow continuous aspiration mode during rotation of the first portion of the cam assembly. The piston stop can limit proximal travel of each piston within its respective cylinder to less than a maximum proximal travel to maintain the low flow continuous aspiration mode. The second degree of actuation of the trigger can move the piston stop relative to the plurality of pistons switching the vacuum generation source to a discontinuous pulsatile aspiration mode. The discontinuous pulsatile aspiration mode can allow for maximum proximal travel of each piston within its respective cylinder. The piston stop can rotate around a longitudinal axis of the housing upon the second degree of actuation. A flow rate of the continuous aspiration can be less than a flow rate of the discontinuous pulsatile aspiration. The flow rate of the continuous aspiration can be between about 2 mL/minute to about 20 mL/minute. The flow rate of the discontinuous pulsatile aspiration can be about 20 mL/minute to about 50 mL/minute.

The medical device can be configured to fluidly couple to a fluid system having a source of irrigation fluid, the medical device fluidly coupled via an irrigation line. The irrigation line can include a valve configured to control irrigation fluid flow through the irrigation line. The first degree of actuation of the trigger can additionally open the valve of the irrigation line of the fluid system and put the medical device into an irrigation-plus-low flow continuous aspiration phase. The second degree of actuation of the trigger can put the medical device into an irrigation-plus-pulsed aspiration-plus cutting phase. Actuation of the trigger beyond the second degree can increase at least one of an oscillation frequency and an aspiration flow rate.

In some variations, one or more of the following can optionally be included in any feasible combination in the above methods, apparatus, devices, and systems. More details of the devices, systems, apparatus, and methods are set forth in the accompanying drawings and the description below. Other features and advantages will be apparent from the description and drawings.

BRIEF DESCRIPTION OF THE DRAWINGS

These and other aspects will now be described in detail with reference to the following drawings. Generally speaking, the figures are not to scale in absolute terms or comparatively, but are intended to be illustrative. Also, relative placement of features and elements may be modified for the purpose of illustrative clarity.

FIGS. 10A, 10B, and 10C illustrate an implementation of a cam assembly.

FIGS. 12C-12D illustrate a vacuum manifold covered by a gasket incorporating the venting mechanism of FIGS. 12A-12B from a distal end perspective.

FIG. 13B is a perspective partial view of the venting mechanism of FIG. 13A.

FIGS. 13C and 13D are cross-sectional view of the venting mechanism of FIG. 13A in an open and closed position, respectively.

Figure 1A:
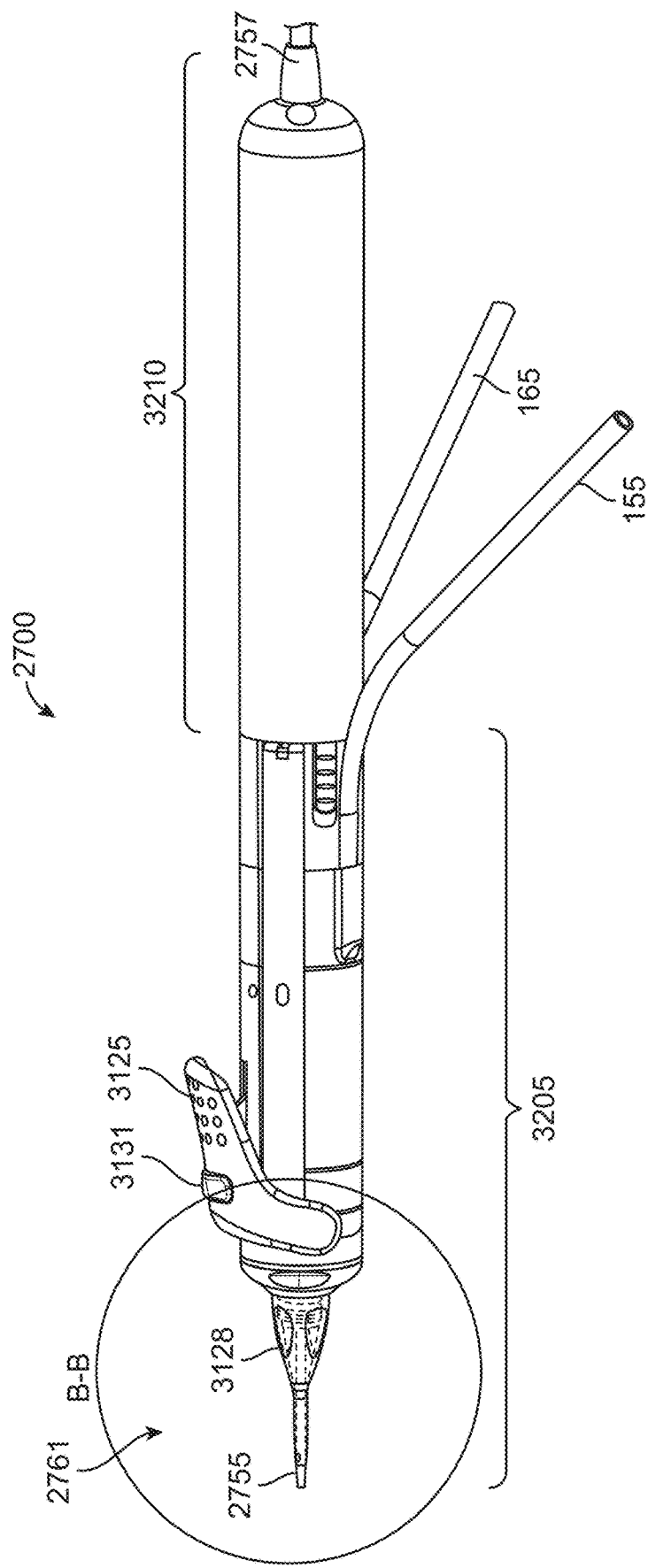
FIG. 1A shows a perspective view of a microsurgical tool having an elongate member.

It should be appreciated that the drawings are for example only and are not meant to be to scale. It is to be understood that devices described herein may include features not necessarily depicted in each figure.

DETAILED DESCRIPTION

Described herein are systems, devices, and methods useful for intraocular fragmentation and removal of the lens, vitreous, and other tissues during intraocular surgery. The various systems, devices, and methods are configured to perform one or more functions useful in ophthalmic procedures including, but not limited to, cutting, fragmentation, emulsification, aspiration, and/or irrigation of material present at a target location during a procedure in the eye. The systems, devices, and methods described herein are configured to apply vacuum and deliver fluids to maintain a pressure balance within the eye. The systems, devices, and methods described herein that apply vacuum and/or deliver fluids may also be configured to cut, fragment, emulsify, or otherwise make smaller material in and near the surgical site. The systems, devices, and methods described herein that allow for vacuum to be applied can provide that vacuum using pulsed vacuum with or without interspersed pulsed positive pressure to provide momentary retrograde flow.

"Material" as used herein can include fluids (from the eye or provided to the eye), tissues, or fragments of tissues such as lenticular tissue, vitreous, cells, and any other fluid or tissue or other material that may be present during a procedure in the eye (e.g. cataract procedure, vitrectomy procedures, and the like).

The various features and functions of the devices described herein may be applied to one or more devices described herein even though they may not be expressly described in combination. It should also be appreciated that various features and functions of the devices described herein can be applied to conventional devices and systems known in the art also useful for cutting, fragmenting, emulsifying, or otherwise impacting tissues at or near a surgical site, including, but not limited to phacoemulsification systems, vitrectomy systems, bag polishing systems, and other tools useful in performing cataract surgeries or vitrectomy surgery, and the like. Where a feature is described in the context of a lens fragmentation device, for example, it should be appreciated that the same feature may also be incorporated into an instrument useful for vitrectomy.

Any of a number of microsurgical instruments are considered herein, including vitrectomy cutters, phacoemulsification or phacofragmentation hand-pieces, electric microscissors, fiber optic illumination instruments, coagulation hand-pieces, and other microsurgical instrument. In some implementations, the instrument is one or more of those described in U.S. Patent publication No. 2018/0318132, filed May 3, 2018, which is incorporated by reference herein in its entirety.

The instrument is sometimes referred to herein as a "device" or "tool" or "peripheral device" or "hand piece" or "hand held unit". Use of the term "hand piece" herein can include a hand piece coupled to a robotic arm or robotic system or other computer-assisted surgical system in which the user uses a computer console to manipulate the controls of the instrument. The computer can translate the user's movements and actuation of the controls to be then carried out on the patient by the robotic arm.

FIGS. 1A-1B and FIGS. 2A-2B show implementations of an ophthalmic microsurgical instrument 2700 for use by a surgeon in performing various ophthalmic surgical procedures. The instrument is particularly useful for cataract surgery.

Cataracts are typically classified based on severity on a scale of 1 to 5. The microsurgical instruments described herein require less energy, time, and fluid to remove the tissues from the eye compared to, for example, conventional phacoemulsification hand pieces, particularly for use for cataracts in a range of 1 to 3. In some implementations, the microsurgical instruments described herein can be useful for harder cataracts above 3 to about 4 on the hardness scale as well. The microsurgical instruments described herein can be all in one and configured to create small lens fragments in situ and aspirated with little to no phacoemulsification.

The microsurgical instrument 2700 can include a suction or vacuum source, such as an integrated aspiration pump, that is found within an interior of the device 2700 positioned near the distal cutting tip. Thus, the device 2700 can be a fully hand-held device capable of being used independently of a remote microsurgical system, for example, a system providing irrigation fluid or aspiration support via a separate, remote pump. The microsurgical instruments 2700 described herein can be all-in-one devices in which the only linkage to a remote system may be for power. The device 2700 can be operatively coupled to the remote system such as via a cable 2757. The cable 2757 may also be configured to connect the device 2700 to a wall socket. The device 2700 can also be powered by one or more batteries. The all-in-one devices may not have any foot pedal or other linkage for control. The microsurgical instruments 2700 can rely solely on the vacuum source within the housing of the device and an integrated power source, such as an internal battery.

The operating parameters can differ according to, for example, the particular procedure being performed, the different stages of the procedure, the surgeon's personal preferences, whether the procedure is being performed in the anterior or posterior portion of the patient's eye, and so on. Where features are described with respect to one implementation of the instrument, it should be appreciated that the same feature may be present on another implementation of the instrument even though the feature may not be explicitly described with respect to that implementation.

Again, with respect to FIGS. 1A-1B, and 2A-2B illustrate an implementation of a microsurgical instrument 2700. The device 2700 includes a distal, elongate member or shaft 2761 coupled to and extending longitudinally from a housing of the device 2700. At least a distal end region of the shaft 2761 is configured to be inserted into the eye in a minimally invasive manner to cut, aspirate, and/or inject material in the eye, such as during a cataract procedure. At least a portion of the shaft 2761 can be configured to oscillate or slide reciprocally relative to the housing in order to remove lens or other tissues of the eye. The shaft 2761 can include an oscillating elongate member 2755 extending through an outer protective sleeve 2759 (see also FIGS. 3A-3B). The outer protective sleeve 2759 can be stationary and thereby protect the corneal incision or other tissues through which the shaft 2761 extends from being impacted by oscillating movements of the elongate member 2755. The shaft 2761 can also include a single tubular elongate member 2755 that oscillates without any outer sleeve 2759. However, it is preferable the shaft 2761 include a protective sleeve surrounding at least a portion of the oscillating elongate member 2755, for example, to protect the cornea from tissue damage due to being exposed to the oscillating movements of the elongate member 2755.

As used herein, "oscillate" or "oscillating movements" can include any periodic, repetitive movement that occurs according to a pattern and need not be sinusoidal. The oscillating movement can include reciprocating sliding movements that occur in a back and forth manner relative to the hand piece. The oscillating movement can include repeatedly advancing and retracting the elongate member along its longitudinal axis. The repeated advancing and retracting may occur along the longitudinal axis, but the path the oscillating movements take need not be linear. The path of movement can occur non-linearly (i.e. away from the longitudinal axis during at least a portion of the movement) along an elliptical pathway or a curvilinear pathway or a slight side-to-side motion in combination with a back-and-forth motion. In an implementation, the shaft 2761 can incorporate a feature configured to impart a moment to the shaft 2761 upon reaching maximum distal extension causing motion in a side-to-side manner along with the axial oscillation. Side-to-side motion can shear lens tissue to reduce the size of fragments for aspiration through the lumen thereby reducing the propensity for clogging. The path of movement can be rotational, orbital, or torsional around the longitudinal axis of the device or other type of movement relative to the longitudinal axis of the device including three-dimensional movements in which the elongate member moves back and forth as well as from side-to-side. The oscillating movements include profiles of repetitive patterns that may change depending on where in the cycle of oscillation the movement occurs. The oscillating movements can be asymmetric in profile, as will be described in more detail below.

The shaft 2761, which may be referred to herein as "cutter" or "cutter tube" or "elongate member" can be configured for different techniques, including phacoemulsification, vitrectomy, bag polishing, or other technique. At least a portion of the shaft 2761 can include a tubular, oscillating elongate member having an internal lumen extending through it such that fluids can be delivered and/or aspirated through the oscillating elongate member. The distal end of the shaft 2761 can define an opening into the lumen. The shaft can be configured to oscillate in order to jackhammer lens tissue and aspirate it out of the eye similar to conventional phacoemulsification cutting tips. The shaft 2761 can be configured to perform vitrectomy and incorporate inner and outer tubes having side openings into the lumen. The inner and outer tubes can slide reciprocally with one another to chop and remove hard lens material. Any of a variety of configurations of the elongate member are considered herein. The shaft 2761 may have inner and outer members or the shaft 2761 may include only a single tubular element configured to oscillate relative to the hand piece to cut and aspirate material. Where the shaft is described as having an inner elongate member coaxially arranged within an outer tubular member, the inner elongate member can be a solid rod and need not include an inner lumen. The oscillating elongate member need not be tubular, but instead can be formed as a solid element. In some implementations, the elongate member has a sharpened cutting tip or bevel, which can include a needle tip. The elongate member can include a cutting element having a sharpened needle tip and can be a solid element extending through an outer tubular member and aspiration forces applied through the lumen of the outer tubular member such that fluids and tissues are drawn into an annular gap extending between the inner and outer members. The elongate member can have an inner lumen and distal edge configured to cut tissue. The distal edge can be sharpened while the opening into the tube can be cut at an angle to the elongate axis of the elongate member or perpendicular to the elongate axis of the elongate member. The inner lumen of the elongate member can be configured to aspirate material therethrough, such as ocular lens material, lens fragments, vitreous, and/or fluids from the eye. Thus, aspiration forces can be applied through the inner lumen of the elongate member. However, aspiration forces can also be applied through a lumen of a tubular outer member extending over the elongate member such that aspiration occurs through the annular space between the two in order to receive and/or deliver fluids to the treatment site. In such a configuration, the gap between the tubular outer member and the inner member can vary, for example, between about 0.001" to about 0.100". In some implementations, the aspiration forces can be applied through both the inner elongate member having a lumen and the lumen through the outer tubular member.

Again with respect to FIGS. 1A-1B, FIGS. 2A-2B, the housing of the device 2700 can be formed of a relatively rigid, lightweight material(s). The housing can include a disposable portion 3205 configured to be releasably coupled to a durable, reusable portion 3210. The reusable portion 3210 may be re-sterilized and reused. It should be appreciated that the reusable portion 3210 may also be disposable and manufactured by lower cost materials such that it is financially feasible for the portion 3210 also to be disposed of after use. The disposable portion 3205 generally includes components of the device 2700 configured to come into direct contact with fluids and materials from the eye, for example the elongate member 2755 including the distal cutting tip, irrigation sleeve 3128, irrigation inflow line 155, waste outflow line 165, connection sites for the irrigation inflow line 155 and waste outflow line 165, etc. The disposable portion 3205 can also include the aspiration pump such as a piston pump having a plurality of pistons housed within corresponding piston cylinders. The reusable portion 3210 generally includes the components of the device 2700 that are configured to remain outside the fluid path, for example the components configured to drive the aspiration pump and/or the cutting elements. The reusable portion 3210 may include the motor, the actuator for actuating the motor, the motor coupler, and other drive components. A rotating cam assembly 2710 (see FIGS. 10A-10B) capable of being rotated by a motor via a motor coupler, which will be described in more detail below, can be positioned within the disposable portion 3205 or the reusable portion 3210. The disposable portion may also include one or more components of the drive mechanism for linear translation of the cutter.

A single reusable driver portion 3210 can be configured to operatively couple with one or more disposable working portions 3205 in an interchangeable manner. The disposable working portions 3205 can be configured for different types of procedures including lens fragmentation, emulsification, vitrectomy, bag polishing, aspiration, irrigation, coagulation, illumination, visualization, IOL insertion, and others. The disposable working portions 3205 therefore may be used for any of a variety of procedures including vitrectomy, phacoemulsification, intraocular lens insertion, etc. The operating parameters of the instrument can differ according to, for example, the disposable working portion 3205 attached to the reusable driver portion 3210 and/or the particular procedure being performed, the different stages of the procedure, the surgeon's personal preferences, whether the procedure is being performed in the anterior or posterior portion of the patient's eye, and so on. The components of the working portion 3205 can vary depending on the type of procedure and each of the different working portions 3205 regardless the procedure it is configured to perform can operatively couple and be operated by a single reusable driver portion 3210. The different disposable working portions 3205 will be described in more detail below.

The two housing portions 3205, 3210 can couple together using a variety of mechanisms such as threads, snap-lock, bayonet, and the like. The coupling mechanism can include a release button configured to uncouple the two housing portions. The coupling between the disposable portion 3205 and the reusable portion 3210 may be purely mechanical or may involve both mechanical and electronic couplings. For example, the disposable portion 3205 may have an electronic input configured to electronically couple with a portion of the reusable portion 3210. Alternatively, the disposable portion 3205 may have an input configured to mechanically couple and interact with the reusable portion 3210. Coupling between the portions 3205, 3210 will be described in more detail below.

Figure 2A:
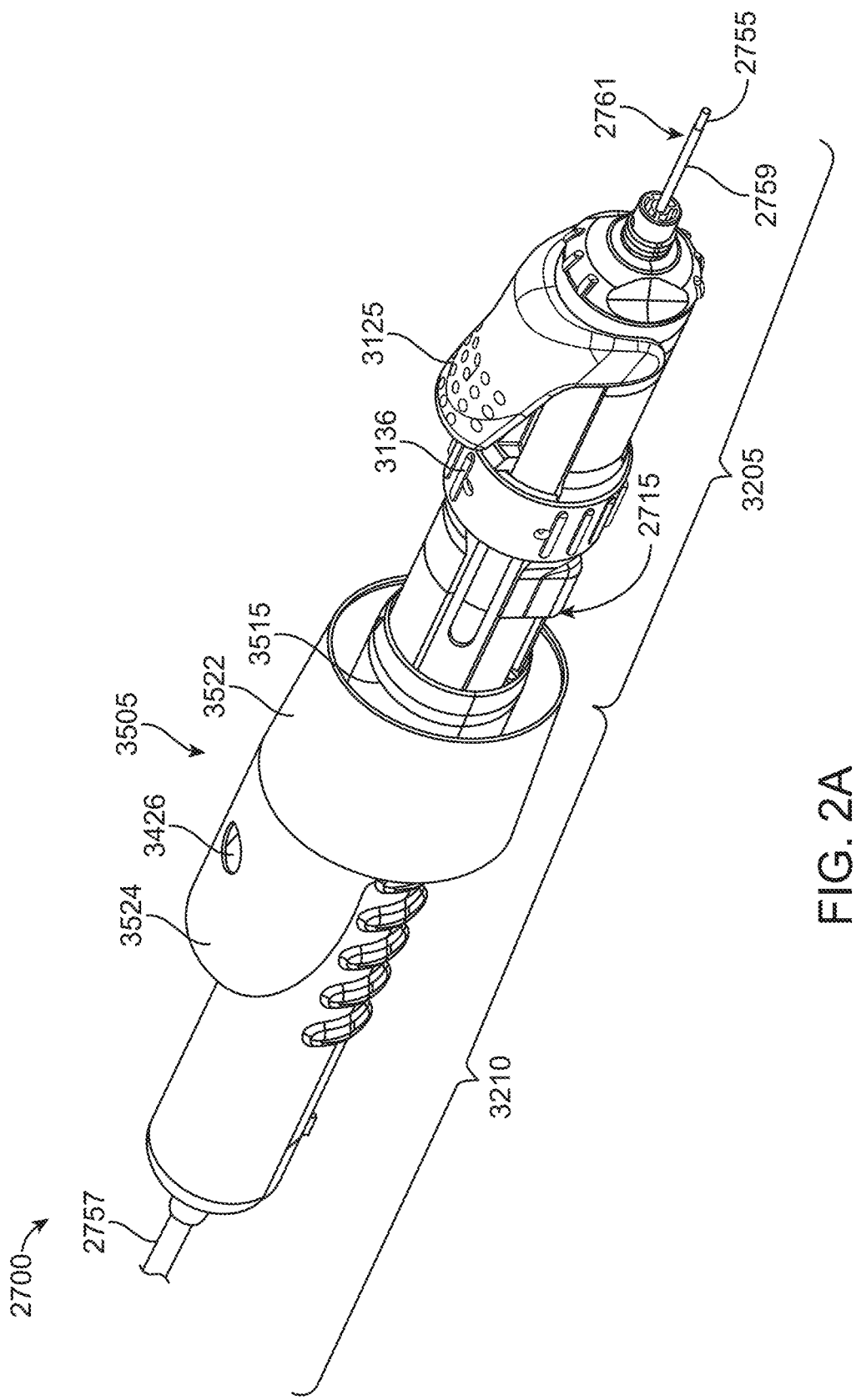
FIG. 2A shows a sterility sheath in a furled configuration positioned on a housing of an instrument.
Figure 2B:
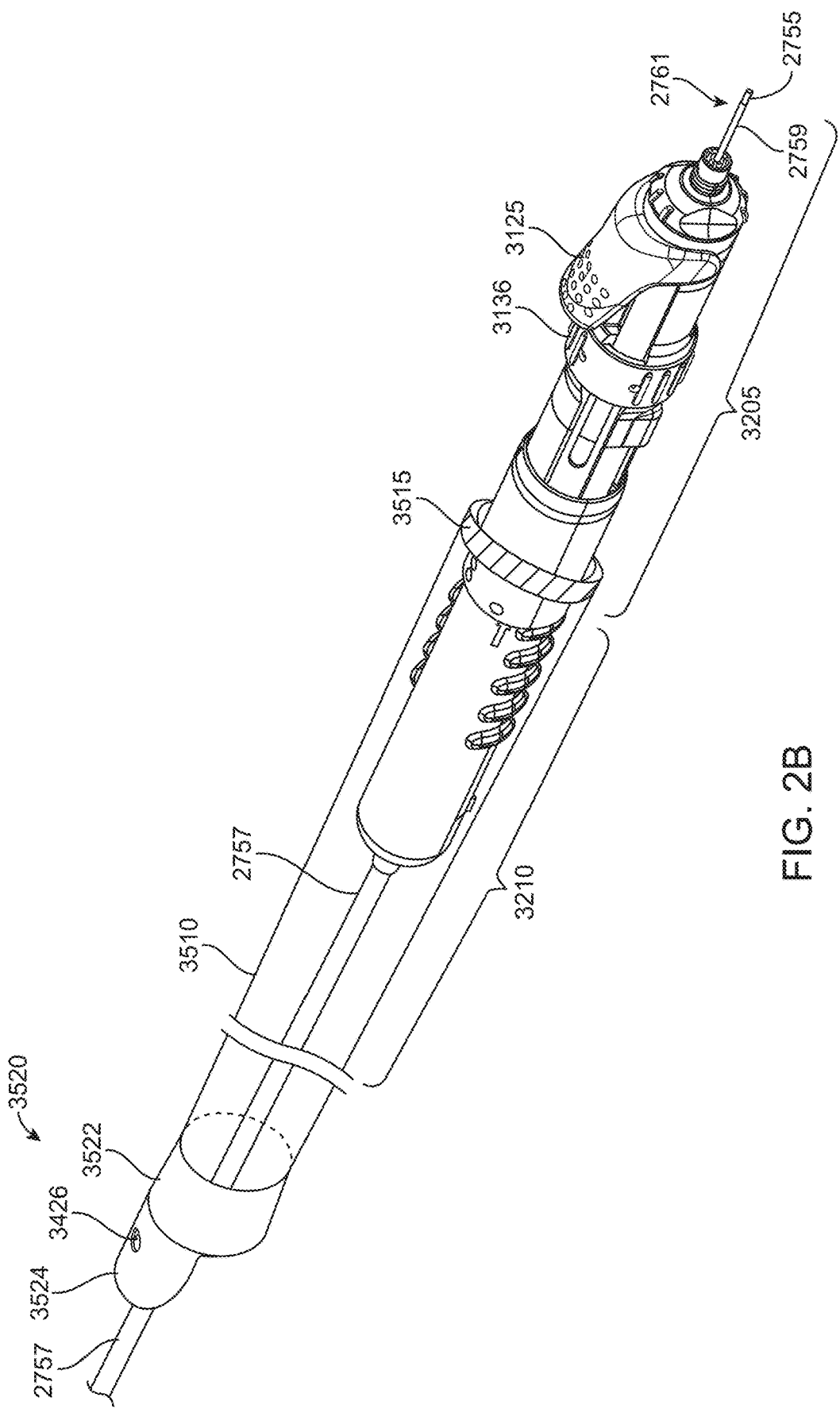
FIG. 2B shows the sterility sheath of FIG. 2A in an unfurled configuration after deployment over the housing of the instrument.

The device can incorporate a protective drape or sterility sheath configured to protect against inadvertent contamination of the sterile components of the device by the non-sterile components of the device. FIGS. 2A-2B show view of an instrument 2700 incorporating the sterility sheath 3505. The sterility sheath 3505 can include a flexible, tubular cover 3510 having a first end attached to the instrument via a coupler 3515 and a second end attached to a pull tab 3520. The coupler 3515 can be an annular element configured to couple the first end of the tubular cover 3510 to the proximal end region of the disposable portion 3205. The cover 3510 can have a furled configuration prior to deployment of the sheath 3505 (see FIG. 2A) and an unfurled configuration after deployment of the sheath 3505 (see FIG. 2B). The cover 3510 in the furled configuration can be a folded such as in an accordion pattern, rolled, or otherwise compactly encased relative to the instrument to minimize its footprint prior to use. The cover 3510 in the unfurled configuration unfolds or unrolls such that the durable portion 3210 of the instrument may be contained within the cover 3510 between the coupler 3515 and the pull tab 3520. The cover 3510 can be a flexible, tubular element configured to receive at least the durable portion 3210 of the instrument including the housing of the durable portion 3210 as well as at least a length of attachments to the durable portion 3210 such as power cable 2757 extending from the proximal region of the instrument. In some implementations, the length of the cover 3510 is from about 5 inches up to about 30 inches long. The cover 3510 can be any of a variety of materials, particularly cheap disposable materials such as plastic, fabric, or paper. The material of the cover 3510 is designed to go from a furled to an unfurled configuration without tearing or ripping and is sufficiently flexible enough to avoid impacting a user's grip on the instrument. In some implementations, the cover 3510 is a transparent or translucent plastic material such that a user may still view the housing of the instrument through the cover 3510 when in the unfurled configuration over the housing of the reusable portion 3210. The coupler 3515 can be less flexible than a material of the cover 3510. In some implementations, the coupler 3515 can be formed of a material such as cardboard, plastic, metal, or other material. The pull tab 3520 attached to the second end of the tubular cover 3510 can have an annular portion 3522 configured to surround the furled cover 3510 and capture it between an inner surface of the annular portion 3522 and an outer surface of the coupler 3515. The pull tab 3520 can also incorporate gripper portion 3524 configured to be grasped and pulled by a user to withdraw the pull tab 3520 proximally thereby causing the cover 3510 to unfurl over the durable portion 3210 of the instrument. The gripper portion 3524 of the pull tab 3520 can incorporate one or more surface features 3426 configured to improve a user's grip on the tab 3520.

The disposable portion 3205 or the durable portion 3210 of the device 2700 can include one or more inputs or actuators. The inputs on the instrument 2700 can include any of a variety of actuator, trigger, button, slider, dial, keypad, switch, touchscreen, foot pedal, footswitch, or other input that can be retracted, pressed, squeezed, slid, tapped, or otherwise actuated to activate, modify, or otherwise cause a response of the instrument 2700. In some implementations, the microsurgical instrument 2700 can be an all-in-one, fully hand-held without any foot pedal or other tethering connection linked to the instrument. The instrument 2700 can be capable of multiple functions (i.e. irrigation, aspiration, and cutting functions) all while maintaining full portability, flexibility, and freedom of movement.

The instrument 2700 can include separate inputs to activate each function of the instrument 2700 (i.e. cutting, infusion, aspiration, including continuous aspiration, pulsed vacuum, and/or pulsed vacuum with regurgitation between pulses, etc.). Preferably, the instruments 2700 described herein can achieve various functions with a single input on the housing of the instrument 2700 that can be actuated in real-time and without needing to pause during a procedure.

FIGS. 1A-1B and FIGS. 2A-2B show the instrument 2700 having an input 3125 capable of being actuated with a single finger or thumb. Because the instrument 2700 requires no foot pedal, a user can stand more comfortably and naturally (e.g. on two feet or shifting their weight from foot to foot however they please) to perform a procedure. Additionally, the vacuum can be activated with finer control due to the finger control and short compliant lines between the distal tip and the vacuum source. Finger control on the instrument 2700 allows the surgeon to activate the instrument 2700 for short periods in a manner more convenient and easier than would a foot pedal used in most conventional phacoemulsification systems. Further, since a vacuum source can be located within the housing of the device, there may be a significantly faster response time for the surgeon to activate device on and off than in other devices where the vacuum source is located only in a remote console that is several feet away and connected by long, compressible tubing. The instruments 2700 described herein have a relatively low amount of surge volume, and therefore cycling the device on and off has minimal downside. These features can allow the instruments 2700 to be activated for only brief periods when the surgeon is ready to remove lenticular tissue. This contributes to overall less irrigation fluid being removed and thus less irrigation fluid needed to be delivered.

The input 3125 can be a single, multi-stage input or trigger configured to cause different functions to occur depending on degree of actuation of the input 3125 (e.g. pressure further down on a trigger). The multi-stage activation of the input 3125 (which is referred to herein as a "trigger") can activate irrigation-only function, continuous aspiration-only function, irrigation-plus-continuous low flow aspiration function, irrigation-plus-pulsed higher flow aspiration, or irrigation-plus-pulsed higher flow aspiration-plus-cutting function of the elongate member, etc. in a seamless, real-time manner. The selection is seamless because only the single input 3125 need be actuated by a user to achieve a variety of functional modes. A first degree of actuation of the trigger can cause a vacuum generation source to generate vacuum within the lumen of the shaft and a second degree of actuation of the trigger can cause the shaft to being oscillating while vacuum continues through the lumen. A third degree of actuation of the trigger can ramp up the oscillation and/or aspiration. The actuation of the trigger along a travel path relative to the housing can initiate the one or more functions in real-time. Generally, cutting without aspiration is not desired, however, a cutting-only function is considered herein as well. As an example and not to be limiting, a user can place the input 3125 in a first position (or activate a first input) to turn on the irrigation-only function or continuous aspiration-only function. After the first input 3125 is activated, the user can then place the input 3125 (or activate a second input) in a second position to turn on the irrigation-plus-continuous aspiration function. The user can then place the input 3125 (or activate a third input) in a third position to turn on the irrigation-plus-pulsed vacuum-plus-cutting function. The user can then commence cutting while vacuum continues. The input 3125 can be urged by a user into a position that activates one or more components of the instrument 2700 to gradually ramp up. For example, the input can increase the level of aspiration and/or the frequency of oscillation of the elongate member the more the trigger is actuated. As another example, a user can place the input 3125 in a first position (or activate a first input) to turn on irrigation-plus-continuous aspiration function. The user can then place the input 3125 (or activate a second input) in a second position to turn on the irrigation-plus-pulsed vacuum-plus-cutting function. The user can then commence cutting while vacuum continues. The input 3125 can be urged by a user into a position that activates one or more components of the instrument 2700 to gradually ramp up. For example, the input can increase the level of aspiration and/or the frequency of oscillation of the elongate member the more the trigger is actuated. The multi-stage input is described in more detail below.

As mentioned, the microsurgical instrument device 2700 can include at least one suction or vacuum generation source that is found within an interior of the instrument, such as within the disposable portion 3205. Aspiration can be achieved with a variety of different pump types, including volumetric flow or positive displacement pumps (e.g. peristaltic, piston, or scroll pumps) or vacuum-based pumps (e.g., venturi or pneumatic, diaphragm, bellows, or rotary-vane pumps). For example, the integrated aspiration pump can be a piston pump within the housing of the instrument 2700. The integrated vacuum generation source can include a plurality of pistons, each of the plurality of pistons housed within a respective cylinder, each of the cylinders fluidly coupled to the lumen of the shaft. Rotation of a cam assembly via for example a motor can cause the plurality of pistons to generate a discontinuous pulsatile aspiration within the lumen of the shaft. The integrated aspiration pump can be configured to apply different levels of vacuum as well as different types of vacuum (i.e., continuous, smooth flow, semi-continuous, and/or discontinuous, pulsatile aspiration as will be discussed in more detail below. The different flow rates and flow types can also be applied by a single pump of the instrument that may be selectively activated to achieve the different aspiration types. The aspiration pump of the microsurgical instrument will be described in detail below.

Incorporating a vacuum source within the hand-held portion of the device (e.g. near the distal cutting tip) minimizes the volume of the aspiration flow path improving control and responsiveness while decreasing latency or hysteresis. Conventional phacoemulsification devices and other devices using a vacuum source remote from the hand-piece suffer from slow responsiveness and lower effective vacuum applied at the treatment site. Conventional systems have long, compliant suction lines connecting the vacuum source to the hand-piece. Compliance within a fluidic system can increase the time for suction to be transmitted from the suction source to the treatment site when the suction source is activated (and deactivated). Compliance within a fluidic system can also contribute to losses in vacuum transmitted to the treatment site resulting in the effective vacuum amount being different from the theoretical vacuum setting at the source. Additionally, the longer the fluidic lines between the vacuum source and the treatment site, the greater the friction losses, further reducing the vacuum available at the treatment site. For example, a remote vacuum source set at 600 mmHg may effectively transmit to the treatment site only 200 mmHg during some periods. The latency and hysteresis in conventional phaco devices having a remote vacuum source causes these designs to be susceptible to surges in fluid volume aspirated following a clog, particularly when the vacuum source is set at the higher flow rates. The actual surge volume in conventional systems is approximately equal to the degree of volumetric compliance in the suction line extending between the remote vacuum source and the hand-piece, which can be quite large (e.g. greater than 20 mL in some instances). This is a large surge volume to manage considering average patients have an anterior chamber volume of less than 0.3 mL. Users tend to set the vacuum source to lower levels to mitigate this increased surge volume risk associated with higher flow rates.

The devices described herein can apply greater effective vacuum at the treatment site and more rapidly respond to pressure changes, and by avoiding the line losses associated with conventional systems. The devices described herein have improved responsiveness and control even when used with the higher vacuum settings. If an occlusion occurs due to a piece of lens blocking the distal opening, the vacuum will build (e.g. up to about 500 to 600 mmHg or more). When the blockage passes breaking the seal, the surge associated with the devices described herein is significantly improved as compared to conventional devices having remote vacuum sources. For example, the surge volume of the devices described herein can be as low as about 100 cubic mm, 200 cubic mm, or no more than about 300 cubic mm, whereas conventional phacoemulsification systems can have surge volumes that can be 10×, 20×, 50×, or 100× greater than this volume. The surge volume is smaller because the devices described herein have a comparatively shorter aspiration flow path between vacuum source and target treatment site. The short aspiration flow path may also be substantially rigid or non-compliant, which further reduces the surge volume. For example, greater than 50%, 55%, 60%, 65%, 70%, 75%, 80%, 85%, 90% of the aspiration flow path of the devices described herein can be rigid resulting in no more than 10%, 15%, 20%, 25%, 30%, 35%, 40%, 45%, or 50% compliance in the aspiration flow path. The substantially non-compliant and short aspiration flow path of the devices described herein reduces the potential surge volume and also reduces the dead space that can contribute to the latency effect and lack of responsiveness.

The configuration of the vacuum source within the hand piece can vary. Preferably, the vacuum source is an aspiration pump having a small form factor such that it does not significantly affect the relative ergonomics of the hand piece. The aspiration pump in the hand piece can be selectively activated to operate in an irrigation-only mode, irrigation plus low-flow, continuous aspiration mode, and an irrigation-plus-high-flow, pulsatile aspiration mode in a seamless manner by actuation of a single trigger. Movement of the trigger along a travel path of the trigger can initiate the various modes of the device.

Figure 3A:
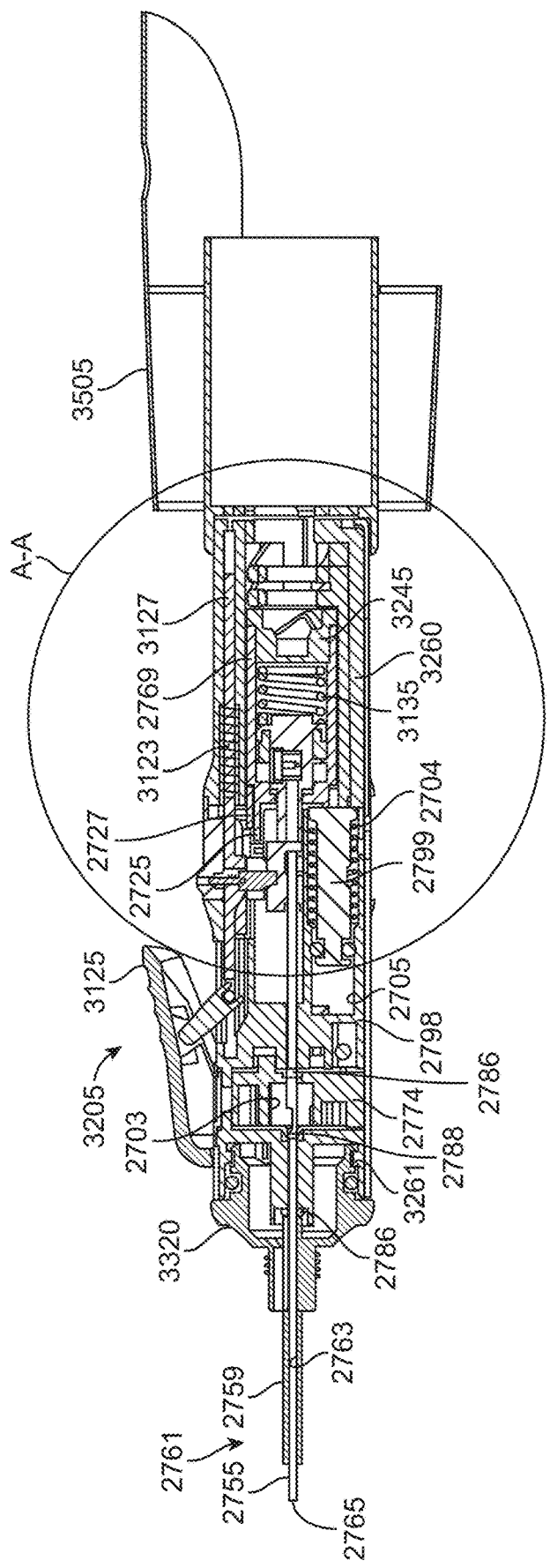
FIG. 3A is a cross-sectional view of a disposable portion 3205 of an instrument with the trigger in a resting position.
Figure 3B:
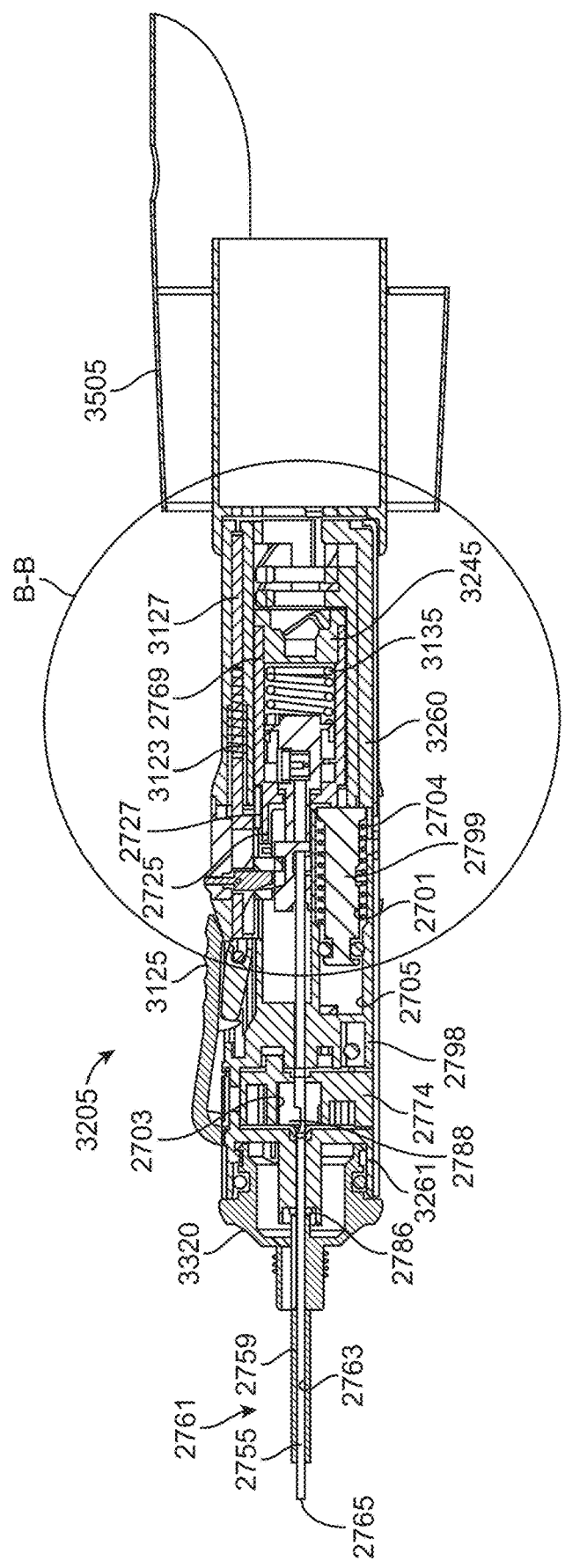
FIG. 3B is a cross-sectional view of the instrument of FIG. 3A with the trigger in a fully actuated position.

In some implementation, the vacuum source in the disposable portion 3205 can be a piston pump. FIGS. 3A-3B are a cross-sectional view of the disposable portion 3205 of the device 2700 showing a front manifold 3261 coupled to a vacuum manifold 2774, a piston manifold 2798, and a rear manifold 3260. The vacuum manifold 2774 can be coupled to the piston manifold 2798 such that a vacuum chamber 2703 of the vacuum manifold 2774 is in fluid communication with one or more pumping chambers 2705 in the piston manifold 2798. The piston manifold 2798 houses one or more reciprocating pistons 2799 movable within their respective pumping chambers 2705. The pistons 2799 are powered to move by a drive mechanism, which will be described in more detail below. The one or more pistons 2799 generate a vacuum within the pumping chambers 2705 as well as the vacuum chamber 2703 for aspiration of material through the elongate member 2755 (which may be referred to interchangeably herein as a "shaft").

FIGS. 3A-3B show the elongate member 2755 of the shaft 2761 extending through the nose cone 3320, the front manifold 3261, the vacuum manifold 2774, into the piston manifold 2798. The elongate member 2755 can define a distal opening 2765 into the lumen 2763 of the elongate member 2755 and define a proximal opening 2788 a distance away from the distal end of the elongate member 2755 out of the lumen 2763. The proximal opening 2799 can extend through a sidewall of the elongate member 2755 and be enlarged to allow for uninhibited flow out from the lumen 2763. The proximal opening 2788 of the elongate member 2755 communicates with the vacuum chamber 2703 within the vacuum manifold 2774. The proximal opening 2788 of the elongate member 2755 is maintained within this vacuum chamber 2703 even during oscillating movements of the elongate member 2755. Vacuum created within the vacuum manifold 2774 can cause the dissected tissue from the eye to be aspirated into and through the lumen 2763. The dissected tissue enters the lumen 2763 of the elongate member 2755 at the distal opening 2765 and exits the lumen 2763 of the elongate member 2755 through the proximal opening 2788 into the vacuum chamber 2703 of the vacuum manifold 2774. In other implementations, the aspiration lumen 2763 can be formed between the outer protective sleeve 2759 and the outer surface of the elongate member 2755. Lens material is not intended to travel proximal of the proximal opening 2788 in the elongate member 2755. A plurality of seals 2786, such as O-rings that provide low resistance to movement, can prevent and/or substantially reduce the passage of fluid around the shaft 2761.

The aspiration pump of the instrument 2700 can include one, two, three, or more pistons 2799 movably positioned within their respective pumping chambers 2705. Multiple pistons 2799 bouncing back and forth within their pumping chambers 2705 may create a pulsatile vacuum or full vacuum delivered to a distal portion of the lumen 2763 of the elongate member 2755 in pulses of negative pressure. The pulsatile vacuum allows for application of full vacuum through the elongate member 2755 during cutting without risk for collapse of the anterior chamber. While at the peak of the pulse, the instrument 2700 can generate a high vacuum. However, since it is pulsed, the average aspiration flow rate can be low enough for the irrigation inflow to maintain proper anterior chamber support even under these high vacuums at the pulse peak. The aspiration pump of the instrument 2700 is also configured to provide smooth, continuous vacuum that is useful in providing a low background flow, for example, to draw tissue towards the distal end of the elongate member 2755 prior to initiating cutting. This will be described in more detail below. The pulses of negative pressure can be applied also by actuation of one or more valves, such as due to movement of the one or more pistons or actuation of the valves by a computing unit.

Figure 4A:
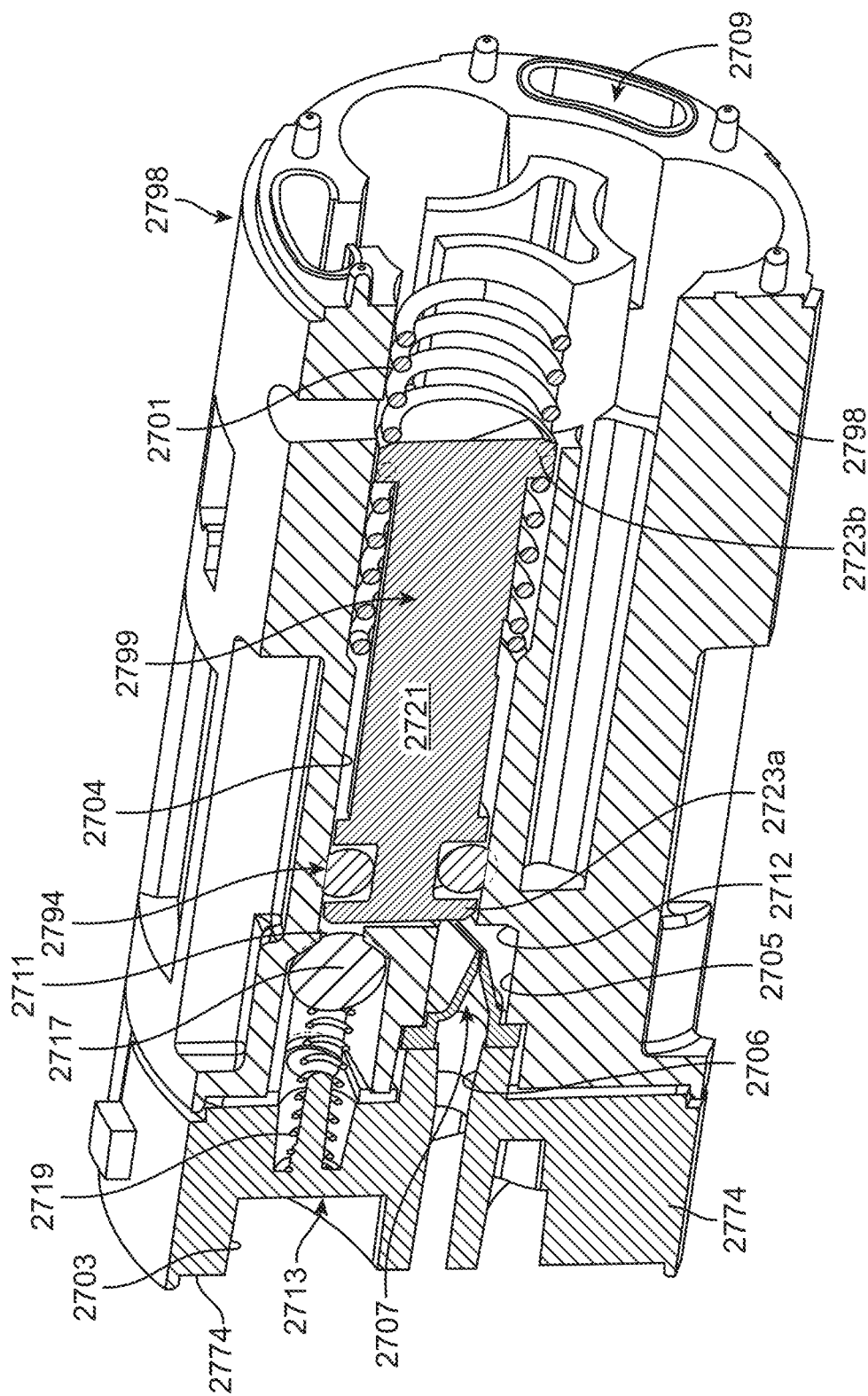
FIG. 4A is a partial, cross-sectional views of instruments illustrating a piston within a piston chamber.
Figure 4B:
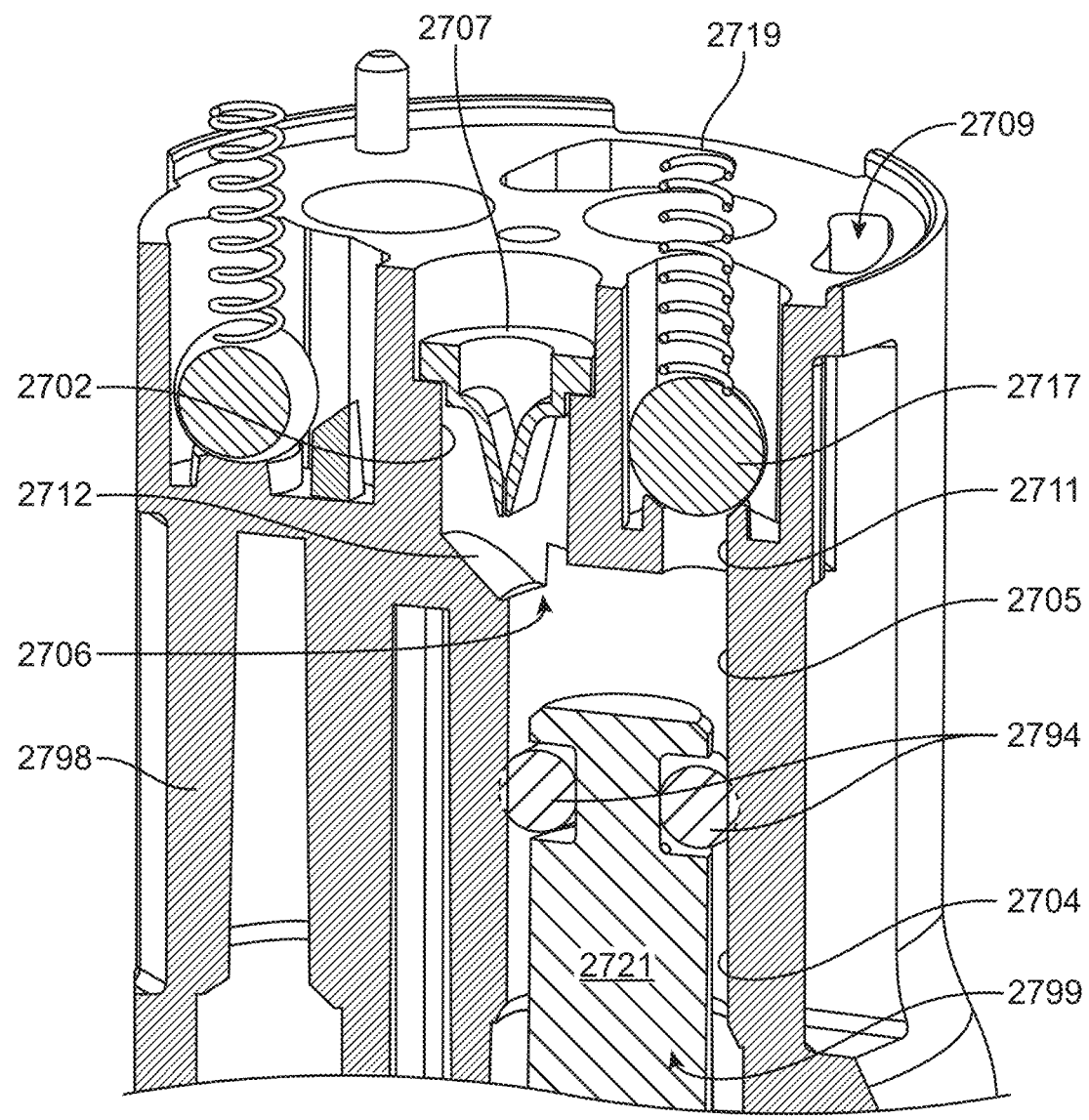
FIG. 4B is another partial, cross-sectional views of instruments illustrating a piston within a piston chamber.

The vacuum chamber 2703 is configured to be in fluid communication with the one or more pumping chambers 2705 via a respective opening 2706 regulated by a one-way valve 2707 (see FIGS. 4A and 4B). The configuration of the one-way valve 2707 can vary including a duckbill valve, ball check valve, lift-check valve, stop-check valve and other types of valves that allow flow of fluid in a single direction and cut-off flow of fluid in the opposite direction. Movement of the pistons 2799 in a first direction within the piston chambers 2704 (i.e. proximally or towards the rear of the hand piece) creates a vacuum that can be supplied to the lumen of the elongate member 2755 through the openings 2706 of the vacuum manifold 2774 that surround the elongate member 2755 (not visible in FIG. 4B). The vacuum applied to the lumen 2763 of the elongate member 2755 can pull waste material from the eye into the lumen 2763 of the elongate member 2755. The waste material exits the lumen 2763 and emptied into the vacuum chamber 2703. Material from the vacuum chamber 2703 is pulled through the one-way valve 2707 into the pumping chamber 2705 of the piston manifold 2798. Upon supplying vacuum to the lumen of the cutting tube 1112, material from the eye is drawn into the lumen 1110 of the cutting tube 1112, emptied into the vacuum chamber 2703, and pulled through the one-way valve 2707 into the pumping chamber 2705. Movement of the pistons 2799 in a second, opposite direction within the piston chambers 2704 (i.e. distally or towards the front of the hand piece) causes pressure to build within the pumping chamber 2705 of the piston manifold 2798 and expels material from the pumping chamber 2705 and out of the instrument 2700. The material can be expelled from the system into a disposal enclosure coupled to an exit port as described elsewhere herein. The pressure opens another one-way valve 2713 and allows pressurized waste material to pass through the one-way valves 2713 in the piston manifold 2798. In some implementations, the valve 2713 is a ball check valve. The ball 2717 of the valve 2713 is pushed proximally by the spring 2719 away from opening or waste channel 2711 between the pumping chamber 2705 and the evacuation chamber 2709 thereby opening the valve 2713 during movement of the pistons 2799 in a proximal direction. Upon movement of the pistons 2799 in a distal direction, fluid pressure builds within the pumping chamber 2705 increasing fluid pressure within the chamber and urging the material towards the opening into the waste channel 2711 of the valve 2713. The ball 2717 of the valve 2713 is pushed distally against the spring 2719 such that the spring 2719 compresses and the ball 2717 is urged against the valve opening into the waste channel 2711 thereby closing the valve (see FIG. 4B). The pumping chambers 2705 are substantially devoid of material upon closure of the valve 2713. The one-way valve 2713 is shown as a ball check valve, but can also be a duckbill valve.

The vacuum manifold 2774 can additionally include an evacuation chamber 2709. The evacuation chamber 2709 is sealed off from the vacuum chamber 2703 such that material drawn into the system can be purged from the system without being pushed back out through the cutting tube. The waste material may enter the vacuum manifold 2774 through the waste channels 2711 regulated by the one-way valve 2713. The waste may combine in the vacuum manifold 2774 and be expelled from the device through the evacuation chamber 2709 and into a disposal enclosure coupled to a waste port 2715. The evacuation chamber 2709 may have an oval-shaped channel that runs through the vacuum, piston, and rear manifolds 2774, 2798, and 3260 although it should be appreciated that other shapes are considered herein. Waste may exit the device via the waste port 2715 on the rear manifold 3260. The evacuation chamber 2709 may be sealed off from the vacuum chamber 2703 such that material drawn into the instrument 2700 can be purged from the instrument 2700 without being pushed back out through the elongate member 2755.

The vacuum chamber 2703 is configured to be in fluid communication with the one or more pumping chambers 2705 through respective one-way valves 2707 positioned within openings 2706. In some implementations, a recess 2702 between the valve opening 2706 and the pumping chamber 2705 can have a floor 2712 that is angled to encourage movement and clearing of material through the valve 2707 into the pumping chamber 2705 (see FIG. 4B). The angle of the floor 2712 relative to the axis of the valve 2707 can vary from about from about 1 degrees up to about 90 degrees. In some implementations, the angle can be about 20 degrees up to about 45 degrees. The angle of the floor 2712 can be selected to guide lens fragments and material aspirated from the eye towards the pumping chamber 2705. The floor 2712 can also be flat (see, e.g., FIG. 4A showing the floor of the recess below the valve 2707 that is at 90 degree angle relative to the axis of the valve opening).

The instrument can incorporate a plurality of one-way valves that are positioned to allow for fluid flow in and out of the pumping chamber 2705. The configuration of the valves can vary. In some implementations, the valves are non-compliant, one-way valves like ball valves incorporating a relatively rigid ball as discussed above. In other implementations, the valves are compliant. For example, the valves 2707 described herein can be slightly compliant silicone valves such as duckbill valves. The valves 2713 can also be slightly compliant valves. The ball 2717 of the valve 2713 need not be rigid, but can be formed of a material that is compliant under a given amount of pressure. The valve 2713 also need not be a ball valve. The valve 2713 can also be a silicone valve like a duckbill valve similar to valves 2707, except positioned to allow flow in a direction opposite of valve 2707. Thus, valves 2707 can be duckbill valves that allow for flow through the valve in a first direction (i.e. from the eye towards the pumping chamber 2705) and valves 2713 can also be duckbill valves that allow for flow through the valves 2713 in a second, opposite direction (i.e. from the pumping chamber 2705 through the waste channel 2711 opening). Compliant valves such as duckbill valves provide for fluid flow under a certain degree of pressure with very little motion of the valve components.

As mentioned, the valve 2713 can be a ball check valve. The ball 2717 can be rigid and substantially non-compliant such as a hard plastic or metal material. The compliant valves may deform as a reverse positive pressure is imparted on them whereas the non-compliant valves do not deform. If the valve between the vacuum chamber 2703 and the pumping chamber 2705 is a compliant valve and the ball 2717 is substantially non-compliant, then as the piston is travelling distally and generating positive pressure to evacuate the material from the pumping chamber 2705, the positive pressure can cause a deformation of the compliant valve and a small purge or regurgitation of an amount of fluid out the distal opening of the shaft 2761. This regurgitation may occur on every back and forth cycle of the piston 2799. In some implementations, the regurgitation may be optimized further by the design of the pumping chamber 2705. In the pumping chamber 2705, the outlet opening connecting the pumping chamber 2705 to the evacuation chamber 2709 may be located, for example, on the side of the chamber and configured such that the piston 2799 may travel beyond the outlet opening. In this implementation, after the piston 2799 has moved distally beyond the outlet opening there is no other route for fluid evacuation. Therefore, as the pistons 2799 continue to travel distally creating a moment of positive pressure within the pumping chamber 2705 after closure of the valves 2713 that causes a short regurgitation of material at the distal end of the shaft 2761. Thus, the cycles of negative pressure can be interspersed with short regurgitation via application of positive pressure between pulses of negative pressure.

The short periods of vacuum can be interspersed by short periods of decreasing vacuum or no vacuum. In some implementations, the cycles of negative pressure include short periods of vacuum interspersed by short periods of positive pressure thereby resulting in a short regurgitation of fluid through the distal shaft during each cycle of piston movement. Whether or not positive pressure is applied between the pulses of vacuum, the pulsatile vacuum creates pulses of discontinuous negative pressure through the elongate shaft that can be between about 4 inHg up to about 30 inHg, or 10 inHg up to about 30 inHg, preferably as close to full vacuum as possible with very little loss in pressure. In some implementations, the device can create pulses of discontinuous negative pressure through the internal lumen of the elongate member at a cycling frequency. The device can also create pulses of discontinuous positive pressure having the same cycling frequency. Thus, the pulses of discontinuous negative pressure are interspersed by the pulses of discontinuous positive pressure. The cycling of the negative pressure pulses and positive pressure pulses can be a relatively fast frequency, for example, at least about 0.5 Hz up to about 5000 Hz, between 1 Hz and 4000 Hz, between about 10 Hz up to about 2000 Hz, or up to about 5000 Hz-10,000 Hz. In some implementations, the cycling frequency of the pulses of discontinuous negative pressure is between about 1 Hz up to about 500 Hz. The pulses of discontinuous positive pressure expel a second amount of material at the cycling frequency from the internal lumen through the opening. The volume of material being moved per cycle can vary, but is generally relatively small, for example, between about 0.1 mL up to about 1.0 mL, or approximately 0.5 mL. In some implementations, the nominal amount of fluid removed per pulse is about 100 microliters, or between 10 uL up to about 1 mL. In still further implementations, the cycling of the negative pressure pulses provided by the pump can overlap with one another such that the effective aspiration pressure provided is substantially smooth and continuous.

The pulses of discontinuous negative pressure aspirate a first amount of material into the internal lumen 2763 through the distal opening 2765 at the cycling frequency. The pulses of discontinuous positive pressure expel a second amount of material at the cycling frequency from the internal lumen 2763 through the opening. The volume of material being moved per cycle can vary, but is generally relatively small, for example, between about 0.1 mL up to about 1.0 mL, or approximately 0.5 mL. Each piston chamber 2704 or pumping chamber 2705 can have a diameter of about 0.05" to about 0.50". The stroke length of each piston 2799 can be between about 0.10" to about 0.50". The pistons 2799 can create a stroke volume of about 50 cubic mm to about 200 cubic mm. In an implementation, the piston chamber 2704 diameter is about 0.20" and has a stroke length of about 0.20" and a stroke volume of about 100 cubic mm. In some implementations, the nominal amount of fluid removed per pulse is about 100 microliters, or between 10 microliters up to about 1000 microliters. The second amount of material can be substantially less than the first amount of material within this general range of fluid amounts. The pulses of discontinuous negative pressure can be interspersed by discontinuous periods of lessening vacuum, no vacuum, or positive pressure at the same frequency.

Figure 10A:
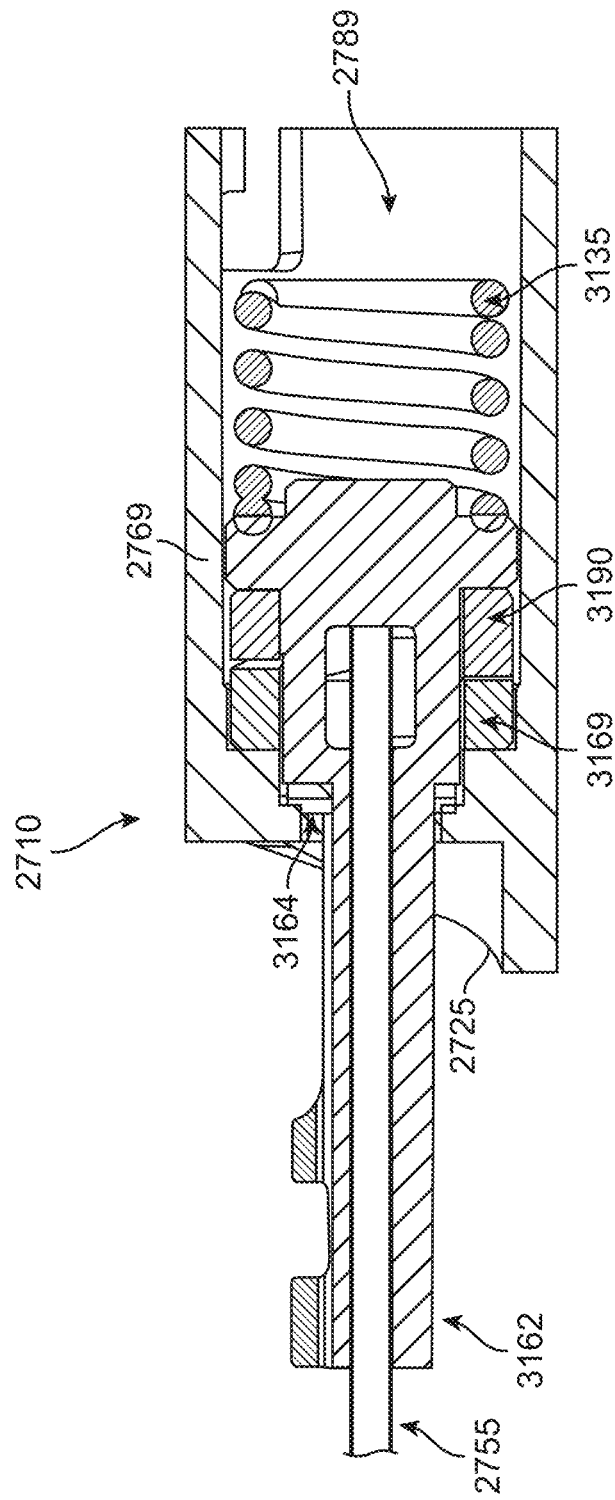
Figure 11A:
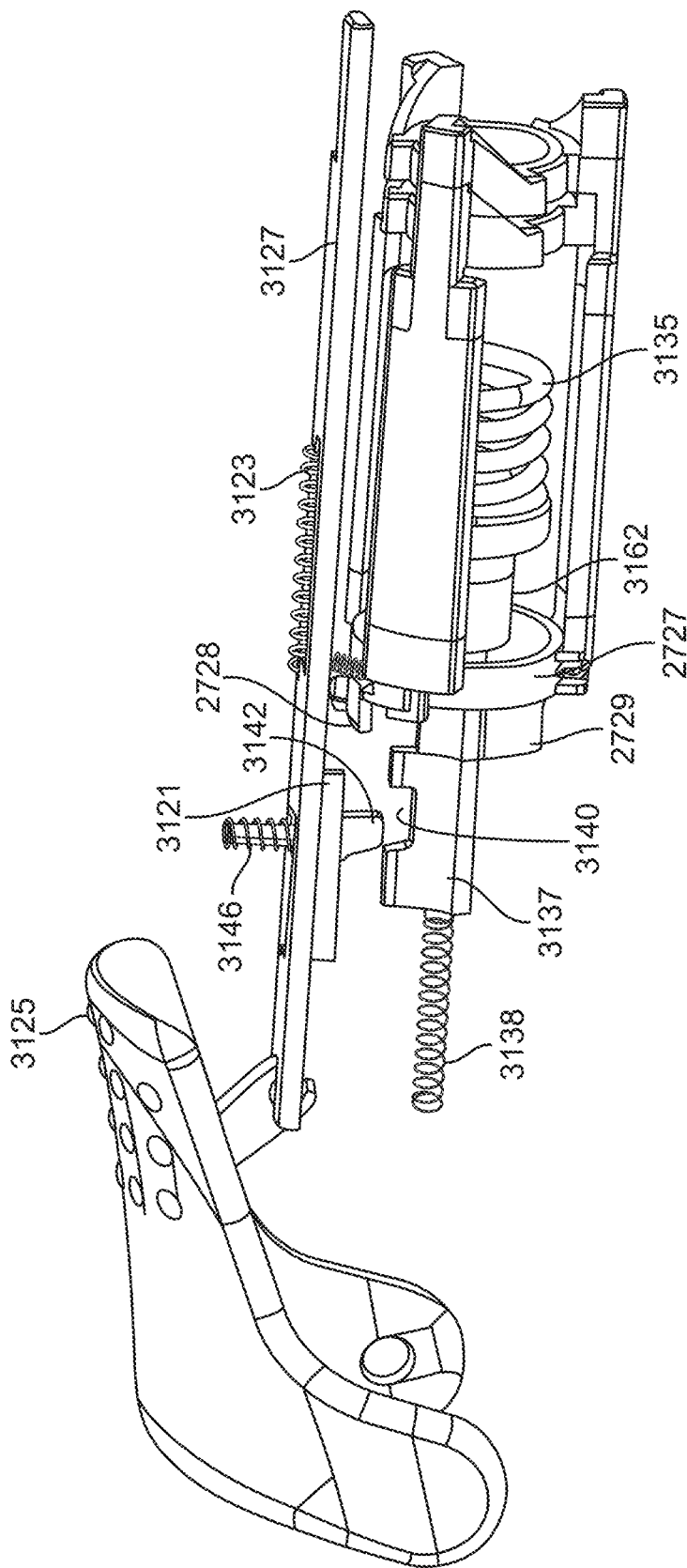
FIGS. 11A and 11B illustrate another implementation of a cam assembly relative to a trigger mechanism.
Figure 11B:
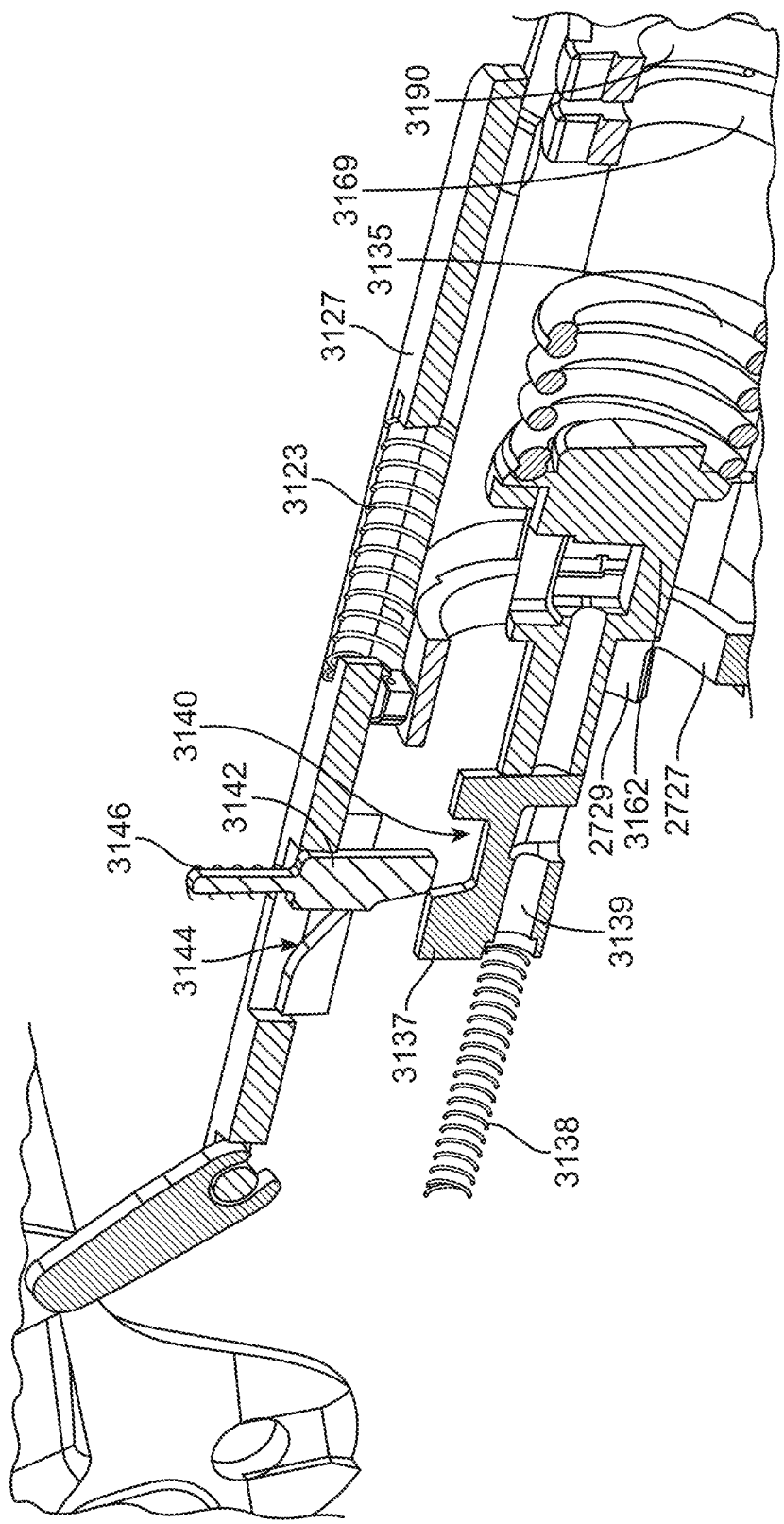

The reciprocating motion of the pistons 2799 can be a function of a cam assembly 2710 driven to rotate by a drive mechanism, each of which will be described in more detail below. FIGS. 10A-10C show an implementation of a cam assembly 2710. Again with respect to FIG. 4A, the pistons 2799 positioned within their respective piston chambers 2704 can include an elongate central piston rod 2721 surrounded by a piston spring 2701 extending between piston heads 2723a, 2723b. The piston spring 2701 can be biased to urge the piston 2799 proximally towards a proximal end of the piston chamber 2704. A distal piston head 2723a and sliding O-ring seal 2794 can be positioned within a first portion of the piston chamber 2704. The piston spring 2701 and proximal piston head 2723b can be positioned within a second portion of the piston chamber 2704 located proximal to the first portion. The first portion of the piston chamber 2704 has an inner dimension that is smaller than the second portion of the piston chamber 2704 and the outer dimension of the piston spring 2701. Thus, as the piston 2799 is urged distally, the piston spring 2701 is compressed between the proximal piston head 2723b and the step-down in inner diameter of the piston chamber 2704. Once the distally directed force is removed, the piston spring 2701 urges the piston 2799 proximally.

Figure 5A:
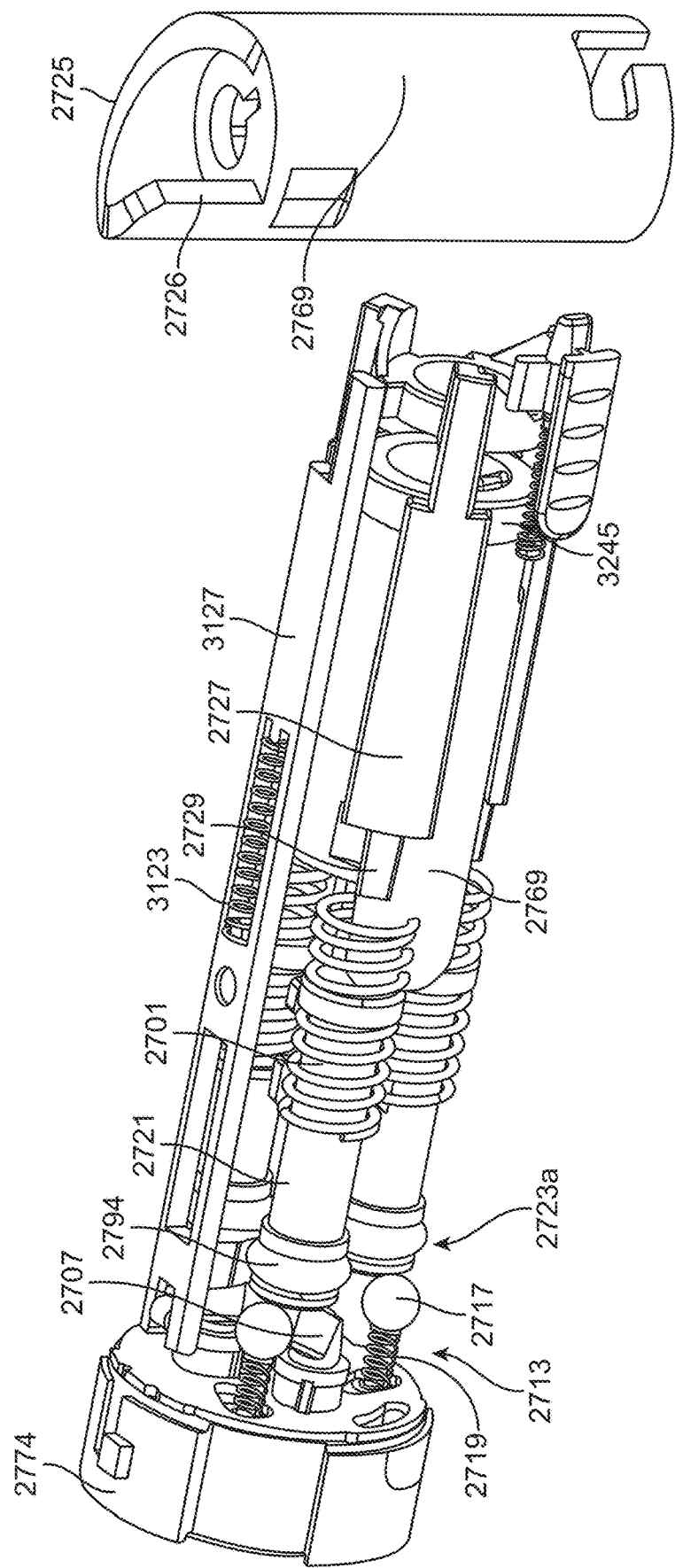
FIG. 5A illustrates a cam assembly relative to the piston pump of an microsurgical instrument.
Figure 5B:
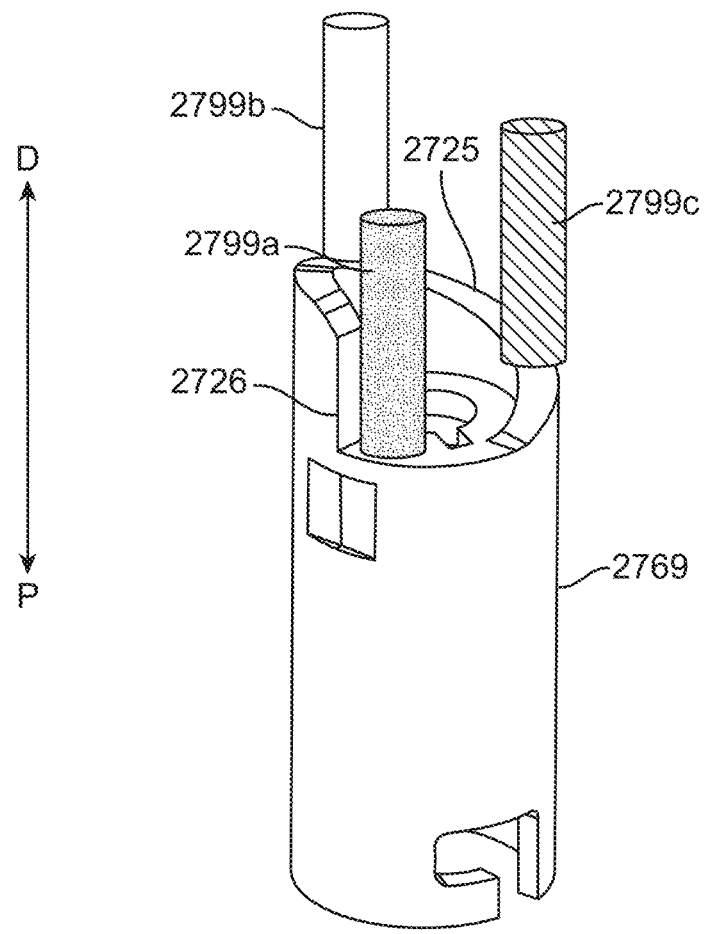
FIG. 5B illustrates a rotating cam relative to a plurality of pistons.

The cam assembly 2710 can include a rotating cam 2769 configured to convert rotary motion of a motor into the reciprocating linear motion of the pistons 2799. The rotating cam 2769 can be a cylindrical element having a cam surface 2725 (see FIG. 5A). The rotating cam 2769 can be positioned proximal to the pistons 2799 such that the proximal piston heads 2723b can travel along the cam surface 2725. The cam surface 2725 can have any of a variety of geometries to achieve a desired motion of the pistons 2799 in the distal and the proximal directions. The cam surface 2725 can include at least a first portion leading towards a distal peak and a second portion leading away from the distal peak. In some implementations, the second portion leading away from the distal peak can include a sharp drop-off or ledge 2726 as shown in FIG. 5A. In other implementations, both the first portion leading towards the distal peak and the second portion leading away from the distal peak can be ramped surfaces. The second portion, whether a ramp or a ledge 2726 having a sharp drop-off, can have a steeper geometry compared to the first portion so that motion of the pistons 2799 in the proximal direction along the second portion occurs faster than motion of the pistons 2799 in the distal direction along the first portion. This allows for creation of pulsatile vacuum.

In an implementation, during a first fraction of rotation of the cam 2769, the proximal piston heads 2723b slide along the first portion of the cam surface 2725 and the pistons 2799 are sequentially moved distally along the longitudinal axis of the device. The piston springs 2701 of the pistons 2799 are, in turn, sequentially compressed. During a second fraction of rotation of the cam 2769, the proximal piston heads 2723b slide past the distal peak of the cam surface 2725 that terminates at ledge 2726. When the piston heads 2723b drop off ledge 2726 the distally directed force against the pistons 2799 by the cam 2769 is sequentially released as each piston head 2723b drops of the ledge 2726. The piston springs 2701 surrounding the piston rod 2721 sequentially urge the pistons 2799 backwards towards the proximal end region of the piston chamber 2704 creating a vacuum within the respective pumping chambers 2705 through the one-way valves 2707 as described above. A complete revolution of the cam 2769 therefore allows for axial movement of each piston 2799 in succession. The piston heads 2723b slide along the cam surface 2725 and extend in the distal direction at a first rate and the piston heads 2723b drop off the cam surface 2725 and retract in the proximal direction at a second rate that is much faster than the first rate. The vacuum pulses can be designed to occur suddenly, for example, by the piston 2799 falling off the ledge 2726 of the cam surface 2725 and being pushed proximally towards the proximal end of the pumping chamber 2705 by the piston spring 2701.

The geometry of the cam surface 2725 can be designed to provide different motion profiles of the pistons 2799 in their respective piston chambers 2704 and thereby create different vacuum profiles (i.e. smooth continuous, continuous with spikes in negative pressure, or discontinuous pulsed negative pressure). The cam surface 2725 can be elliptical, eccentric, egg, or snail-shaped. The timing of this piston movement can vary based on the geometry of the cam surface 2725 (and the location of the ledge 2726, if present), relative to the cam surface 2725. For example, the timing of when one piston retracts to create a negative pressure within the chamber relative to when the next piston retracts to create a negative pressure can be a function of the cam surface 2725 geometry. The timing of this retraction along the second portion having a steeper geometry than the first portion of the cam surface 2725 can be leveraged to achieve a more pulsatile vacuum profile. Pulsatile vacuum can be beneficial for breaking up the lens and removing the lens material from the eye in that the peak vacuum level can be higher for these short bursts of time than can be achieved if steady vacuum is applied because the flow rate is kept below a nominal amount (e.g. 50 cc/minute). High peaks of vacuum are created, but a low overall flow rate can be maintained.

The ledge 2726 (or steeper second portion) of the cam surface 2725 can allow each piston 2799 to retract quickly upon reaching the ledge 2726. The piston 2799 extends at a first rate in a distal direction as it moves along the ramped portion of the cam surface 2725 and then at a second, faster rate in the proximal direction as it drops off the ledge 2726. In other implementations, the cam surface 2725 has a first ramp connected to the ledge 2726 by a second ramp. The first ramp of the cam surface 2725 allows for gradual extension of each piston 2799 and the second ramp allows for gradual retraction of each piston 2799. Thus, each piston 2799 will gradually retract a distance before the piston 2799 drops off the ledge 2726 to retract quickly the rest of the rearward travel.

Figure 8A:
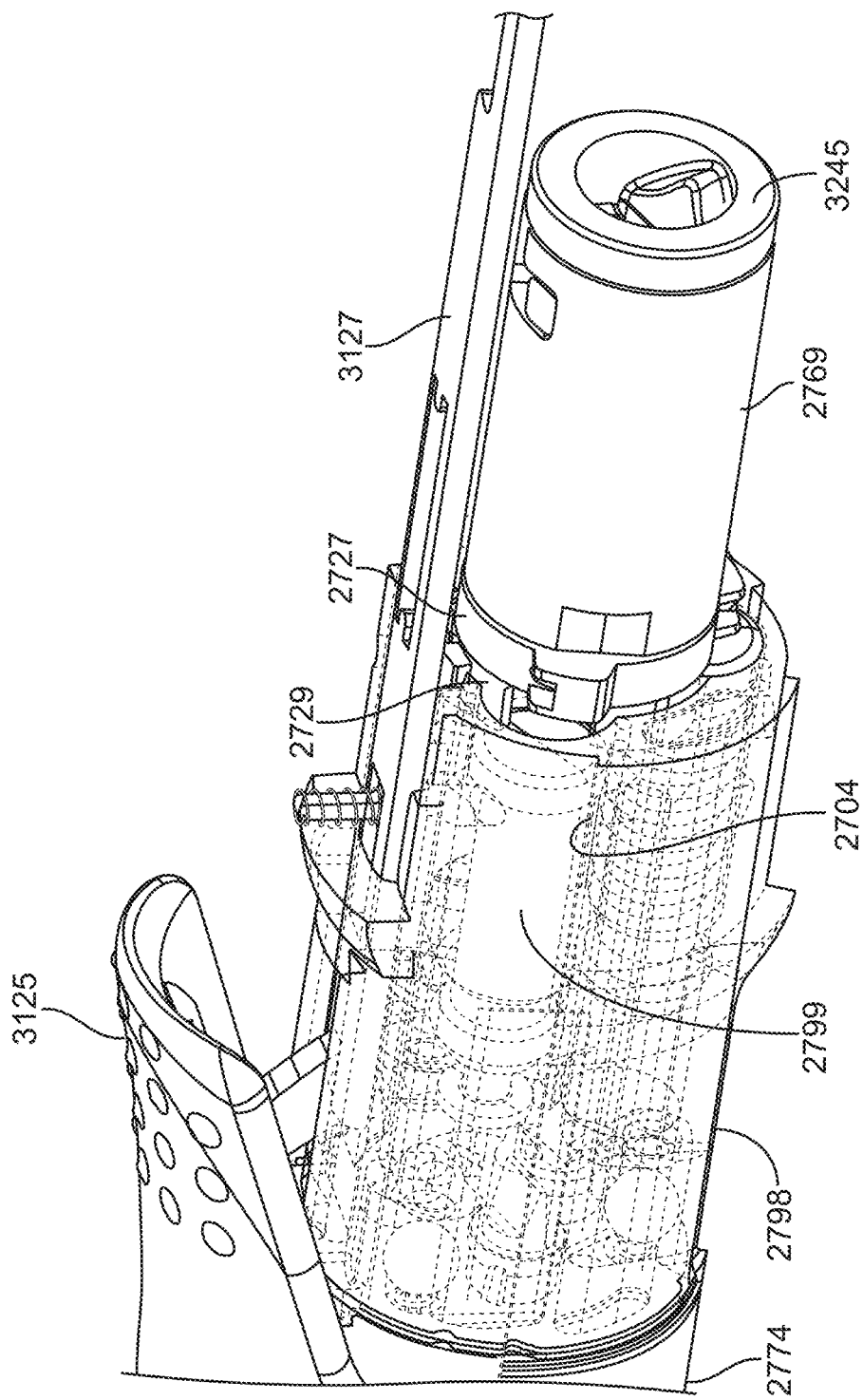
FIG. 8A is a partial, perspective view of a trigger system in a resting position.
Figure 8B:
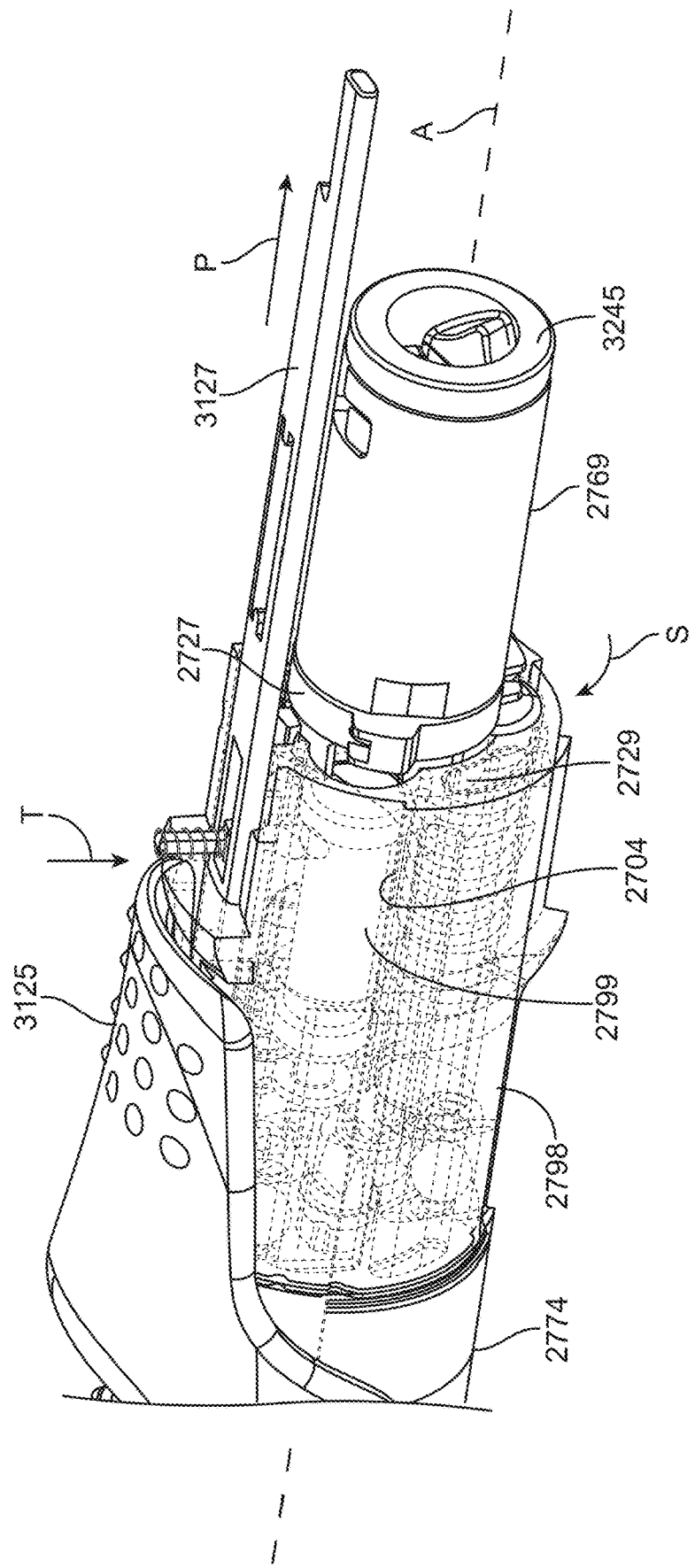
FIG. 8B is a partial, perspective view of the trigger system of FIG. 8A in a fully actuated position.

The timing of when a first piston is retracting and the next piston retracts can be a function of the geometry of the cam surface 2725 and the relative movements of the pistons 2799 within the piston chamber. The vacuum pulses can be designed to occur more smoothly such that the flow rate provided is substantially smooth and continuous, rather than discontinuous with momentary pauses between vacuum pulses. In some implementations, a first piston may retract and the second piston not start retracting until after a dwell period of the first piston retraction (see FIG. 8B) thereby creating a pulsatile vacuum profile. FIG. 8B illustrates in schematic movement of three pistons 2799a, 2799b, 2799c sliding along the cam surface 2725 of the rotating cam 2769. The cam surface 2725 terminates at a sharp drop-off or ledge 2726. During rotation of the cam 2769, the pistons 2799a, 2799b, 2799c slide along the cam surface 2725 and thereby extend in a distal direction (arrow D). Upon reaching the ledge 2726, a first piston 2799a drops off the ledge 2726 retracting quickly in a proximal direction (arrow P) creating a spike in negative pressure. The geometry of the cam surface 2725 creates a dwell time of no negative pressure before the next piston 2799b reaches the ledge 2726 and retracts creating a second spike in negative pressure. The result is a series of discontinuous pulses of negative pressure.

The aspiration pump of the device 2700 can be configured to provide discontinuous, pulsatile aspiration as described above as well as continuous vacuum flow rate. The different types of vacuum through the elongate member 2755 of the device 2700 can be selectively activated. For example, the device can be manually switched between the two vacuum modes. The first mode can be a substantially continuous vacuum mode without the spike in negative pressure due to the pistons 2799 dropping off the ledge 2726. The second mode can be a substantially continuous vacuum mode with the spikes in negative pressure. The manual switching between the modes can be a function of trigger travel relative to the housing (e.g., greater than a threshold amount of travel of the trigger). Alternatively, the manual switching between the modes can be a separate input on the device that is separate from the trigger (e.g., sliding a separate switch on the housing).

Figure 6:
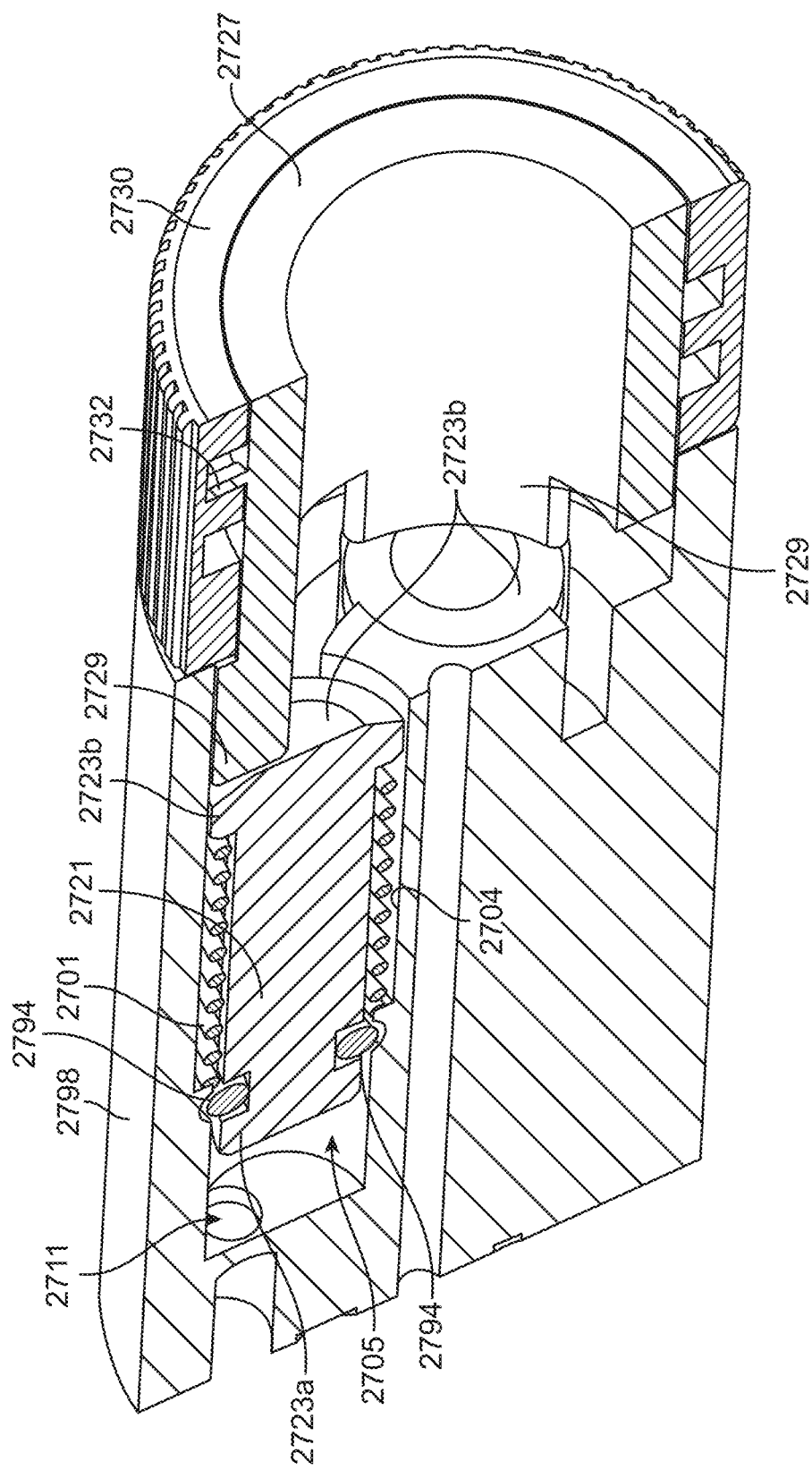
FIG. 6 illustrates a manual piston stop adjustor ring configured to selectively modulate the vacuum achieved by the vacuum source of an instrument.
Figure 7A:
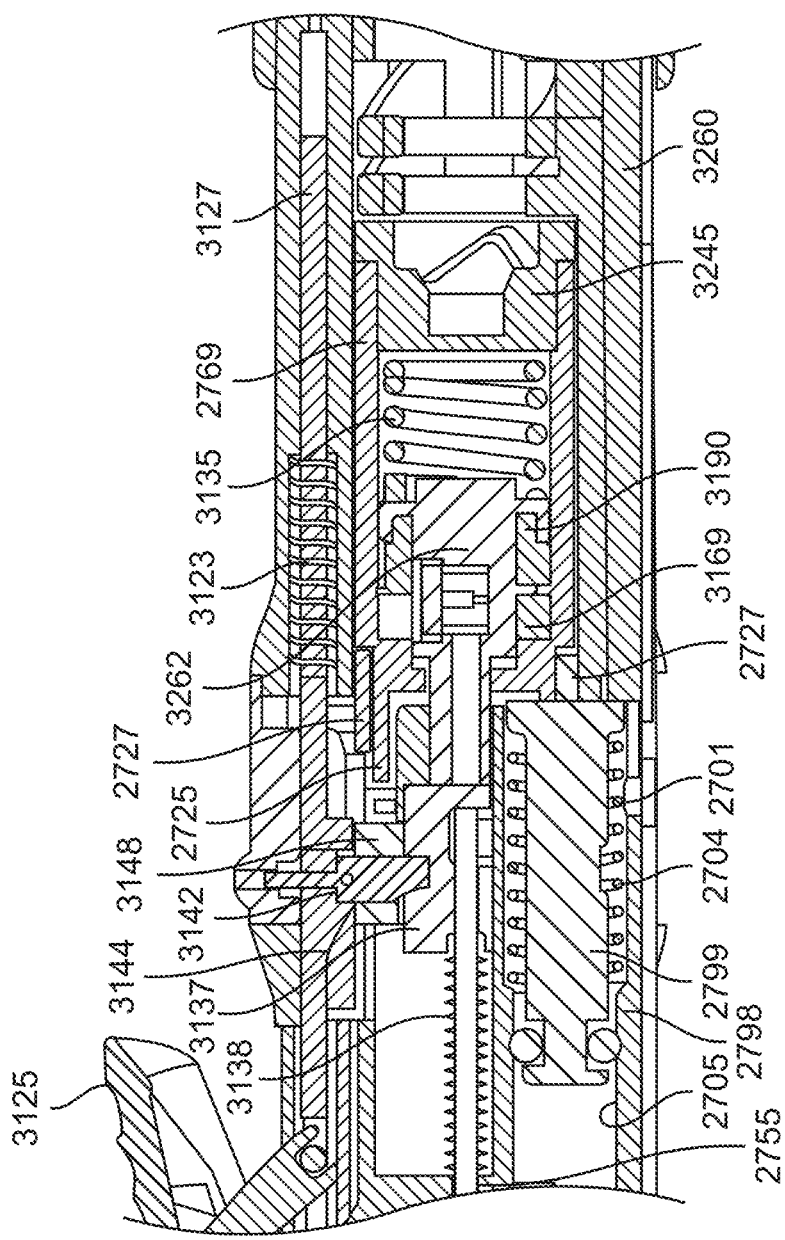
FIG. 7A is a detailed view of FIG. 3A.
Figure 7B:
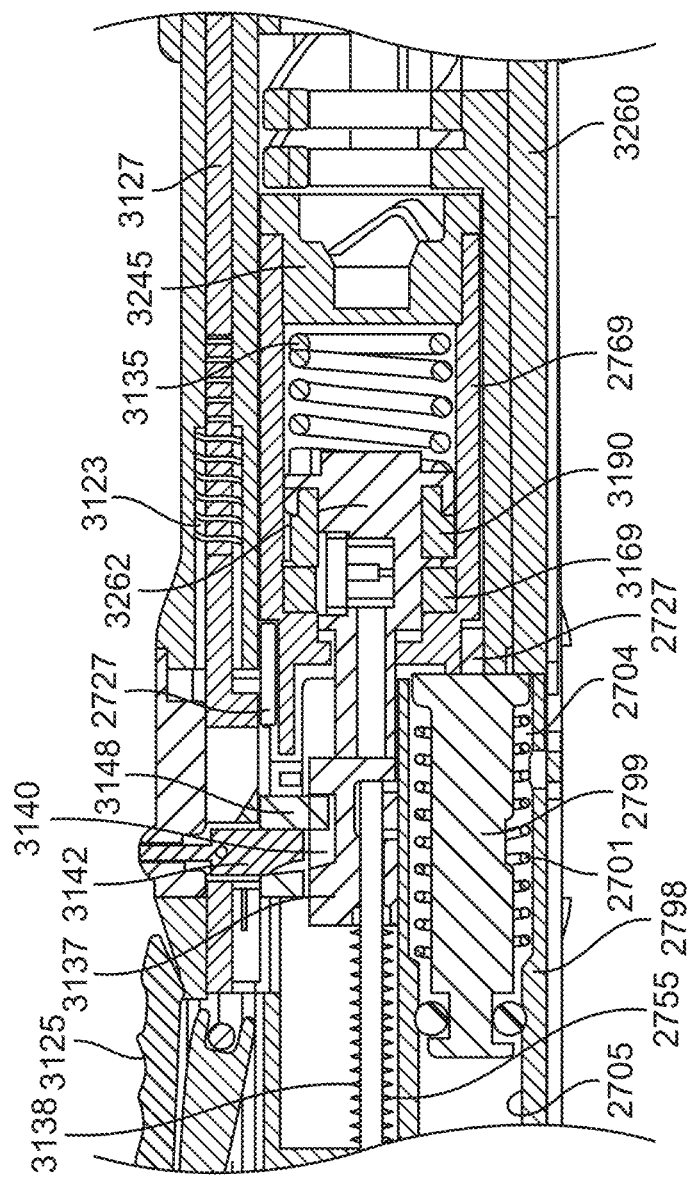
FIG. 7B is a detailed view of FIG. 3B.

The smooth, continuous vacuum can be achieved by limiting the piston retraction to a fraction of the maximum piston travel within the chamber. FIG. 5A and FIG. 6 show a piston stop 2727 coupled to a proximal end region of the piston manifold 2798. The piston stop 2727 can be a generally cylindrical element configured to surround the rotating cam 2769 (not shown in FIG. 6) such that the rotating cam 2769 extends through the cylindrical piston stop 2727 to contact the proximal ends of the pistons 2799. A distal end region of the piston stop 2727 can define one or more projections 2729 configured to project into a proximal end region of each of the piston chambers 2704 in the piston manifold 2798. The projections 2729 can abut against the proximal piston heads 2723b of respective pistons 2799 when positioned at a proximal-most end region of their respective piston chambers 2704. For example, if the device 2700 includes three pistons 2799 positioned in three piston chambers 2704, the piston stop 2727 includes three projections 2729 configured to abut against the proximal piston head 2723b of each of the three pistons 2799. Thus, both the cam 2769 and the projections 2729 of the piston stop 2727 are configured to contact the proximal ends of the pistons 2799, the cam 2769 on an inner region and the projections 2729 on an outer region.

The piston stop 2727 provides a hard stop to the proximal linear travel of the pistons 2799 upon expansion of the piston springs 2701 when the pistons 2799 drop off the ledge 2726. For example, maximum piston travel within its piston chamber 2704 can be a distance of 5 mm. The projections 2729 of the piston stop 2727 can be advanced into the piston chamber by 2 mm thereby to limit proximal retraction of the piston 2799 to a distance of 3 mm rather than the maximum 5 mm. As the cam 2769 turns and the pistons 2799 extend and retract along the cam surface 2725, the projections 2729 of the piston stop 2727 can effectively prevent the pistons 2799 from dropping off the ledge 2726 thereby creating a smooth, continuous negative pressure without the spike in negative pressure. When the projections 2729 of the piston stop 2727 are withdrawn from the piston chamber 2704, the pistons 2799 can once again travel the maximum distance and can drop off the ledge 2726 creating a spike in negative pressure. The piston stop 2727 limits the overall volume of the pumping chamber 2705 that can be achieved.

The relative position of the piston stop 2727 and thus the projections 2729 within the piston chambers 2704 can be adjustable by a user to provide a plurality of selectable vacuum settings. The relative position of the piston stop 2727 within the piston chamber 2704 can limit the maximum vacuum achieved as well as determine the type of vacuum achieved (continuous or pulsatile). For example, the piston stop 2727 can prevent the pistons 2799 from dropping off the ledge 2726 creating a smooth continuous vacuum or smooth continuous with spikes in pulsatile vacuum. As the piston stop 2727 is adjusted to be positioned more proximally relative to the piston manifold 2798, the projections 2729 are withdrawn from the piston chambers 2704 and do not limit (or limit to a lesser degree) the linear travel of the pistons 2799 in a proximal direction upon expansion of the piston springs 2701. This, in turn, maximizes the size of the pumping chamber 2705 and achieves pulsatile vacuum. In some procedures or certain steps of a procedure, higher pressures may be more desirable than in other procedures or steps of the procedure. The higher pressure can be selected, for example, by actuating the piston stop 2727 to a wider setting such that the pistons 2799 can travel a longer distance per cycle and maximum vacuum achieved. In some implementations, the piston stop 2727 position can be toggled between a "high vacuum" position and a "low vacuum" position. The adjustment can be based on degree of trigger actuation and/or by manually selecting a vacuum setting using another input on the device 2700, each of which will be described in more detail below. In other implementations, the piston stop 2727 position can be "dialed in" to any of a plurality of vacuum settings that are conveniently selected during use. In other implementations, the relative relationship of the disposable to reusable portions 3205, 3210 is adjustable and, in turn, can limit the distance the pistons can travel backwards. For example, the reusable portion 3210 is positioned onto the disposable portion 3205, the more limited the piston travel is due to the piston stop 2727. In some implementations, the vacuum source can create a sudden rise in vacuum forming a vacuum profile that causes the cornea and the eye effectively to "bounce" up and down during application of pulsed vacuum. For example, when the pistons 2799 are sprung backwards they can create the sudden rise in vacuum forming a vacuum profile that resembles a "saw tooth" (i.e. suction-pause-suction). Limiting the backwards travel of the pistons 2799 inside their respective piston chambers 2704 by the piston stop 2727 can reduce the amount of suction impact or shock that is created each time the pistons 2799 are sprung backwards. The piston stop 2727 can thereby limit the maximum suction created with each piston travel reducing the impact this abrupt suction can have on the eye. The vacuum created with each backwards travel of the pistons 2799 can be greater than 500 mmHg up to about 700 mmHg.

FIG. 6 shows a manual adjustment ring 2730 can be positioned around an outer surface of the piston stop 2727. The adjustment ring 2730 can be available to a user on an external surface of the device 2700, such as the disposable portion 3205. The adjustment ring 2730 can have a threaded inner surface configured to engage with a corresponding pin 2732 on an outer surface of the piston stop 2727. The pin 2732 is configured to slide within the threads of the adjustment ring 2730 such that the piston stop 2727 travels axially along the longitudinal axis of the device. As the piston stop 2727 is adjusted to be positioned further distal relative to the piston manifold 2798, the projections 2729 extend further into the piston chambers 2704 and limit the linear travel of the pistons 2799 in the proximal direction upon expansion of the piston springs 2701.

The piston stop 2727 position can also be selectively adjusted between a smooth, continuous vacuum and a pulsed vacuum depending on degree of actuation of an input, such as the multi-stage trigger 3125. A trigger-actuated piston stop 2727 is shown in FIGS. 3A-3B, FIGS. 7A-7B showing detailed view at circles A-A and B-B of FIGS. 3A-3B, FIGS. 8A-8B, and FIGS. 9A-9F.

The piston stop 2727 can be movably coupled to the trigger to limit the proximal travel of the plurality of pistons within their respective cylinders. The piston stop can maintain the vacuum generation source in a low flow continuous aspiration mode during rotation of the cam assembly by limiting proximal travel of each piston within its respective cylinder to less than a maximum proximal travel. Trigger actuation beyond a certain degree can move the piston stop relative to the plurality of pistons switching the vacuum generation source to a discontinuous pulsatile aspiration mode. As will be described in more detail below, the trigger can cause the piston stop to rotate around a longitudinal axis of the housing upon actuation of the trigger beyond the particular degree.

The piston stop 2727 need not travel axially along the longitudinal axis of the device to switch between smooth and pulsed vacuum modes. The piston stop 2727 can rotate around the longitudinal axis without any axial movement relative to the pistons. A first position around the longitudinal axis can result in at least a portion of the piston stop 2727 engaging with the pistons preventing their maximum travel. A second position around the longitudinal axis can result in the portion of the piston stop 2727 disengaging with the pistons allowing their maximum travel.

Figure 9A:
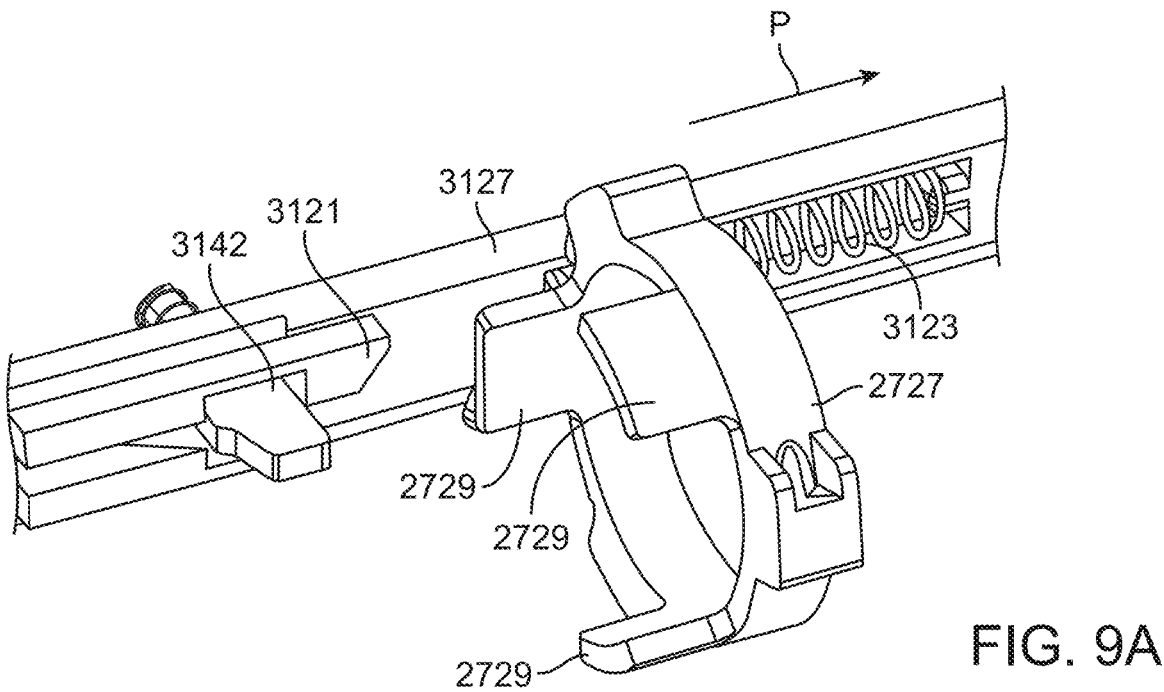
FIGS. 9A-9B are partial views of the trigger system illustrating a piston stop adjustment mechanism.
Figure 9B:
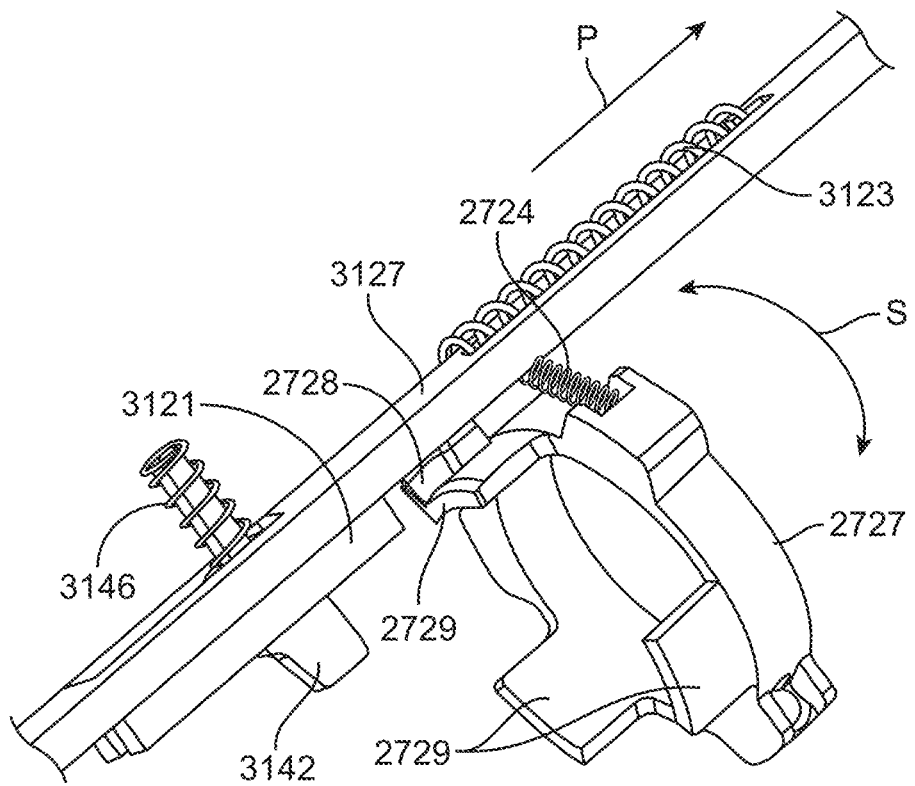
Figure 9C:
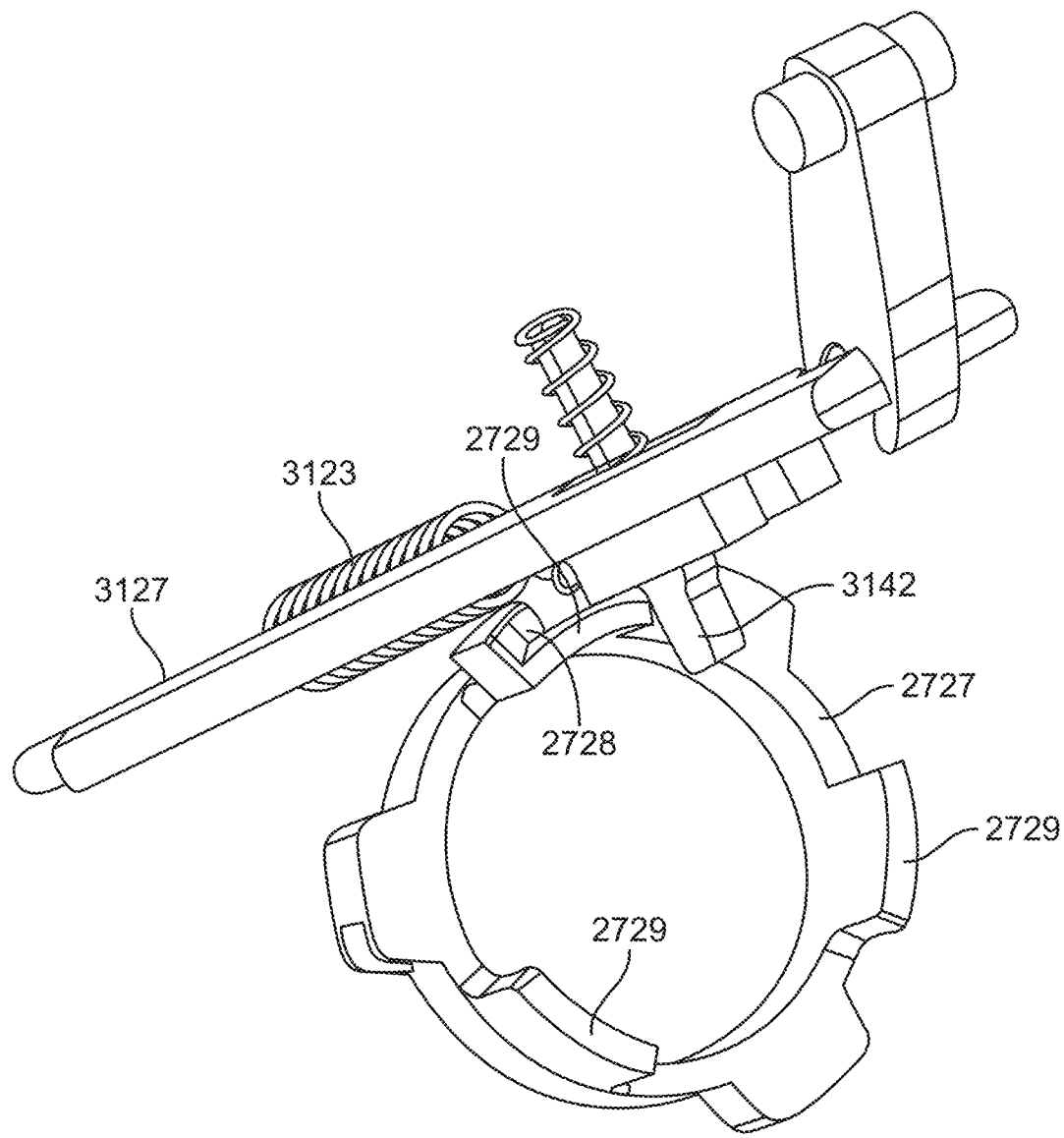
FIG. 9C is a partial view of the trigger system illustrating the piston stop adjustment mechanism.
Figure 9D:
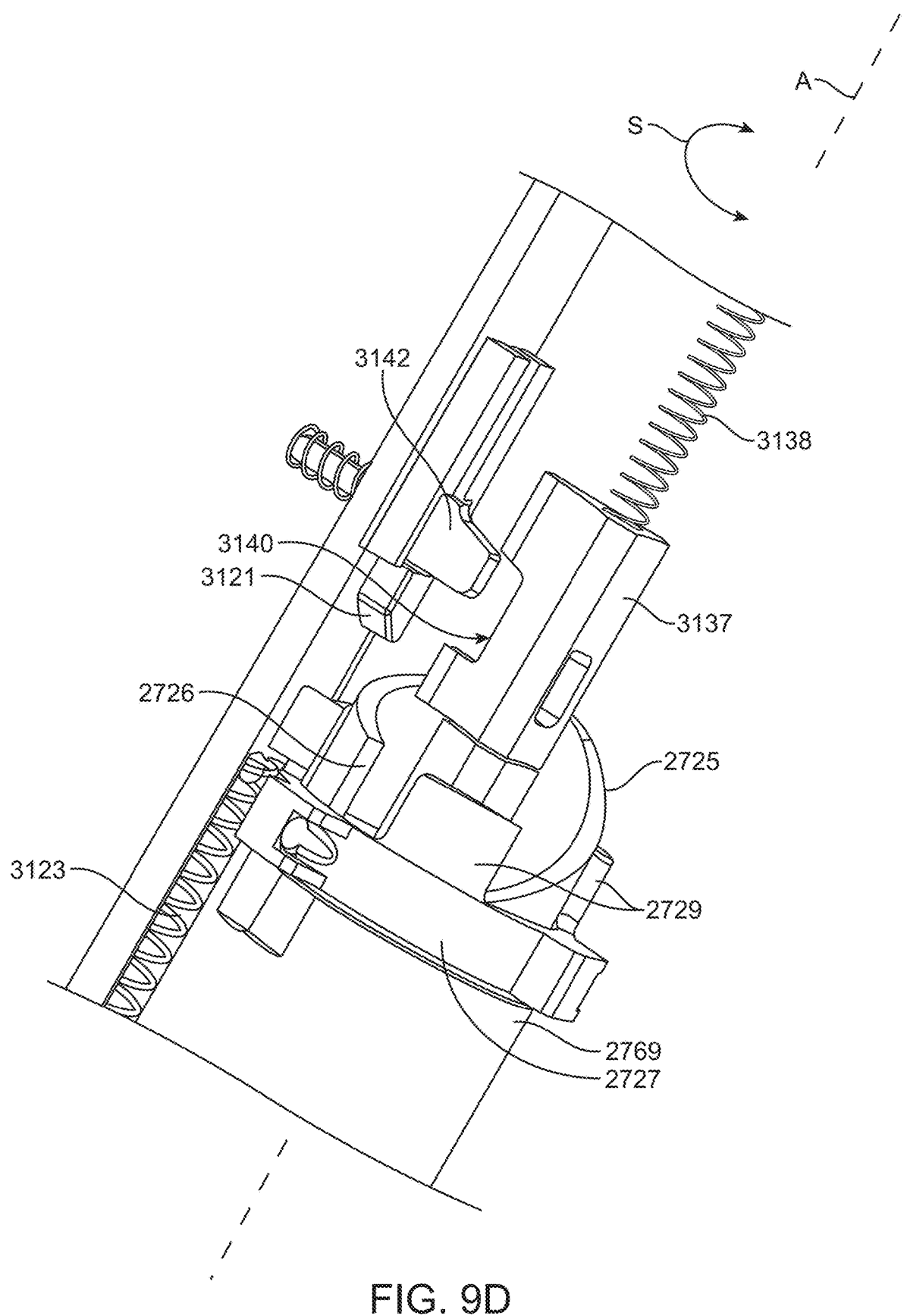
FIG. 9D is a partial view of the trigger system and piston stop adjustment mechanism relative to a rotating cam.

The piston stop 2727 can be ring-shaped such that it can surround the distal end region of the rotating cam 2769 (see FIG. 9D). As discussed above, the rotating cam 2769 spins during actuation of the device to create a vacuum for aspirating material through the elongate member 2755. The cam surface 2725 of the rotating cam 2769 is configured to engage with the proximal ends of the pistons 2799 to urge them in a distal direction within their respective piston chambers 2704 upon rotation of the cam 2769. The piston stop 2727 has projections 2729 that can also engage with the proximal ends of the pistons 2799. Where the cam surface 2725 engages with the pistons 2799 more centrally relative to the longitudinal axis A of the device, the piston stop projections 2729 can engage with the pistons 2799 on an outer region. The rotational position of the piston stop 2727 relative to the rotating cam 2769 is adjustable around the longitudinal axis A along arrow S upon depression of the trigger 3125. When the trigger 3125 is in a resting position, the piston stop 2727 is positioned such that the projections 2729 are aligned with the proximal ends of the pistons 2799 within their respective piston chambers 2704 (see FIGS. 9D and 9E). The projections 2729 bridge the gap between the ledge 2726 and the upward ramp of the cam surface 2725 thereby preventing the pistons 2799 from dropping off the ledge 2726 and full proximal retraction. Upon a first degree of trigger depression 3125, the piston stop 2727 can remain in this position allowing for smooth, continuous low flow aspiration. Upon further trigger 3125 depression, the piston stop 2727 can rotate around the longitudinal axis A along arrow S so that the projections 2729 are no longer aligned with the piston chambers 2704 and no longer bridge the gap (see FIG. 9F). This rotational position allows the pistons 2799 to drop off the ledge 2726 to create a discontinuous, pulsatile flow.

The trigger 3125 can be coupled to a button rod 3127 that is movable along the longitudinal axis A of the device as the trigger 3125 is actuated into one of a plurality of positions (see FIGS. 3A-3B, 7A-7B, 8A-8B, and 9A-9D. For example, when the trigger 3125 is moved from the resting position (see FIGS. 3A, 7A, and 8A) into an actuated position (see FIGS. 3B, 7B, and 8B) the button rod 3127 extends towards or into a proximal portion of the device (e.g. the durable portion 3210). The extension of the button rod 3127 can affect the rotational position of the piston stop 2727 relative to the rotating cam 2769. When the trigger 3125 is in a resting state or actuated into an initial downward position along arrow T, the button rod 3127 moves proximally a first distance along the longitudinal axis A in the direction of arrow P. The piston stop 2727 maintains its rotational position where the projections 2729 are aligned with the piston chambers 2704 in the bridging position between the ledge 2726 and the cam surface 2725. The bridging position prevents the pistons 2799 from achieving full proximal motion within the piston chambers 2704 and from dropping off the ledge 2726. Instead, the projections 2729 allow the pistons 2799 to start back up the ramped cam surface 2725 smoothly. This relative position between the projections 2729 and the cam surface 2725 (see FIG. 9D) achieves a smooth continuous vacuum as opposed to a discontinuous, pulsatile vacuum. When the trigger 3125 undergoes a further degree of downward actuation along arrow T, the button rod 3127 moved proximally a second distance along the longitudinal axis A in the direction of arrow P. The piston stop 2727 is urged to rotate around the longitudinal axis A along arrow S (see FIG. 9F). The projections 2729 no longer align with the piston chambers 2704 and no longer bridge the gap such that the pistons 2799 can start dropping off the ledge 2726 of the rotating cam 2769 to create discontinuous, pulsatile flow.

Figure 9F:
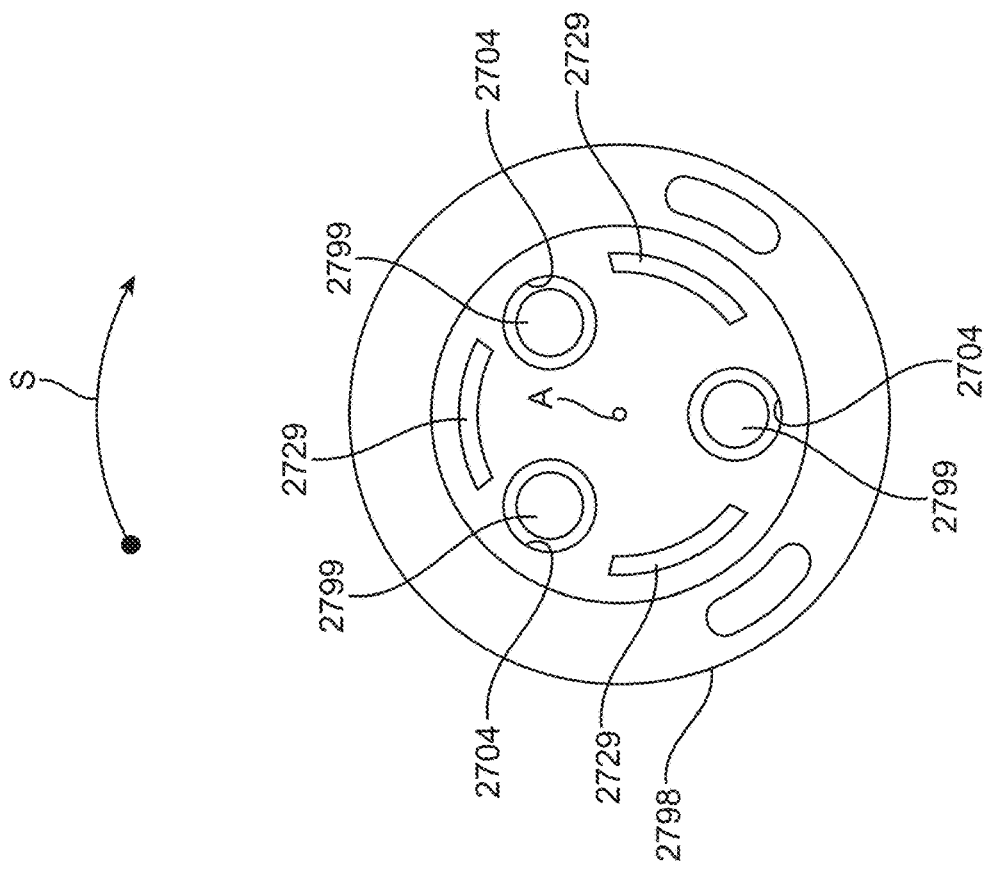
FIGS. 9E-9F are schematic views of the relationship between the piston stop and the piston chambers in a smooth flow aspiration position (FIG. 9E) and a pulsatile flow aspiration position (FIG. 9F).
Figure 9E:
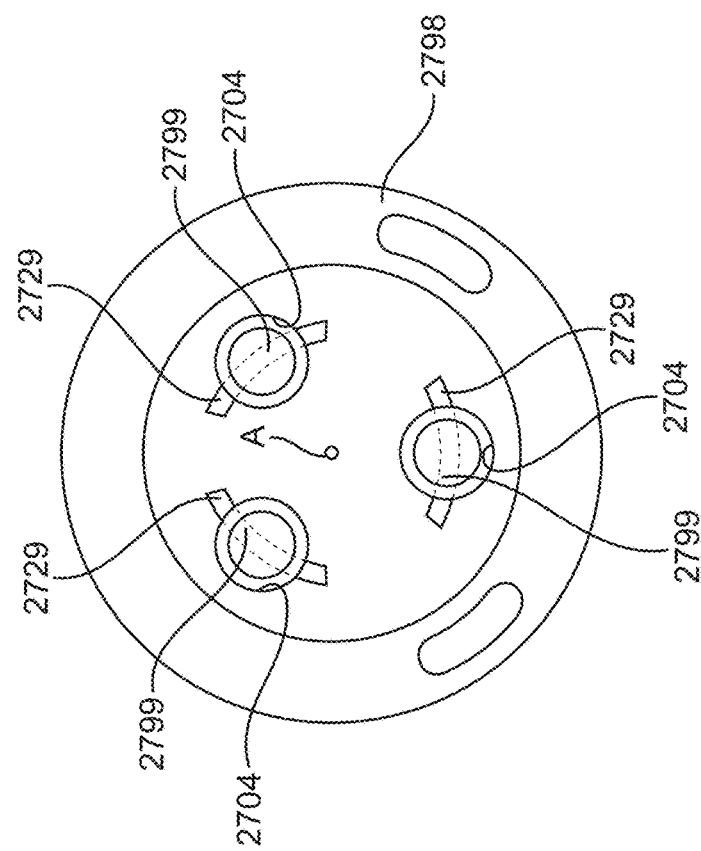

FIGS. 9E-9F illustrate the rotation of the piston stop relative to the piston chambers 2704 in an exaggerated way. The motion of the piston stop 2727 around the longitudinal axis A can be minimal to still encroach upon the piston chamber 2704 and prevent full proximal retraction of the pistons 2799. Thus, the projections 2729 need not fully align with or bridge the gap between the ledge 2726 and the ramp of the cam surface 2725 in order to affect piston 2799 motion within its piston chamber 2704.

The linkage between the trigger 3125 and the piston stop 2727 can vary. FIGS. 9A-9D illustrate one implementation of the linkage. The button rod 3127 can incorporate a wedge element 3121 configured to interact with a ramped surface 2728 on the piston stop 2727 upon proximal motion of the button rod 3127. The button rod 3127 can move along the longitudinal axis A in the proximal direction (arrow P). The wedge element 3121 can be positioned on a lower surface of the button rod 3127 and, upon moving a first distance, can be urged against the ramped surface 2728 of the piston stop 2727. The wedge element 3121 can slide along the ramped surface 2728 of the piston stop 2727 causing the piston stop 2727 to rotate around the longitudinal axis A in a first direction along arrow S. The rotation of the piston stop 2727 causes the projections 2729 to move away from alignment with the piston chambers 2704 (see FIGS. 9E-9F). When the trigger 3125 is released, the trigger 3125 and the piston stop 2727 move back to their resting positions. The trigger 3125 can be urged back upward into the resting position by a spring 3123. The spring 3123 can be engaged with a region of the button rod 3127 such that the button rod 3127 slides distally thereby urging the trigger 3125 into the upward resting position. The piston stop 2727 can also include a spring 2724 configured to urge the piston stop 2727 back around the longitudinal axis in the opposite direction along arrow S (see FIG. 9B). In some implementations, the piston stop 2727 can frictionally engage with the rotating cam 2769 so that as the rotating cam 2769 spins counter-clockwise it likewise urges the piston stop 2727 counter-clockwise and into a position that blocks the proximal motion of the pistons. The frictionally engaging surfaces can be along the cylindrical body of the rotating cam 2769 or at the planar face surface forming the proximal end of the piston stop 2727.

Figure 1B:
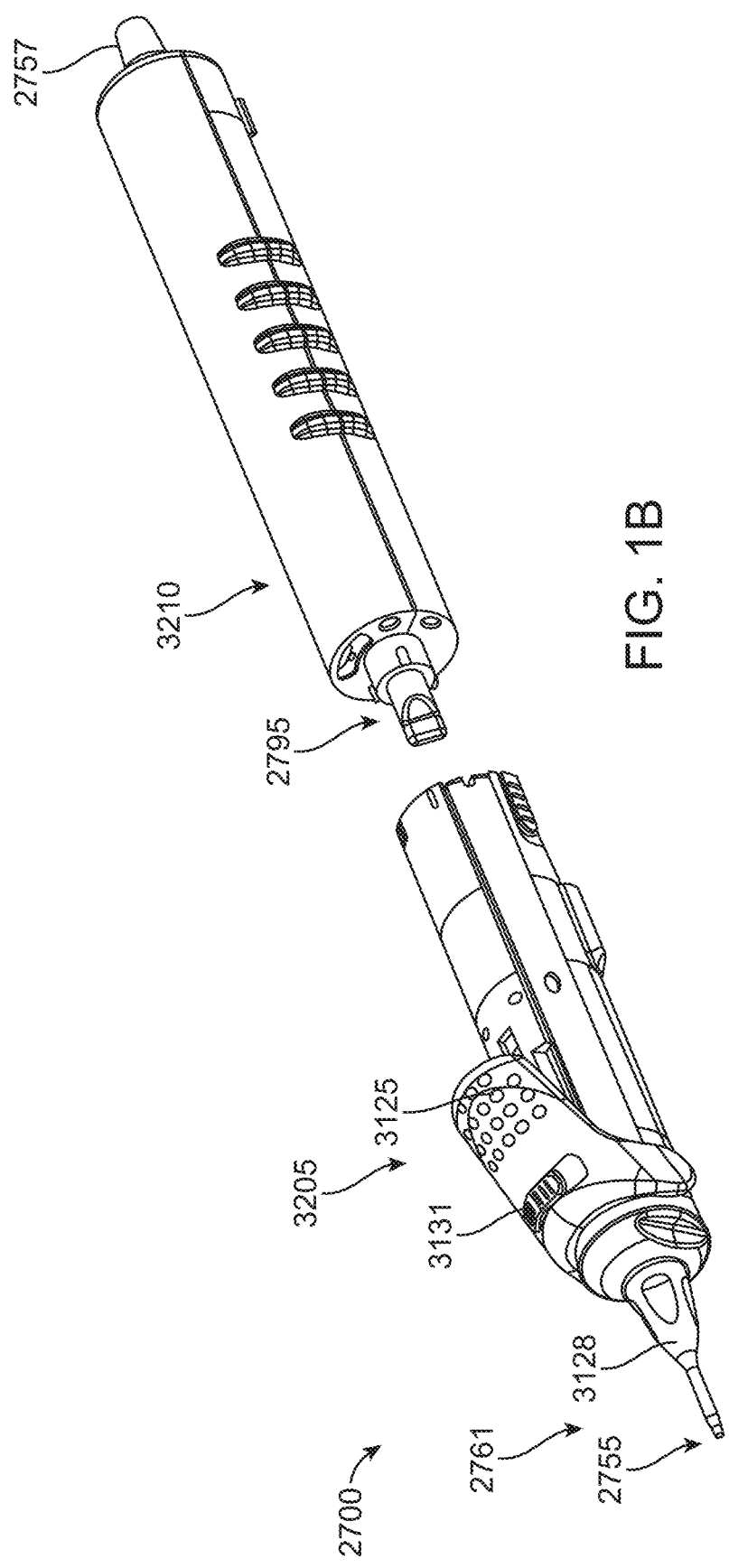
FIG. 1B shows perspective view of the durable and disposable portions of an implementation of a microsurgical instrument separated from one another.

In some implementations, the trigger 3125 can include a toggle switch 3131 (shown in FIGS. 1A-1B). The toggle switch 3131 can limit the movement of the trigger 3125 in certain positions. For example, if the toggle switch 3131 is positioned in a first position (e.g. to the right), the trigger 3125 may be limited in its motion to perhaps 75% of its normal range. If the toggle switch 3131 is positioned in a second position (e.g. to the left), the trigger 3125 may move its full 100% range of motion. This may provide a hard stop for the trigger 3125 that the user can select. For example, in some implementations, the speed of device increases linearly as the trigger 3125 is actuated. The surgeon may position the toggle switch 3131 to the first position such that when trigger 3125 is depressed (or otherwise actuated) to its limited of range of motion a predetermined or preprogrammed function is achieved (lower vacuum or continuous vacuum vs. pulsatile, higher vacuum). This may allow the user to easily switch between different degrees or types of vacuum when the trigger 3125 is fully depressed depending on what position the toggle switch 3131 is set.

It should be appreciated that the input 3125 can incorporate mechanical features or electronic features to achieve the various functions described herein. Actuation of the input 3125 can result in actuation of a potentiometer by an element configured to translate axially or rotate around the longitudinal axis of the device. Non-contact coupling between the input and the motor of the drive mechanism is also considered herein. The input 3125 can incorporate any number of different sensing mechanisms, including capacitive sensors, optical sensors, magnetic or electromagnetic sensors, Hall-Effect sensors, or other sensor that confirms mechanical movement into a signal that is interpreted electronically. In some implementations, the sensor can be a touch sensor. The signal can be interpreted by the electronics and provide input such that the electronics control the device according to the input.

The movement of the pistons 2799 involved in creating aspiration forces and the oscillating movement of the elongate member 2755 involved in cutting can be linked by the cam assembly 2710. The cam assembly 2710 can include the rotating cam 2769 that spins to move the pistons 2799. The cam assembly 2710 can also include a distal cutter cam 3169 and a proximal cam follower 3190 that are involved in the motion of the elongate member 2755 (see FIGS. 10A-10C). Rotating cam 2769 can be affixed to distal cutter cam 3169 such that the rotating cam 2769 and distal cutter cam 3169 spin together. For example, distal cutter cam 3169 can be positioned within a bore 2789 of the rotating cam 2769. A surface of distal cutter cam 3169 can include one or more projections 3168 (see FIG. 10C) sized and shaped to insert within one or more corresponding indents on an inner surface of rotating cam 2769. Any number of coupling arrangements to link the cams 2769, 3169 to spin together are considered herein.

Camming surfaces on the distal cutter cam 3169 and the cam follower 3190 cause axial motion of the cam follower 3190. Distal cutter cam 3169 can include teeth 3132 on its proximal-facing surface configured to engage corresponding teeth 3132 on the distal-facing surface of proximal cam follower 3190. The proximal end of the cam follower 3190 can be connected to a spring 3135 that pushes the cam follower 3190 distally. As the cam 2769 and the distal cutter cam 3169 rotate, the teeth 3132 of the cutter cam 3169 slide along the teeth 3132 of the proximal cam follower 3190 causing the cam follower 3190 to move proximally compressing the spring 3135. The elongate member 2755 coupled to a cutter spline 3162 moves with the cam follower 3190. Thus, the cam follower 3190, cutter spline 3162, and elongate member 2755 are all pushed backward as the teeth 3132 of the cutter cam 3169 slide along the teeth 3132 of the proximal cam follower 3190. The elongate member 2755 can also be connected to an orientation-locking feature such as a rectangular block that prevents the elongate member 2755 and the cam follower 3190 from rotating with the cutter cam 3169.

As the cutter cam 3169 rotates, the camming surfaces cause the cam follower 3190 to move proximally, compressing the spring 3135 further. The camming surfaces have a step 3133 that allows the cam follower 3190 to drop forward (i.e. distally) again at a certain point in the rotation. When the teeth 3132 of the distal cutter cam 3169 reach the step 3133 on the cam follower 3190, the force of the spring 3135 engaged with the proximal end of the cutter spline 3162 urges the elongate member 2755, the cutter spline 3162, and the cam follower 3190 forward or in a distal direction D (see FIG. 10B). A cutter cushion 3164 can be incorporated to provide dampening as the cutter spline 3162 springs back toward the distal position. The cutter cushion 3164 may reduce the noise that the device makes during operation by dampening the cutter spline 3162 as it is sprung forward. Through such a mechanism, the elongate member 2755 can retract with a retraction speed profile that is at least in part a function of the rotational speed of the cutter cam 3169. The rotational speed of the cutter cam 3169 can be controlled so that the maximum tip retraction speed remains below the critical 'cavitation threshold speed' that would otherwise result in cavitation in the eye. The tip of the elongate member 2755 can then extend with an extension speed profile that is at least in part a function of the force of the spring 3135 and mass of the tip assembly. In this way, the average retraction speed can be slow, i.e. below the cavitation threshold speed, but the average extension speed can be fast, i.e. close to or higher than the average retraction speed of a typical phacoemulsification tip. Thus, the benefits of mechanical jackhammering can be achieved while the deleterious effects of cavitation are entirely avoided.

The oscillation of the elongate member 2755 and the motion of the pistons 2799 of the aspiration pump can be linked by the cam assembly 2710, which in turn can be driven by a single drive mechanism. The drive mechanism configured to cause oscillating movements can vary including electric, piezoelectric, magnetostrictive, electromagnetic, hydraulic, pneumatic, mechanic, or other type of drive mechanism known in the art. The configuration of the motor can vary including, any of a variety of rotation motors, stepper motor, AC motor, DC motor, a piezoelectric motor, a voice coil motor, a brushless DC motor or any type of motor or driver suitable for rotating a shaft. The motor may be coupled to a gear reduction system such as a harmonic drive to produce the desired output speed. In an implementation, the motor can be an electric motor that incorporates gear reduction via a gearbox or other mechanism.

The drive mechanism can include a motor positioned within the durable portion 3210 that upon coupling the durable portion 3210 to the disposable portion 3205 can drive both the aspiration pump and the oscillating elongate member 2755. The motor can be coupled to the rotating cam 2769 via a coupler 2795 extending outside the durable portion 3210 (see FIG. 1B) configured to engage with a cam coupler 3245 (see FIG. 10B) available within the disposable portion 3205. The cam assembly 2710 is illustrated as being a part of the disposable portion 3205, but it should also be appreciated that at least a portion of the cam assembly 2710, including the rotating cam 2769, distal cutter cam 3169, cam follower 3190, can be a part of the durable portion 3210. The cam 2769, cam coupler 3245, and motor coupler 2795 all spin together as the motor rotates. As discussed above, the cam 2769 converts this rotary motion into axial movement of the pistons 2799 as well as axial movement of the elongate member 2755.

Faster spin of the motor results in faster spin of the cam 2769. The extension of the button rod 3127 into the proximal portion (e.g. the reusable, durable portion 3210) discussed above can affect the speed of the motor. For example, speed of rotation of the motor can be controlled by a potentiometer linked to the trigger 3125 or a non-contact sensor configured to sense motion of the trigger. A potentiometer ribbon can extend between a distal end region of the durable portion 3210 and configured to activate the potentiometer. The proximal end of the button rod 3127 can interact with the distal end of the potentiometer ribbon extending within the durable portion 3210. Movement of the potentiometer ribbon can activate the potentiometer. The potentiometer can change the speed of the motor rotation.

As discussed above, the amount and type of vacuum selected by a user can depend on the phase of the procedure. During a first phase of use, aspiration through the device 2700 may be continuous, low flow type aspiration. During a second phase of use, aspiration through the device 2700 may be pulsatile, high flow configuration. Thus, the same pump can be selectively actuated between a continuous vacuum having a low-level flow rate (e.g. 2 mL/min, or 10 mL/min, up to about 20 mL/min) and pulsatile vacuum having a higher flow rate (e.g. 30 mL/min or between 20-50 mL/min). The different vacuum types and level of vacuum achieved can be a function of trigger actuation (i.e. increased trigger depression increases aspiration and switches the device from continuous smooth flow to pulsatile flow). The continuous aspiration upon initial trigger depression can be useful for providing a small amount of steady suction to help attract tissue towards the tip of the elongate member 2755 prior to cutter oscillation.

The trigger 3125 can have a plurality of positions configured to turn on or off (or increase or decrease) one or more functions of the device. As an example, the trigger 3125 can be actuated to move a first amount as a percentage of total travel capable of the input (e.g. greater than 0%, but less than 5%). The trigger 3125 actuation can cause a valve to open the irrigation inflow line 155 to initiate flow of irrigation fluid from an irrigation source towards the instrument 2700. This can place the instrument 2700 in an initial irrigation-only phase in which the irrigation inflow line 155 is primed with irrigation fluid and the instrument 2700 is able to deliver irrigation fluid to the treatment site. Alternatively, irrigation-only phase can be initiated with a separate actuator either on the instrument 2700 or on the irrigation source or irrigation line. The trigger-initiated, irrigation-only phase is not intended to be limiting, nor is it a requirement of the trigger actuation sequence. The trigger 3125 of the instrument 2700 can be actuated to move a second amount as a percentage of total travel capable of the input (e.g. greater than 5%, but less than a second amount of total travel). The trigger 3125 actuation can be sufficient to cause the motor to start spinning the cam 2769, which in turn can cause the pistons 2799 to start bouncing in their piston chambers 2704. The trigger 3125 actuation may not be sufficient to shift the piston stop 2727 away from the piston chambers 2704. This initiates the background low flow of the pump such that the instrument can begin drawing fluid and material towards the elongate member 2755 and into the waste outflow line 165. Irrigation fluid from the irrigation source can continue to be delivered toward the eye, preferably such that the fluid volume entering the eye is substantially equal to the fluid volume exiting the eye. This places the instrument 2700 in an irrigation-plus-low flow continuous aspiration phase. The background FA-only flow can have a low flow rate such as about 2 mL/minute at the lower range of trigger depression up to about 20 mL/minute at the upper range of trigger depression. The trigger 3125 can be actuated to move a third amount as a percentage of total travel capable of the input (e.g. greater than 50% up to about 100%). This third amount can switch the instrument from the low continuous aspiration into a higher, pulsed aspiration. The trigger 3125 can shift the piston stop 2727 away from the piston chambers 2704 such that the bouncing pistons 2799 can travel the full proximal distance within the piston chambers 2704. As discussed elsewhere herein, this can also allow the pistons 2799 to drop off the ledge 2726 of the cam 2769 creating the spikes in negative pressure. The irrigation supply can continue. The trigger position can additionally initiate oscillation of the elongate member 2755. This places the instrument 2700 in an irrigation-plus-pulsed aspiration phase or an irrigation-plus-pulsed aspiration-plus-cutting phase. The mechanical oscillation of the cutting phase can be initiated once the trigger 3125 position reaches an upper threshold (e.g., greater than 50% travel). The mechanical oscillation of the cutting phase can also increase to higher frequencies as the trigger is further depressed beyond that upper threshold. Once the procedure completes, the user can adjust the trigger 3125 back down to 0% to turn off aspiration and oscillation.

As discussed above, the trigger 3125 can switch the oscillation of the elongate member 2755 on and off in real-time depending on the degree of trigger actuation. The cutter spline 3162 shown in FIGS. 10A-10C is a unitary element coupled to a proximal end of the elongate member 2755. The cutter spline 3162 in this implementation moves distally as a function of the spring 3135 and moves proximally with the proximal cam follower 3190 to cause oscillating motion of the elongate member 2755. The motion of the cutter spline 3162 is linked to rotation of the cam 2769, which in turn is driven by the motor.

In another implementation shown in FIGS. 7A-7B and FIGS. 11A-11B, the cutter spline 3162 is not directly linked to the elongate member 2755. Rather, the proximal end of the elongate member 2755 is coupled to a distal cutter holder 3137. The cutter spline 3162 is urged in a distal direction by spring 3135 and the cutter holder 3137 is urged in a proximal direction against a distal-facing surface of the cutter spline 3162 by spring 3138. As the cutter spline 3162 reciprocates back and forth as discussed above, the distal cutter holder 3137 and the elongate member 2755 can remain stationary. The proximal end of the elongate member 2755 is received within a bore 3139 of the cutter holder 3137. An upper surface of the cutter holder 3137 has a notch 3140 sized to receive a latch 3142 movably coupled to the button rod 3127. When the trigger 3125 is in a resting position, the latch 3142 is urged in a downward direction by spring 3146 such that the latch 3142 is engaged with the notch 3140 of the cutter holder 3137 and maintains the cutter holder 3137 and elongate member 2755 stationary. As the trigger 3125 is depressed and the button rod 3127 slides proximally along the longitudinal axis A and the latch 3142 moves up a ramp 3144 on the button rod 3127 (see FIG. 11B). The ramp 3144 draws the latch 3142 up out of the notch 3140 releasing the cutter holder 3137. With the cutter holder 3137 released from engagement with the latch 3142, the cutter holder 3137 can now oscillate with the cutter spline 3162. The cutter holder 3137 is struck on its proximal end by the distal end of the cutter spline 3162 when the cam assembly and thus, the cutter spline 3162 drops forward urging the cutter holder 3137 in a distal direction as well. The spring 3138 compresses allowing for distal motion of the cutter holder 3137 and attached elongate member 2755. The spring 3138 urges the cutter holder 3137 back in a proximal direction along with the cutter spline 3162 as the cutter spline 3162 retracts.

In some implementations, the cutter holder 3137 can be limited from moving proximally by one or more features such that proximal cam assembly and cutter spline 3162 can move proximally further away from the cutter holder 3137 such that a gap is formed. For example, a proximal cam and cutter spline 3162 can be retracted by 0.100" while the cutter holder 3137 only retracts 0.020". In this example, a gap is formed between the two components. When the proximal cam follower 3190 is urged forward (distally) by the spring 3135, it moves forward uninhibited until the cutter spline 3162 strikes the cutter holder 3137. In this manner the momentum of the proximal cam assembly and cutter spline 3162 can be imparted into the cutter holder 3137 and a higher speed of forward excursion of the elongate member 2755 can be achieved. The mass of the proximal cam assembly can be adjusted to be larger than the cutter holder 3137 such that the momentum transferred to the cutter holder 3137 is optimized for a given speed of the elongate member 2755. Speeds can be between 2 m/s to 100 m/s.

The latch 3142 engages with the ramp 3144 when the trigger 3125 is actuated a threshold amount of total travel. For example, as discussed above, oscillation of the elongate member 2755 can be initiated upon reaching about 50% travel of the total travel path of the trigger 3125. Upon release of the trigger 3125, the spring 3123 of the button rod 3127 urges the button rod 3127 back in a distal direction causing the ramp 3144 to move distally away from engagement with the latch 3142. The spring 3146 of the latch 3142 urges the latch 3142 downward into the notch 3140 once again preventing oscillation of the cutter holder 3137 and the elongate member 2755.

The notch 3140 can have a size sufficient to receive a forward hard stop 3148. As the cutter holder 3137 shoots forward, a proximal end of the notch 3140 can abut against the forward hard stop 3148 preventing further distal motion of the cutter holder 3137 (see FIG. 7B). The travel distance between a fully extended position and a fully retracted position of the elongate member 2755 can be a function of the size of the notch 3140 or, more specifically, the distance between the hard stop 3148 and the distal end of the notch 3140. In some implementations, the distance is between about 0.05 mm to about 1.0 mm or between about 0.1 mm to about 0.5 mm.

The instrument can also incorporate one or more inputs configured to prevent oscillation of the elongate member 2755. In an implementation, the instrument 2700 can incorporate a selector ring 3136 such as an annular structure coupled to an outer surface of the housing, such as the disposable portion 3205 of the housing (see FIGS. 2A-2B). The selector ring 3136 can be twisted manually by a user to switch off cutting function of the instrument by preventing oscillation of the elongate member 2755. For example, in order to place the instrument 2700 in an irrigation/aspiration-only mode the selector ring 3136 can be moved into a first position that blocks the oscillating movements of the elongate member 2755. The instrument 2700 may then be placed into an irrigation/aspiration/cutting mode by twisting the selector ring 3136 into a second position that allows for cutting function of the elongate member 2755. Preferably, the instrument 2700 may be placed into irrigation-only, irrigation/aspiration-only, and irrigation/aspiration/cutting modes without needing to twist the selector ring 3136. For example, the degree of depression of the trigger 3125 can turn on and/or off different functions of the instrument as discussed above.

During a procedure, lens material and other tissue can block the opening of the elongate member 2755. Vacuum can build within the instrument while the aspiration pump continues to run. In some instances, the vacuum built up within the instrument can be greater than 600 mmHg. The built up vacuum within the instrument may hold fix material against the opening of the elongate member 2755 preventing dissipation of the vacuum upon release of the trigger 3125. The material may be stuck onto the elongate member 2755, which can be problematic if the material is the iris or some other part of the eye that the surgeon does not want to remove. The instruments described herein can incorporate a bypass valve 3526 that allows vacuum to dissipate when the trigger 3125 is released.

The bypass valve 3526 can be coupled functionally to the multi-stage trigger 3125. In some implementations, when the trigger 3125 is idle or positioned at a neutral position, the valve 3526 can be open and the venting mechanism can actively vent the device. When the trigger 3125 is activated to aspirate, the venting mechanism can be shut off. FIGS. 12A-12H illustrate an implementation of the venting mechanism coupled to actuation of the multi-stage trigger 3125. As described elsewhere herein, the trigger 3125 in its first, idle configuration can be biased upwards such that upon release of manual pressure on the trigger 3125 aspiration shuts off. Downward motion of the trigger 3125 can trigger aspiration (as well as irrigation and/or oscillation as described elsewhere herein). Downward motion of the trigger 3125 can also cause motion of a shutter 3126 coupled to an underside of the trigger 3125. The shutter 3126 can insert between the front manifold 3261 and the vacuum manifold 2774 thereby affecting aspiration drawn through the device. Thus, when the trigger 3125 is in the idle configuration and biased upwards, the shutter 3126 is in a configuration suitable for venting the system. When the trigger 3125 is urged downwards to activate aspiration, the shutter 3126 is in a configuration suitable for creating suction and venting is turned off.

Figure 12A:
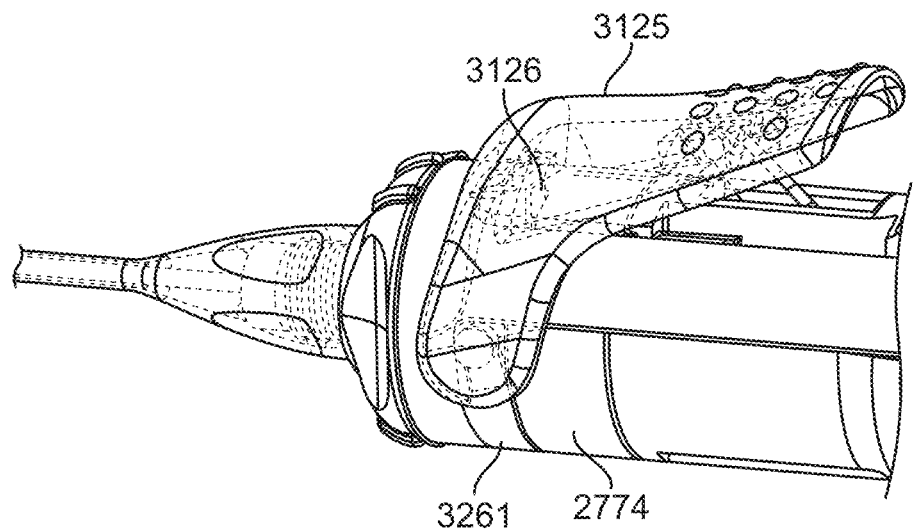
FIGS. 12A-12B illustrate an implementation of a venting mechanism coupled to a multi-stage trigger.
Figure 12B:
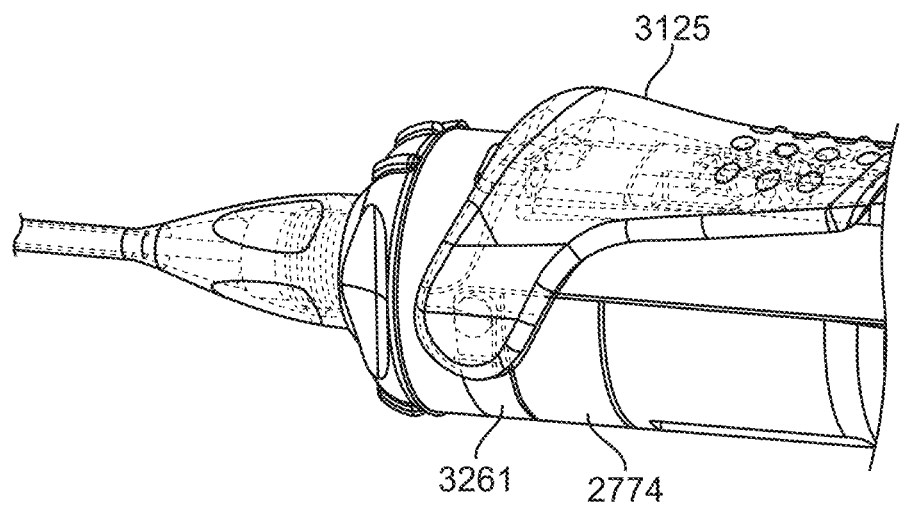
Figure 12F:
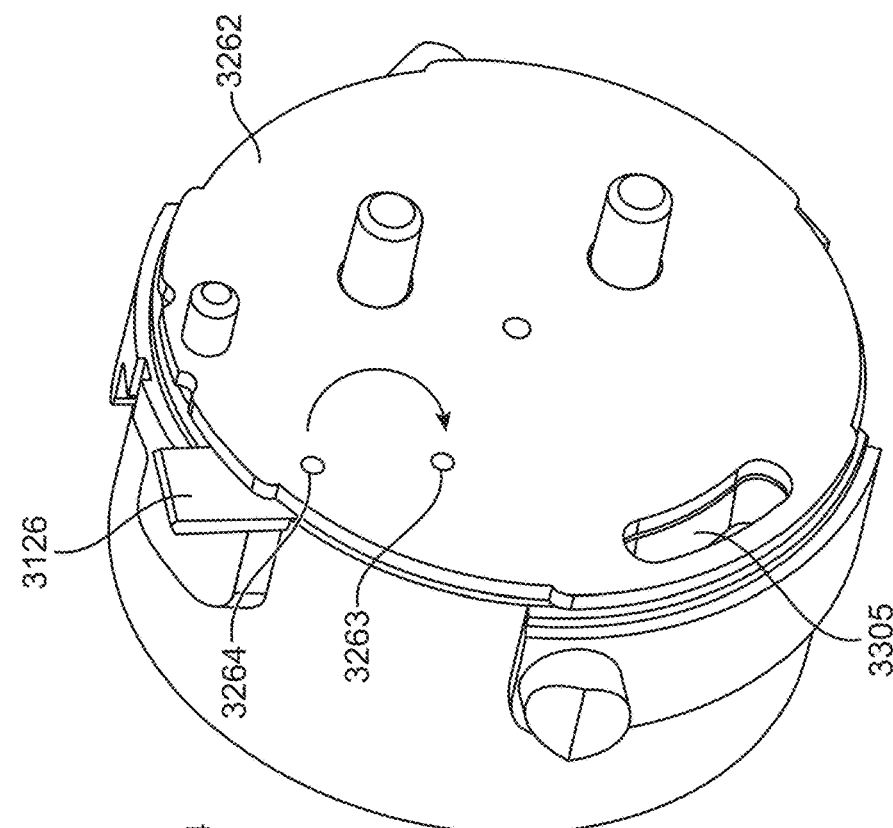
FIGS. 12E-12F illustrate the venting mechanism of FIGS. 12C-12D from a proximal end perspective through the vacuum manifold in transparency.
Figure 12E:
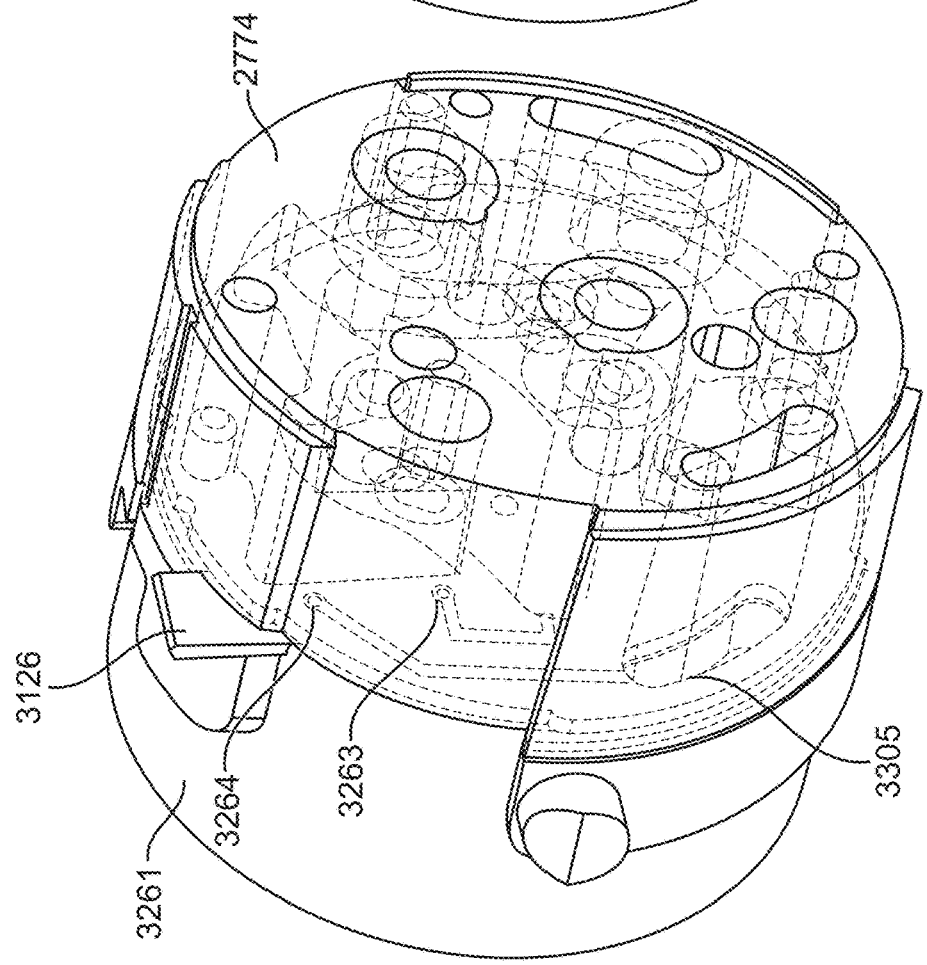
Figure 12H:
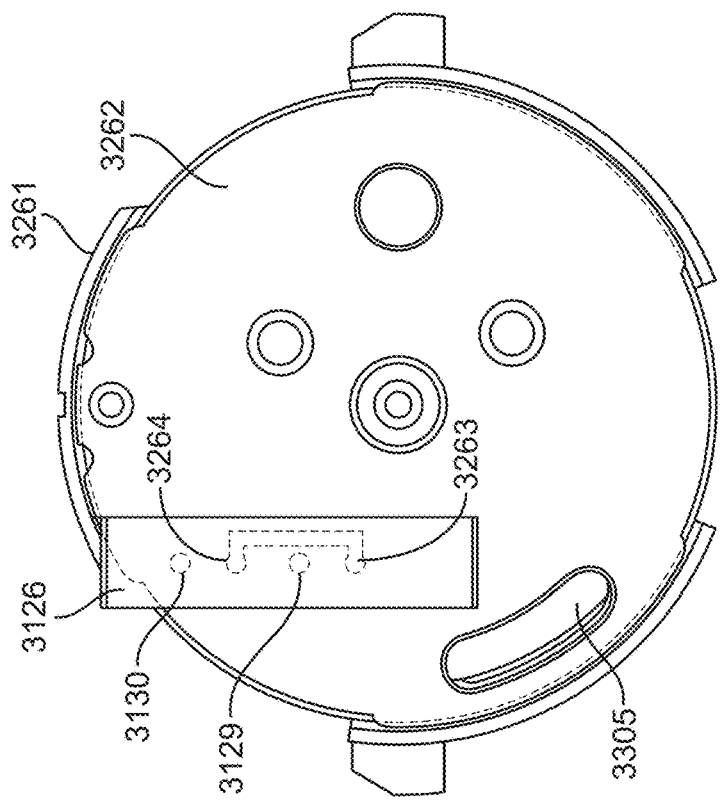
FIGS. 12G-12H illustrate the venting mechanism of FIGS. 12C-12D from a proximal end perspective without the vacuum manifold shown.
Figure 12G:
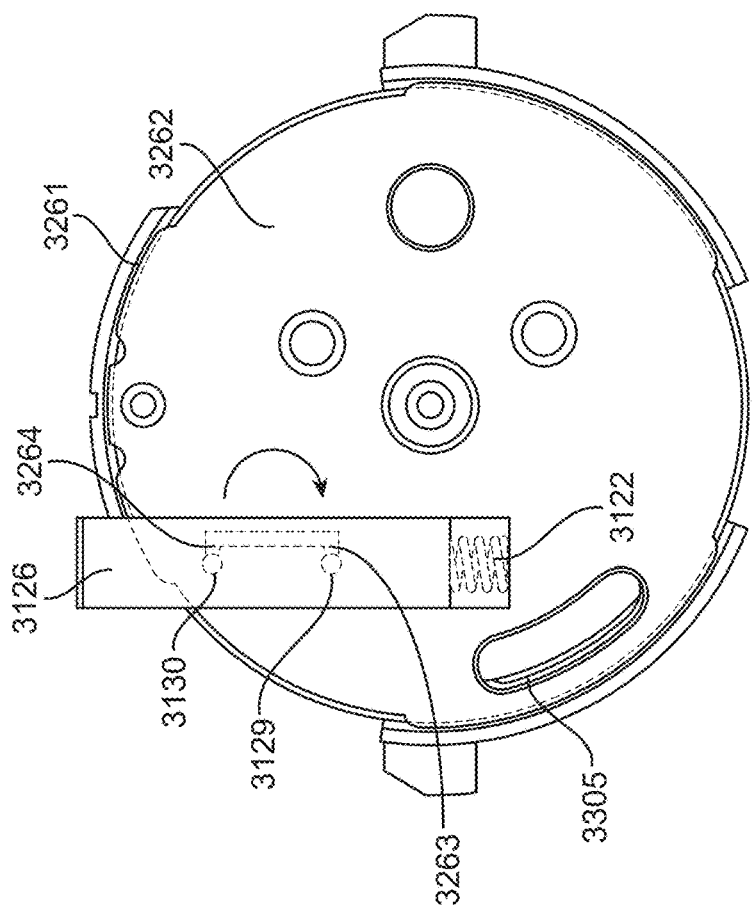
Figure 13A:
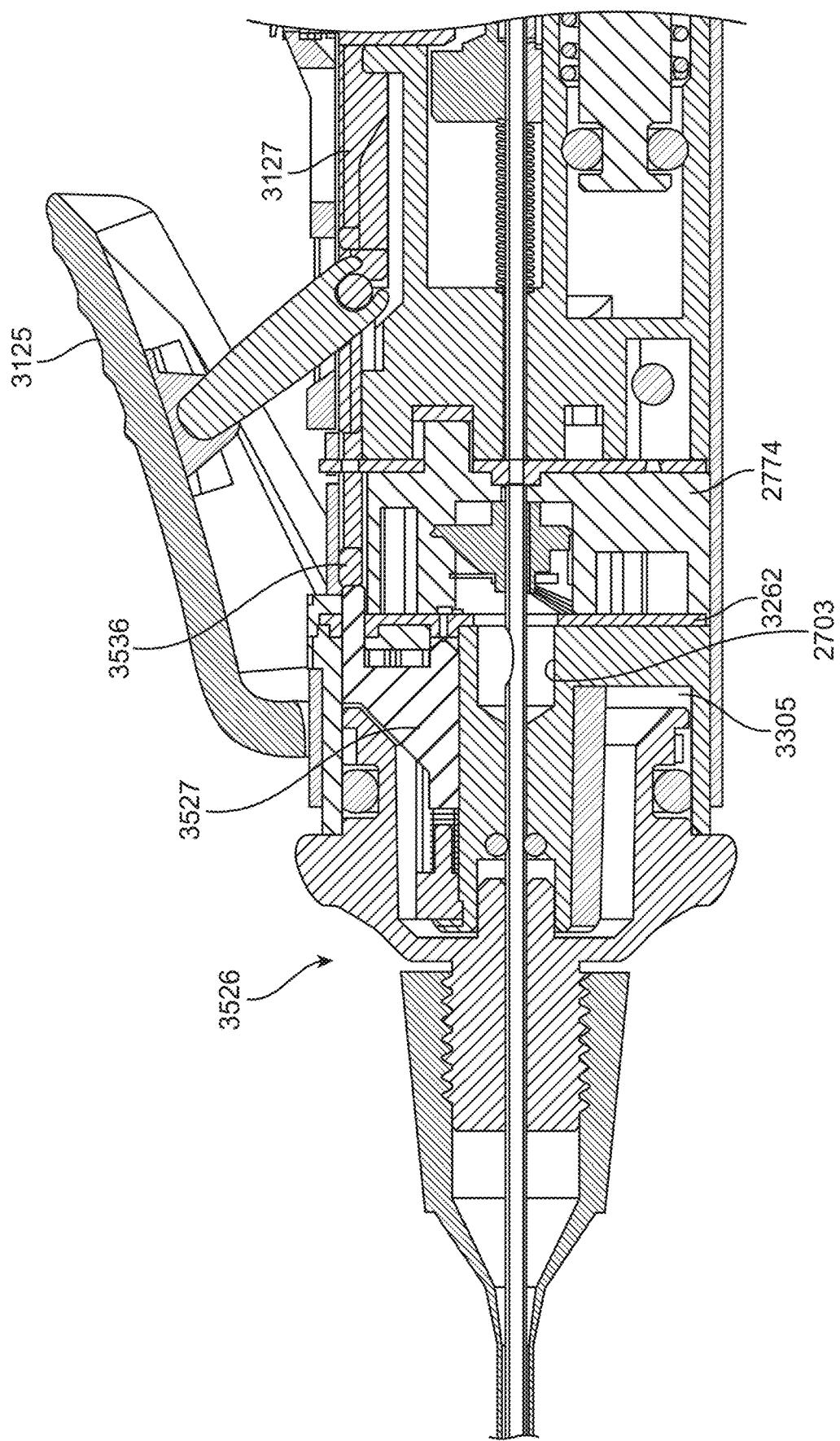
FIG. 13A is a cross-sectional partial view of a distal end region of an instrument showing an implementation of a venting mechanism coupled to a multi-stage trigger.
Figure 13D:
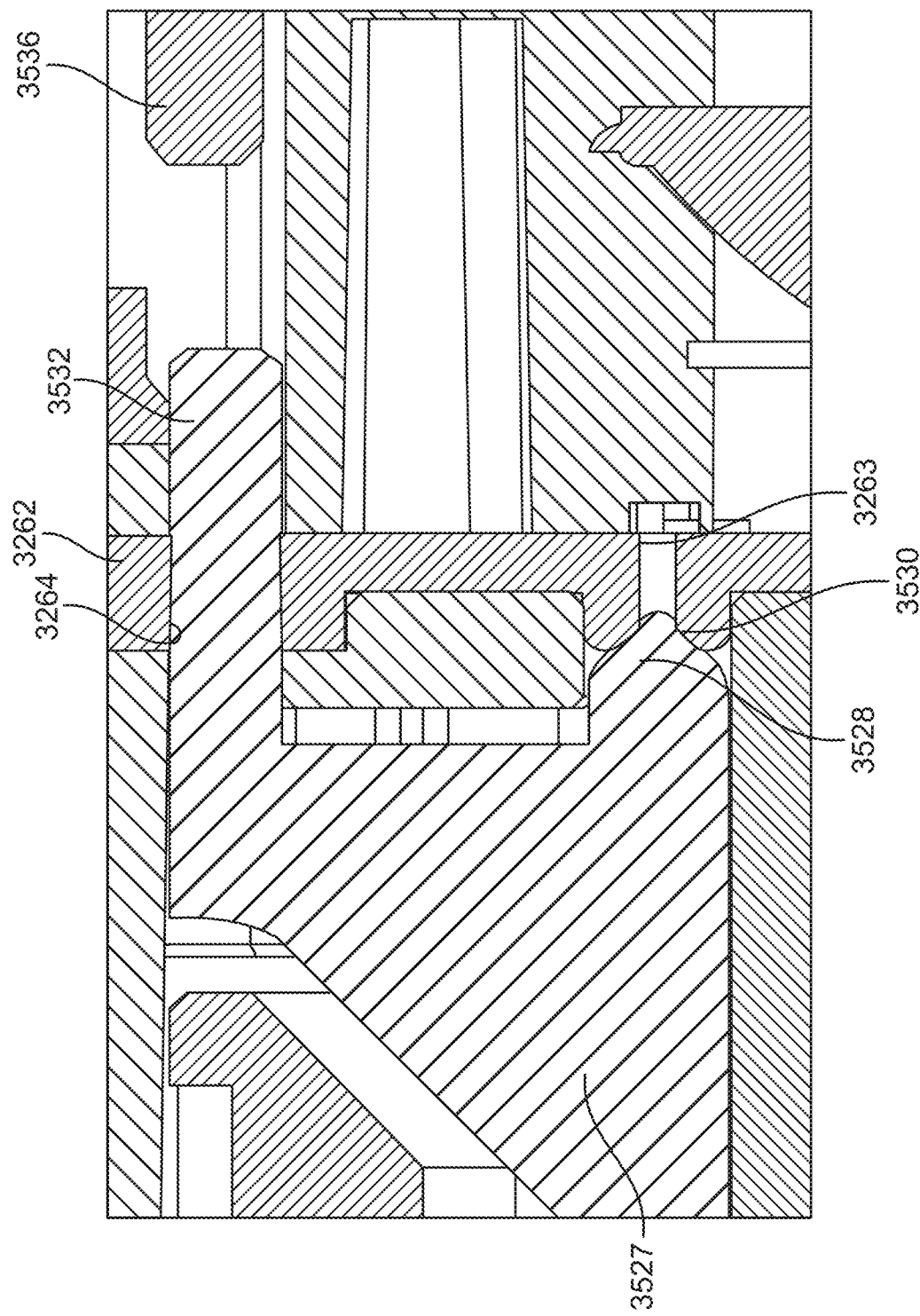

FIGS. 12C-12D show the vacuum manifold 2774 covered by a gasket 3262. The gasket 3262 is shown positioned on a distal end of the vacuum manifold 2774 such that the gasket 3262 separates the vacuum manifold 2774 from the front manifold 3261. As described elsewhere herein, the vacuum manifold 2774 and the gasket 3262 can define a vacuum chamber 2703. An irrigation fluid channel 3305 can extend through the vacuum manifold 2774 and the gasket 3262. The gasket 3262 can include a first vent opening 3263 and a second vent opening 3264 through its thickness. The first vent opening 3263 may fluidly connect with the vacuum chamber 2703 and the second vent opening 3264 may fluidly connect with the irrigation fluid channel 3305. FIGS. 12E-12F show the shutter 3126 positioned between the front manifold 3261 and the gasket 3262 covering the vacuum manifold 2774 and FIGS. 12G-12H show the relative alignment of the shutter 3126 and the gasket 3262. The shutter 3126 can likewise include a first vent opening 3129 and a second vent opening 3130 through its thickness. The shutter 3126 can be urged upward such as with a shutter spring 3122 when the device is idle. The shutter 3126 in the upward position results in the first and second vent openings 3129, 3130 of the shutter 3126 to align with the first and second vent openings 3263, 3264 of the gasket 3262. Alignment of the openings completes a fluid channel between the vacuum chamber 2703 and the irrigation fluid channel 3305 causing any negative pressure within the system to dissipate. FIGS. 12C-12D and FIG. 12G illustrate the venting of negative pressure between the vacuum chamber 2703 and the irrigation fluid channel 3305. The arrows illustrate the venting path from the higher-pressure irrigation fluid channel 3305 and the lower pressure vacuum chamber 2703 when the vent openings 3129, 3130 of the shutter 3126 align with the vent openings 3263, 3264 of the gasket 3262. Urging the trigger 3125 downward may also move the shutter 3126 downward between the manifolds 2774, 3261. The vent openings 3129, 3130 of the shutter 3126 may thereby be urged out of alignment with the vent openings 3263, 3264 of the gasket 3262 to shut off the fluid channel between the vacuum chamber 2703 and the irrigation fluid channel 3305 (see FIG. 12H). This allows for the generation of aspiration pressure within the vacuum chamber 2703 as described elsewhere herein.

Movement of the user-activated shutter 3126 can determine whether the vacuum that is generated within the vacuum chamber 2703 of the device is vented or maintained. The vacuum chamber 2703 may be connected to atmospheric air, to the irrigation fluid pathway 3305, to the waste fluid pathway 2709, or any other cavity. By doing so, any maintained vacuum within the vacuum chamber 2703 is vented through this connection. Fluid or air may enter the vacuum chamber 2703 and the vacuum level within the cavity will decrease. It should be appreciated that the shutter 3126 need not be coupled to the trigger 3125 and can have a separate actuator that can be activated when a user desires to release the vacuum from the device.

The configuration of the bypass valve 3526 can vary. FIGS. 13A-13D shows another implementation of the bypass valve 3526 linked to trigger actuation. In this implementation, the bypass valve 3526 can incorporate a movable shuttle 3527 configured to move parallel to the longitudinal axis of the instrument as opposed to perpendicular to the longitudinal axis like the shutter 3126 described above. The vacuum manifold 2774 is separated from the front manifold 3261 by a gasket 3262. The gasket 3262 can have at least a first opening 3263 and a second opening 3264 (see FIGS. 13C-13D). The first opening 3263 extends between the irrigation fluid channel 3305 and the vacuum chamber 2703. The second opening 3264 extends between the irrigation fluid channel 3305 and the channel of the button rod 3127.

The shuttle 3527 of the bypass valve 3526 can include a first protrusion 3528 configured to seat with a valve seat 3530 surrounding the first opening 3263 through the gasket 3262. The shuttle 3527 of the bypass valve 3526 can include a second protrusion 3532 configured to extend through and seal with the second opening 3264 in the gasket 3262. The bypass valve 3526 can also include a valve spring 3534 biased to urge the first protrusion 3528 of the shuttle 3527 against the first opening 3263 (see FIG. 13B).

The bypass valve 3526 opens when the trigger is released. The trigger 3125 returns into an upward position and the button rod 3127 slides distally relative to the housing. A distal extension 3536 of the button rod 3127 can press against the second protrusion 3532 of the shuttle 3527 urging the first protrusion 3528 away from the valve seat 3530 uncovering the first opening 3263 (see FIG. 13C). This allows irrigation fluid to flow into the vacuum area and dissipates any vacuum within the housing.

The bypass valve 3526 closes when the trigger is actuated. The trigger 3125 is urged downward and the button rod 3127 slides proximally relative to the housing. The distal extension 3536 of the button rod 3127 is moved away from the second protrusion 3532 of the shuttle 3527. The valve spring 3534 urges the shuttle 3527 of the bypass valve 3526 proximally towards the valve seat 3530. The first protrusion 3528 slides back into the valve seat 3530 covering and sealing the first opening 3263 (see FIG. 13D). This prevents irrigation fluid from flowing into the vacuum area and vacuum builds within the housing.

In other implementations, the bypass valve 3526 is closed when the trigger 3125 is in the neutral position preventing any connection between the irrigation path and the vacuum path and the motor does not spin. In use, a user may press the trigger 3125 away from the neutral position to cause vacuum to build within the instrument to perform a procedure. If the user would like to release the accumulated vacuum in the instrument, for example, when the tip of the shaft becomes occluded during the procedure, the user can let go of the trigger 3125 returning it to the neutral position and then urge the trigger into an upward position to actively open the bypass valve 3526 to release the accumulated vacuum in the instrument. Any of a variety of configurations are considered herein to open the bypass valve 3526 to release accumulated vacuum in the instrument.

The displacement or travel distance of the tip of the elongate member 2755 can vary, but is generally greater than phacoemulsification tips known in the art. Typical phacoemulsification tips have a tip displacement of about 0.1 mm and move at a frequency of between about 20-40 kHz. The tip of the elongate member 2755 described herein can have a greater displacement distance and a lower frequency. For example, the displacement achieved by the tip of the elongate member 2755 can be between about 0.05 mm-1.0 mm at a frequency of about 2-2,000 Hz. In this way, the devices described herein may not be ultrasonic and may not generate the heat associated with harmful effects in the eye during cataract surgery. In some implementations, the tip of the elongate member 2755 is pushed forward by the spring 3135 as described above. A longer stroke distance can allow the tip to achieve a higher final extension speed at the time of impact with eye tissue.

When in use, elongate member can retract in a proximal direction with a retraction speed profile and advancing in a distal direction with an extension speed profile. The retraction speed profile can be different from the extension speed profile. Additionally, the movement profile of the elongate member can be coordinated with a particular vacuum profile. For example, while a pulse of vacuum is being applied through the elongate member, the elongate member can be simultaneously fired in the distal direction. Where the elongate member is described as moving in forward and distal directions relative to the treatment site, vibrations of the elongate member are considered as well. The elongate member can be vibrated in a similar fashion to conventional phacoemulsification systems. Thus, the elongate member can be vibrated while a pulse of vacuum is applied and at some phase in the vacuum pulse or thereafter, the vibration and the vacuum can be turned off such that the system comes to rest before initiating a vibration-vacuum sequence again.

The vacuum source of the device can be configured to provide pulses of discontinuous negative pressure. Movement of the pistons creating vacuum pulses can be coordinated or linked (directly or indirectly) to phases of movement of the elongate cutter member as discussed elsewhere herein. A pulse of aspiration can be drawn through the lumen of the elongate member during at least a portion of the extension as the elongate member moves in a distal direction and/or during at least a portion of the retraction as the elongate member moves in a proximal direction. The coordination between the movement and/or vibration of the elongate member and the vacuum applied through the elongate member is described in U.S. Patent publication No. 2018/0318132, filed May 3, 2018 and U.S. Patent publication No. 2019/0365567, filed Jun. 4, 2019, which are incorporated by reference herein in their entireties.

One or more aspects of the devices described herein can be programmed by a user. The instrument 2700 can include a computing unit including a control processor, memory, and/or communication module in operative communication with one or more components of the instrument (e.g. drive mechanism, vacuum source, or other components of the instrument). A user can also program the microsurgical instrument 2700 using an external computing device in communication with the instrument 2700.

A user can program one or more aspects of the drive mechanism, for example, the speed profile of the motor of the instrument. The control processor can be programmed by an input on the device itself or programmed remotely such as by an external computing device having an input. The control processor can operate according to program instructions stored in a memory. Any of a variety of adjustable functions of the instrument may be programmed this way including, but not limited to travel distance of the elongate member, frequency of oscillation of the elongate member, extension speed profile, retraction speed profile, maximum extension speed, minimum extension speed, maximum retraction speed, minimum retraction speed, average extension speed, average retraction speed, vacuum level, or any other aspect of the motion profile. In some implementations, the distance the elongate member moves with each cycle can be adjustably programmed such that the amplitude of its oscillation is selectable within a range of about 0.5 Hz to about 5000 Hz, or frequency in a range of about 2 Hz to about 2000 Hz. The oscillation frequency can be less than ultrasonic, for example, less than about 20,000 Hz or within the ultrasonic range (e.g. about 20,000 Hz, to about 120,000 Hz, up to the gigahertz range).

Control of the instrument 2700, such as the drive mechanism of the instrument 2700, can be completed with a motion controller, electronic speed controller, or the like. The actuator or input for the motion controller can be an on/off sort of input to initiate cutting and/or vacuum. The controller can be programmed (e.g. remotely or on the device itself) to have a minimum and/or maximum speed upon actuation of the input. For example, the drive mechanism of the instrument can be programmed to have a minimum and/or maximum speed upon actuation of the input or, in the case of fluid infusion and aspiration, the instrument 2700 can be programmed to have a minimum and/or maximum fluid pressure upon actuation of an input. Thus, the instruments described herein can be programmed using inputs adjustable by a user as well as by pre-programmed instructions that impact the one or more aspects of the instrument upon actuation of the inputs One of more aspects of the aspiration pump can also be programmed by a user to control the vacuum applied at the distal end region of the elongate member including, but not limited to flow rate of aspiration, minimum vacuum pressure, maximum vacuum pressure, frequency of vacuum pulses, disable/enable various modes (i.e., pulsed mode or burst mode), adjust parameters of modes (i.e., on time vs. off time during pulse mode), and various other controllable parameters of the instrument including any other aspect of the vacuum profile or motion profile. In some implementations, the flow rate of aspiration can be adjustably programmed within a range of between about 5-100 ml/min.

It should be appreciated that the asymmetric motion profile with or without the vacuum pulse described herein can be applied to known phacoemulsification systems typically used for cataract surgery and vitrectomy. Conventional phacoemulsification systems configured to move an elongate member at ultrasonic frequency to remove eye tissue can implement the one or more motion profiles and/or vacuum profiles as described herein via software or hardware, for example by circuits providing a certain voltage causing the asymmetric movements. Thus, the asymmetric motion profiles and pulsed vacuum profiles described herein can be applied to a machine configured to oscillate at ultrasonic frequencies.

The instruments described herein can be battery powered and incorporate one or more batteries within a region of the housing, either internally or coupled to a region of the housing such as within a modular, removable battery pack. The battery can have different chemical compositions or characteristics. For instance, batteries can include lead-acid, nickel cadmium, nickel metal hydride, silver-oxide, mercury oxide, lithium ion, lithium ion polymer, or other lithium chemistries. The device can also include rechargeable batteries using either a DC power-port, induction, solar cells, or the like for recharging. Power systems known in the art for powering medical devices for use in the operating room are also to be considered herein such as spring power or any other suitable internal or external power source. In some implementations, rather than the battery back mounted on or in the handle, which can increase the size of the handle, the battery pack can be mounted elsewhere such as on a user's arm or wrist of the arm holding the instrument during a procedure. A short cable connector can connect the mounted battery back to the device such that only this linkage extends from the handle of the device during use. Thus, no foot pedal or other tethering connection need be linked to the device. This can provide the user with more portability, flexibility, and freedom of movement and without worrying about catching cables or other tethers during use.

Aspects of the subject matter described herein may be realized in digital electronic circuitry, integrated circuitry, specially designed ASICs (application specific integrated circuits), computer hardware, firmware, software, and/or combinations thereof. These various implementations may include an implementation in one or more computer programs that are executable and/or interpretable on a programmable system including at least one programmable processor, which may be special or general purpose, coupled to receive signals, data and instructions from, and to transmit signals, data, and instructions to, a storage system, at least one input device, and at least one output device.

These computer programs (also known as programs, software, software applications, or code) include machine instructions for a programmable processor, and may be implemented in a high-level procedural and/or object-oriented programming language, and/or in assembly/machine language. As used herein, the term "machine-readable medium" refers to any computer program product, apparatus, and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

In various implementations, description is made with reference to the figures. However, certain implementations may be practiced without one or more of these specific details, or in combination with other known methods and configurations. In the description, numerous specific details are set forth, such as specific configurations, dimensions, and processes, in order to provide a thorough understanding of the implementations. In other instances, well-known processes and manufacturing techniques have not been described in particular detail in order to not unnecessarily obscure the description. Reference throughout this specification to "one embodiment," "an embodiment," "one implementation," "an implementation," or the like, means that a particular feature, structure, configuration, or characteristic described is included in at least one embodiment or implementation. Thus, the appearance of the phrase "one embodiment," "an embodiment," "one implementation," "an implementation," or the like, in various places throughout this specification are not necessarily referring to the same embodiment or implementation. Furthermore, the particular features, structures, configurations, or characteristics may be combined in any suitable manner in one or more implementations.

The use of relative terms throughout the description may denote a relative position or direction. For example, "distal" may indicate a first direction away from a reference point. Similarly, "proximal" may indicate a location in a second direction opposite to the first direction. However, such terms are provided to establish relative frames of reference, and are not intended to limit the use or orientation of the device to a specific configuration described in the various implementations.

While this specification contains many specifics, these should not be construed as limitations on the scope of what is claimed or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination. Similarly, while operations are depicted in the drawings in a particular order, this should not be understood as requiring that such operations be performed in the particular order shown or in sequential order, or that all illustrated operations be performed, to achieve desirable results. Only a few examples and implementations are disclosed. Variations, modifications and enhancements to the described examples and implementations and other implementations may be made based on what is disclosed.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together."

A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together."

Use of the term "based on," above and in the claims is intended to mean, "based at least in part on," such that an unrecited feature or element is also permissible.

What is claimed:

1. A medical device for removing lens tissue from inside a capsular bag of an eye, the device comprising:
a housing sized to be held in a hand;
a shaft extending distally from and configured to oscillate relative to the housing, the shaft comprising a distal end region adapted to access a lens inside the capsular bag of the eye and having a lumen, and having a proximal end coupled to a cutter holder having a distal-facing surface, a proximal-facing surface, and an upper surface, the upper surface defining a notch;
a cam assembly operatively coupled to a vacuum generation source positioned within the housing, the cam assembly comprising a first portion operatively coupled to the vacuum generation source and a second portion operatively coupled to the first portion and to the shaft, wherein the first portion is capable of rotating about an axis to cause the vacuum generation source to generate vacuum through the lumen, and
wherein the second portion is capable of rotating about the axis with the first portion to cause the shaft to oscillate; and
a single, multi-way trigger on the housing configured to activate rotation of the cam assembly, the trigger being operatively coupled to a latch and a piston stop, wherein a first degree of actuation of the trigger causes the vacuum generation source to generate vacuum within the lumen of the shaft, and wherein a second degree of actuation of the trigger causes the shaft to oscillate as the second portion rotates, wherein the latch is configured to prevent the shaft from oscillating as the second portion rotates when the latch is positioned within the notch, and wherein the second degree of actuation of the trigger releases the latch from the notch allowing the shaft to oscillate as the second portion rotates.

2. The device of claim 1, wherein the vacuum generation source comprises a plurality of pistons, each of the plurality of pistons being housed within a respective cylinder, each of the cylinders fluidly coupled to the lumen of the shaft, wherein the latch is configured to prevent the shaft from oscillating as the second portion rotates, and wherein the piston stop is configured to limit proximal travel of the plurality of pistons within the respective cylinders, wherein the second degree of actuation of the trigger simultaneously releases the latch and rotates the piston stop away from the plurality of pistons, initiating shaft oscillation and pulsatile vacuum.

3. The device of claim 1, further comprising a cutter spline configured to abut against the proximal-facing surface of the cutter holder, the cutter spline coupled to the second portion of the cam assembly.

4. The device of claim 3, wherein the trigger has a resting position, the latch is engaged within the notch when the trigger is in the resting position.

5. The device of claim 4, wherein the first degree of actuation of the trigger moves the trigger from the resting position into an aspiration-only position.

6. The device of claim 5, wherein the latch remains engaged within the notch when the trigger is in the aspiration-only position.

7. The device of claim 6, wherein the second degree of actuation of the trigger moves the trigger from the aspiration-only position into an aspiration-oscillation position.

8. The device of claim 7, wherein the latch is removed from the notch when the trigger is in the aspiration-oscillation position.

9. The device of claim 3, wherein the first degree of actuation of the trigger slides a button rod proximally along a longitudinal axis of the housing.

10. The device of claim 9, wherein the button rod comprises a ramp configured to engage with the latch causing the latch to slide along the ramp and lift out of engagement with the notch releasing the cutter holder.

11. The device of claim 10, wherein the cutter holder and the shaft are urged by the cutter spline in a distal direction and wherein the cutter holder and the shaft are urged in a proximal direction by a cutter holder spring.

12. The device of claim 11, wherein rotation of the second portion of the cam assembly urges a cam follower in the proximal direction compressing a cam follower spring.

13. The device of claim 12, wherein the shaft retracts in the proximal direction with the cam follower.

14. The device of claim 13, wherein the cam follower drops distally at a point in the rotation and the cam follower spring urges the shaft in the distal direction.

15. The device of claim 14, wherein the cutter spline moves with the cam follower.

16. The device of claim 15, wherein the cutter holder moves with the cutter spline when the latch is withdrawn from the notch.

17. The device of claim 16, wherein the cutter holder remains stationary as the cutter spline moves when the latch is engaged within the notch.

18. The device of claim 4, wherein, when the latch is engaged within the notch of the cutter holder, the cutter holder and the shaft remain stationary during rotation of the second portion.

19. The device of claim 18, wherein, when the latch is withdrawn from the notch of the cutter holder, the cutter spline, the cutter holder, and the shaft are configured to oscillate together during rotation of the second portion.

20. The device of claim 1, wherein the cam assembly is operatively rotated by a motor positioned within an interior of the housing containing the cam assembly.

21. The device of claim 20, wherein a speed of the motor is variably controlled by the trigger on the housing.

22. The device of claim 1, further comprising a bypass valve linked to actuation of the trigger, wherein the bypass valve is opened prior to actuation of the trigger and is closed upon the first degree of actuation.

* * * * *